US010098944B2

(12) United States Patent
Zhou et al.

(10) Patent No.: US 10,098,944 B2
(45) Date of Patent: Oct. 16, 2018

(54) RECOMBINANT SWINE INFLUENZA VIRUS AND USES THEREOF

(71) Applicant: University of Saskatchewan, Saskatoon (CA)

(72) Inventors: Yan Zhou, Saskatoon (CA); Aleksandar Masic, Belleville (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 15/218,748

(22) Filed: Jul. 25, 2016

(65) Prior Publication Data

US 2017/0151323 A1 Jun. 1, 2017

Related U.S. Application Data

(63) Continuation of application No. 13/559,940, filed on Jul. 27, 2012, now abandoned.

(60) Provisional application No. 61/514,156, filed on Aug. 2, 2011.

(51) Int. Cl.

| | |
|---|---|
| ***A01N 63/00*** | (2006.01) |
| ***A61K 38/00*** | (2006.01) |
| ***A61K 39/12*** | (2006.01) |
| ***A61K 39/225*** | (2006.01) |
| ***C12N 15/861*** | (2006.01) |
| ***A61K 39/145*** | (2006.01) |
| ***C12N 7/00*** | (2006.01) |
| *A61K 39/00* | (2006.01) |

(52) U.S. Cl.
CPC ............ *A61K 39/145* (2013.01); *A61K 39/12* (2013.01); *C12N 7/00* (2013.01); *A61K 2039/5254* (2013.01); *A61K 2039/544* (2013.01); *A61K 2039/552* (2013.01); *A61K 2039/70* (2013.01); *C12N 2760/16121* (2013.01); *C12N 2760/16134* (2013.01); *C12N 2760/16151* (2013.01); *C12N 2760/16162* (2013.01); *C12N 2760/16171* (2013.01); *C12N 2799/025* (2013.01)

(58) Field of Classification Search
CPC ............ C12N 2760/16134; C12N 7/00; C07K 14/005; A61K 39/145; A61K 39/12
See application file for complete search history.

(56) References Cited

U.S. PATENT DOCUMENTS

| | | | |
|---|---|---|---|
| 4,693,981 | A | 9/1987 | Wiesehahn et al. |
| 5,106,619 | A | 4/1992 | Wiesehahn et al. |
| 5,578,473 | A | 11/1996 | Palese et al. |
| 5,891,705 | A | 4/1999 | Budowsky et al. |
| 6,348,450 | B1 | 2/2002 | Tang et al. |
| 6,635,246 | B1 | 10/2003 | Barrett et al. |
| 6,951,754 | B2 | 10/2005 | Hoffmann |
| 6,974,686 | B2 | 12/2005 | Parkin |
| 7,037,707 | B2 | 5/2006 | Webster et al. |
| 8,039,002 | B2 | 10/2011 | Yang et al. |
| 2004/0029251 | A1 | 2/2004 | Hoffman et al. |
| 2009/0010962 | A1 | 1/2009 | Palese et al. |

FOREIGN PATENT DOCUMENTS

| | | | | |
|---|---|---|---|---|
| WO | WO-1999/27961 | A1 | | 6/1999 |
| WO | WO-2002/064162 | A2 | | 8/2002 |
| WO | WO-2002/064162 | A3 | | 8/2002 |
| WO | WO-2002/074244 | A2 | | 9/2002 |
| WO | WO-2002/074244 | A3 | | 9/2002 |
| WO | WO-2003/028760 | A2 | | 4/2003 |
| WO | WO-2003/028760 | A3 | | 4/2003 |
| WO | WO 2008/147496 | | | 12/2008 |
| WO | WO 2011/014645 | | | 2/2011 |
| WO | WO 2011/014794 | | | 2/2011 |
| WO | WO2011014645 | | * | 2/2011 |

OTHER PUBLICATIONS

Masic et al., Elastase-Dependent Live Attenuated Swine Influenza A viruses are immunogenic and confer protection against swine influenza A virus infection in pigs, Journal of Virology, 2009, 83(19):10198-10210.*

Ferguson et al., "Ecological and Immunological Determinants of Influenza Evolution," Nature, 422:428-433 (2003).

Ha et al., "H5 Avian and H9 Swine Influenza Virus Haemagglutinin Structures; Possible Origin of Influenza Subtypes," The EMBO Journal, 21(5):865-875 (2002).

Hoffmann et al., "A DNA Transfection System for Generation of Influenza A Virus From Eight Plasmids," PNAS, 97(11)-6108-6113 (2000).

Hoffmann et al. "Eight-Plasmid System for Rapid Generation of Influenza Virus Vaccines," Vaccine, 20:3165-3170 (2002).

Hoffmann et al., "Universal Primer Set for the Full-Length Amplification of All Influenza A Viruses," Arch Virol, 146:2275-2289 (2001).

Li et al., "Generation of Replication-Competent Recombinant Influenza A Viruses Carrying a Reporter Gene Harbored in the Neuraminidase Segment," Journal of Virology, 84(22):12075-12081 (2010).

Lin et al., "Avian-to-Human Transmission of H9N2 Subtype Influenza A Viruses: Relationship Between H9N2 and H5N1 Human Isolates," PNAS, 97(17):9654-9658 (2000).

Masic et al., "Reverse Genetics-Generated Elastase-Dependent Swine Influenza Viruses are Attenuated in Pigs," Journal of General Virology, 90:375-385 (2009).

(Continued)

*Primary Examiner* — Barry A Chestnut

(74) *Attorney, Agent, or Firm* — Morrison & Foerster LLP

(57) ABSTRACT

Recombinant, chimeric porcine influenza viruses are disclosed that include hemagglutinin segments from more than one influenza virus subtype. Also described are methods of producing the recombinant influenza viruses, immunogenic compositions comprising the recombinant influenza viruses, methods of stimulating an immune response against influenza virus, and methods of treating and preventing influenza virus infection.

20 Claims, 19 Drawing Sheets

Specification includes a Sequence Listing.

(56) References Cited

OTHER PUBLICATIONS

Palese et al., "Negative-Strand RNA Viruses: Genetic Engineering and Applications," Proc. Natl. Acad. Sci. USA, 93:11354-11358 (1996).
Neumann et al., "Generation of Influenza A Viruses Entirely From Cloned CDNAS," Proc. Natl. Acad. Sci. USA, 96:9345-9350 (1999).
Neumann et al., "Genetic Engineering of Influenza and Other Negative-Strand RNA Viruses Containing Segmented Genomes," Advances in Virus Research, 53:265300 (1999).
Nguyen et al., "Isolation and Characterization of Avian Influenza Viruses, Including Highly Pathogenic H5N1, From Poultry in Live Bird Markets in Hanoi, Vietnam, in 2001," Journal of Virology, 79(7):4201-4212 (2005).
Fodor et al., "Rescue of Influenza A Virus From Recombinant DNA," Journal of Virology, 73(11):9679-9682 (1999).
GenBank: AY619961.1, "Influenza A Virus (A/Swine/Saskatchewan/18789/02(H1N1)) Hemagglutinin (HA) Gene, Complete CDS," (2004).
GenBank: AY619960.1, "Influenza A Virus (A/Swine/Saskatchewan/18789/02(H1N1)) Aneuraminidase (NA) Gene, Complete CDS," (2004).
GenBank: AY619959.1, "Influenza A Virus (A/Swine/Saskatchewan/18789/02(H1N1)) Matrix Protein 2 (M2) and Matrix Protein 1 (MI) Genes, Complete CDS," (2004).
GenBank: AY619958.1, "Influenza A Virus (A/Swine/Saskatchewan/18789/02(H1N1)) Nucleoprotein (NP) Gene, Complete CDS," (2004).
GenBank: AY619956.1, "Influenza A Virus (A/Swine/Saskatchewan/18789/02(H1N1)) Polymerase Acidic Protein 2 (PA) Gene, Complete CDS," (2004).
GenBank: AY619954.1, "Influenza A Virus (A/Swine/Saskatchewan/18789/02(H1N1)) Polymerase Subunit PB2 (PB2) Gene, Complete CDS," (2004).
GenBank: AY6I9955.1, "Influenza A Virus (A/Swine/Saskatchewan/18789/02(H1N1)) Polymerase Subunit PB1 (PB1) Gene, Complete CDS," (2004).
Gao et al., "A Nine-Segment Influenza A Virus Carrying Subtype H1 and H3 Hemagglutinins," Journal of Virology, 84(16):8062-8071 (2010).
Masic et al., "An Eight-Segment Swine Influenza Virus Harboring H1 and H3 Hemagglutinins is Attenuated and Protective Against H1N1 and H3N2 Subsypes in Pigs," Journal of Virology, 87(18):10114-10125 (2013).
Masic et al., "Elastase-Dependent Live Attenuated Swine Influenza A Viruses are Immunogenic and Confer Protection Against Swine Influenza A Virus Infection in Pigs," Journal of Virology, 83(19):10198-10210 (2009).
Shtyrya et al., "Influenza Virus Neuraminidase: Structure and Function", ACTA Nature, 2:26-32 (2009).
Agarwal, V. et al. (1999). "Recent Trends in Drug Delivery Systems: intranasal Drug Delivery," *Indian J Exp. Biol*. 37:6-16.
Almeida, a.J. et al. (1996, e-pub. Sep. 28, 2008). "Nasal Delivery of Vaccines," *J. Drug Targeting* 3:455-467.
Asanaka, M. et al. (2005). "Replication and Packaging of Norwalk Virus RNA in Cultured Mammalian Cells," *Proc. Natl. Acad. Sci. USA* 102:10327.
Chan, C.-H. et al. (2004). "Phylogenetic Analysis of Influenza B Virus in Taiwan, 1997 to 2001," *J. Microbiol. Immunol. Infect.* 37:135-144.
Chu, G. et al. (1981). "Short Communications: SV40 DNA Transfection of Cells in Suspension: Analysis of the Efficiency of Transcription and Translation of T-Antigen," *Gene* 13:197-202.
Dayoff, M.O. et al. (1983). "[47] Establishing Homologies in Protein Sequences," *Methods in Enzymology* 91:524-545.
Doe, B. et al. (Oct. 1994). "Induction of HIV-1 Envelope (gp120)-Specific Cytotoxic T Lymphocyte Responses in Mice by Recombinant CHO Cell-Derived gp120 is Enhanced by Enzymatic Removal of N-Linked Glycans," *Eur. J. Immunol.* 24(10):2369-2376.
Dos Santos Afonso, E. et al. (2005). "The Generation of Recombinant Influenza A Viruses Expressing a PB2 Fusion Protein Requires the Conservation of a Packaging Signal Overlapping the Coding and Noncoding Regions at the 5' End of the PB2 Segment," *Virology* 341:34-46.
Dreyer, K. et al. (Nov. 20, 1999). "Primary Isolate Neutralization by Hiv Type 1-Infected Patient Sera in the Era of Highly Active Antiretroviral Therapy," *AIDS Res Hum Retroviruses* 15(17):1563-1571.
Enami, M. et al. (May 1990). "Introduction of Site-Specific Mutations Into the Genome of Influenza Virus," *Proc. Natl. Acad. Sci. USA* 87:3802 3805.
Enami, M. et al. (May 1991). "High-Efficiency Formation of Influenza Virus Transfectants," *J. Virol*. 65(5):2711-2713.
Erickson, A.L. et al. (Oct. 15, 1993). "Hepatitis C Virus-Specific CTL Responses in the Liver of Chimpanzees With Acute and Chronic Hepatitis C," *J. Immunol.* 151(8):4189-4199.
Fujii, Y. et al. (Mar. 2005). "Importance of Both the Coding and the Segment-Specific Noncoding Regions of the Influenza A Virus NS Segment for Its Efficient Incorporation Into Virions," *J. Virol.* 79(6):3766-3774.
Fujii, K. et al. (Feb. 18, 2003). "Selective Incorporation of Influenza Virus RNA Segments Into Virions," *Proc. Natl. Acad. Sci. USA* 100(2):2002-2007.
Gao, Q. et al. (Jul. 2008). "A Seven-Segmented Influenza A Virus Expressing the Influenza C Virus Glycoprotein HEF," *J. Virol.* 82(13):6419-6426.
GenBank Database, particularly the Influenza Virus Resource, retrieved from <https://www.ncbi.nlm.nih.gov/genomes/FLU/Database/nph-select.cgi_last_visited> Jul. 25, 2018.
Gog, J.R. et al. (2007, e-pub. Mar. 1, 2007). "Codon Conservation in the Influenza A Virus Genome Defines RNA Packaging Signals," *Nucl. Acids Res.* 35(6):1897-1907.
Graham, F.L. et al. (Apr. 1973). "A New Technique for the Assay of Infectivity of Human Adenovirus 5 DNA," *Virology* 52(2):456-467.
Hardy, C.T. et al. (1995). "Short Communication: Egg Fluids and Cells of the Chorioallantoic Membrane of Embryonated Chicken Eggs Can Select Different Variants of Influenza A (H3N2) Viruses," *Virology* 211:302-306.
Harwood, P.J. et al. (1986). "Mapping Epitope Characteristics on Carcinoembryonic Antigen," *Br. J. Cancer* 54:75-82.
Hinshaw, V.S. et al. (1978). "Novel Influenza A Viruses Isolated From Canadian Feral Ducks: Including Strains Antigenically Related to Swine Influenza (HswIN1) Viruses," *J. Gen. Virol.* 41:115-127.
Jayaraman, K. et al. (May 1991). "Polymerase chain Reaction-Mediated Gene Synthesis: Synthesis of a Gene Coding for Isozyme C of Horseradish Peroxidase," *Proc. Natl. Acad. Sci. USA* 88:4084-4088.
Kaiser, R. et al. (Mar./Apr. 2000). "Laboratory Findings in Tick-Borne Encephalitis—Correlation With Clinical Outcome," *Infection* 28(2):78-84.
Kunkel, T.A. (Jan. 1985). "Rapid and Efficient Site-Specific Mutagenesis Without Phenotypic Selection," *Proc. Natl. Acad. Sci. USA* 82:488-492.
Lalvani, A. et al. (Sep. 15, 1997). "Rapid Effector Function in $CD8^+$ Memory T Cells," *J. Exp. Med.* 186(6):859-865.
Lin, Y.P. et al. (1997). "Adaptation of Egg-Grown and Transfectant Influenza Viruses for Growth in Mammalian Cells: Selection of Hemagglutinin Mutants With Elevated pH of Membrane Fusion," *Virology* 233:402-410.
Luytjes, W. et al. (Dec. 22, 1989). "Amplification, Expression, and Packaging of a Foreign Gene by Influenza Virus," *Cell* 59:1107-1113.
Macken, C. et al. (2001). "The Value of a Database in Surveillance and Vaccine Selection," *International Congress Series* 1219:103-106.
McHeyzer-Williams, M.G. et al. (Apr. 1996). "Enumeration and Characterization of Memory Cells in the $T_H$ Compartment," *Immunol. Rev.* 150(1):5-21.
McMichael, a.J. et al. (May 4, 1998). "A New Look at T Cells," *J. Exp. Med.* 187(9):1367-1371.
Mochalova, L. et al. (2003). "Receptor-Binding Properties of Modern Human Influenza Viruses Primarily Isolated in Vero and MDCK cells and Chicken Embryonated Eggs," *Virology* 313:473-480.

(56) References Cited

OTHER PUBLICATIONS

Montefiori, D.C. et al. (Feb. 1988). "Evaluation of Antiviral Drugs and Neutralizing Antibodies to Human Immunodeficiency Virus by a Rapid and Sensitive Microtiter Infection Assay," *J. Clin. Microbiol.* 26(2):231-235.
Queen, C. et al. (Dec. 1989). "A Humanized Antibody That Binds to the Interleukin 2 Receptor," *Proc. Natl. Acad. Sci. USA* 86:10029-10033.
Quinlivan, M. et al. (Jul. 2005). "Attenuation of Equine Influenza Viruses Through Truncations of the NS1 Protein," *J. Virol.* 79(13):8431-8439.
Riechmann, L. et al. (1988). "Reshaping Human Antibodies for Therapy," *Nature* 332:323-327.
Scholtissek, C. (Aug. 1994). "Source for Influenza Pandemics," *Eur. J. Epidemiol.* 10(4):455-458.
Shin, Y.-K. et al. (2007). "Effect of the Phosphatidylinositol 3-Kinase/Akt Pathway on Influenza A Virus Propagation," *J. Gen. Virol.* 88:942-950.
Smith, T.F. et al. (1981). "Comparison of Biosequences," *Advances in Appl. Math.* 2:482-489.
Subbarao, E.K. et al. (Dec. 1993). "Rescue of an Influenza a Virus Wild-Type PB2 Gene and a Mutant Derivative Bearing a Site-Specific Temperature-Sensitive and Attenuating Mutation," *J. Virol.* 67(12):7223-7228.
Subekti, D.S. et al. (Mar. 2002). "Experimental Infection of *Macaca nemestrina* With a Toronto Norwalk-Like Virus of Epidemic Viral Gastroenteritis," *J. Med. Virol.* 66(3):400-406.
Verhoeyen, M. et al. (Mar. 25, 1988). "Reshaping Human Antibodies: Grafting an Antilysozyme Activity," *Science* 239(4847):1534-1536.
Watanabe, T. et al. (Oct. 2003). "Exploitation of Nucleic Acid Packaging Signals to Generate a Novel Influenza Virus-Based Vector Stably Expressing Two Foreign Genes," *J. Virol.* 77(19):10575-10583.
Wobus, C.E. et al. (Nov. 30, 2004). "Replication of *Norovirus* in Cell Culture Reveals a Tropism for Dendritic Cells and Macrophages," *PLOS Biology* 2:e432, 9 pages.
Zoller, M.J. et al. (1983). "[32] Oligonucleotide-Directed Mutagenesis of DNA Fragments Cloned Into M13 Vectors," *Methods Enzymol.* 100:468-500.
Final Office Action for U.S. Appl. No. 13/559,940, dated Dec. 16, 2014, filed Jul. 27, 2012, 11 pages.
Non-Final Office Action for U.S. Appl. No. 13/559,940, dated Jan. 24, 2014, filed Jul. 27, 2012, 9 pages.
Non-Final Office Action for U.S. Appl. No. 13/559,940, dated Feb. 3, 2016, filed Jul. 27, 2012, 9 pages.

* cited by examiner

Influenza A virus (A/swine/Saskatchewan/18789/02(H1N1))
hemagglutinin (HA) gene

GenBank: AY619961.1 (SEQ ID NOS:1 and 2)

```
   1 atggaagcaa aactgttcgt actattctgt acattcactg tactgaaagc tgacactatc
  61 tgtgtgggct accatgcaaa caactctaca aacactgttg atacagtact ggaaaagaac
 121 ataactgtga ctcactcagt gaatttgctc gaagacagcc ataatgggaa gctctgcagt
 181 ctgaatggga tagctccttt acaattgggg aagtgtaatg tagcgggatg gctcctgggc
 241 aacccagaat gtgaccttct actcactgca aactcatggt cctatataat agagacgtcc
 301 aattcagaga acgggacatg ctatcctggt gagttcatag attatgagga attaagggag
 361 caattgagtt cggtttcttc atttgaaaag tttgaaattt tccccaaggc aaactcatgg
 421 ccaaaccatg agacaactaa aggtgttaca gctgcctgct cttactctgg ggccagcagt
 481 ttttaccgaa atttgctgtg gataacaaag aagggaactt catatccaaa actcagcaag
 541 tcatacacga acaataaagg gaaagaagtg cttgtgctct ggggagtgca ccatcctccg
 601 accaccagtg atcaacagag tatataccag aacactgatg catacgtctc agttgggtca
 661 tcaaagtaca accgaagatt cactccagag atagcagcta gacccaaagt tagaggacag
 721 gcaggcagga tgaactatta ttggacacta ctagaccaag gagacaccat aacatttgag
 781 gccactggga atctgatagc accatggtat gccttcgcac taaataaggg gtcagactca
 841 gggattataa catcagatgc tccagttcac aattgcgaca caaggtgcca aacccctcac
 901 ggggcgttga acagtagcct ccctttcag aatgtgcatc ctatcaccat tggagaatgt
 961 cccaaatatg tcaagagcac caagctaaga atggcaacag gactaagaaa tgtcccatcc
1021 attcaatcca gaggactgtt tggagcaatt gccggattca ttgagggagg atggacaggc
1081 atgatagatg ggtggtatgg gtaccaccac cagaatgagc aaggatcagg gtatgccgct
1141 gatcagaaaa gcacacagaa tgcaatcgac ggaataacta acaaggtgaa ttcggtaatt
1201 gagaaaatga acactcaatt cactgcagtg ggtaaggaat tcaacaatct agagaggaga
1261 attgaaaatc tgaataggaa agtcgatgat gggttcctgg atgtttggac atacaatgct
1321 gaactgctcg ttctactgga gaatgaaaga actctggact ttcatgattc caatgtgagg
1381 aatttgtatg aaaaggtcag atcacaactg aggaataacg ccaaagaact tggaaatggt
1441 tgctttgagt tctatcacaa gtgtgatgat gaatgcatgg aaagtgtgaa gaacggcaca
1501 tatgactatc ccaaatattc agaagagtct aaattgaatc gggaagaaat agacggagtg
1561 agactagaat cgatgggagt ttaccaaatt ttggcgatct attccacagt cgccagttct
1621 ctagtcttgt tagtctccct gggggcaatc agcttctgga tgtgttctaa tgggtcattg
1681 caatgcagaa tatgcattta g
```

FIGURE 5A

```
MEAKLFVLFCTFTVLKADTICVGYHANNSTNTVDTVLEKNITVT
HSVNLLEDSHNGKLCSLNGIAPLQLGKCNVAGWLLGNPECDLLLTANSWSYIIETSNS
ENGTCYPGEFIDYEELREQLSSVSSFEKFEIFPKANSWPNHETTKGVTAACSYSGASS
FYRNLLWITKKGTSYPKLSKSYTNNKGKEVLVLWGVHHPPTTSDQQSIYQNTDAYVSV
GSSKYNRRFTPEIAARPKVRGQAGRMNYYWTLLDQGDTITFEATGNLIAPWYAFALNK
GSDSGIITSDAPVHNCDTRCQTPHGALNSSLPFQNVHPITIGECPKYVKSTKLRMATG
LRNVPSIQSRGLFGAIAGFIEGGWTGMIDGWYGYHHQNEQGSGYAADQKSTQNAIDGI
TNKVNSVIEKMNTQFTAVGKEFNNLERRIENLNRKVDDGFLDVWTYNAELLVLLENER
TLDFHDSNVRNLYEKVRSQLRNNAKELGNGCFEFYHKCDDECMESVKNGTYDYPKYSE
ESKLNREEIDGVRLESMGVYQILAIYSTVASSLVLLVSLGAISFWMCSNGSLQCRICI
```

FIGURE 5B

Influenza A virus (A/swine/Saskatchewan/18789/02(H1N1)) neuraminidase (NA) gene

GenBank: AY619960.1 (SEQ ID NOS:3 and 4)

```
   1 atgaatccaa atcaaaagat aataactatt gggtcaatct gcatggcaat tggagtaata
  61 agtctggtgt tacaaattgg aaatataatc tcaatatggg ttaaccattc aattcaaact
 121 ggaagtcaga accaccccga aacatgcaat caaagtgtca ttacctacga aaacaatact
 181 tgggtgaatc aaacatacat caacataagc aataccaatt taattgcaga acaagctgta
 241 gctccagtaa cactagcagg caattcctct ctctgtccca tcagtgggtg ggctatatac
 301 agcaaggata atggtataag gataggttcg aagggagatg tatttgtcat cagagagcct
 361 tttatttcat gctctcactt ggagtgcagg gctttctttc taactcaagg ggccttgttg
 421 aatgacaagc attccaacgg aaccgttaaa gacagaagcc cttatagaac cctaatgagc
 481 tgtcctgttg gcgaagctcc ttctccatac aattcaaggt ttgagtctgt tgcttggtca
 541 gcaagtgctt gtcatgatgg cattagttgg ttgacaattg gtatttccgg cccagacaat
 601 ggggcggtgg ctgtattgaa atacaatggc ataataacag atactgttaa gagttggaga
 661 aacaatatat tgagaacaca agagtctgaa tgtgcctgca ttaacggttc ctgctttacc
 721 ataatgactg atgggccaag taatggccag gcctcataca agattttcaa gatagaaaag
 781 gggaaggtag tcaaatcagt tgagttgaat gcccctaatt accactacga ggagtgctcc
 841 tgttatcctg atgctagtga ggtaatgtgt gtatgcagag acaactggca tggttcaaac
 901 cgaccatggg tgtccttcaa tcagaatcta gagtaccaaa taggatacat atgcagcgga
 961 gtttttggag acaacccacg ccccaatgat ggaacaggca gttgtggtcc agtgtcttct
1021 aatggggcat atggagtaaa ggggttttca tttaaatacg gtaatggtgt ttggatagga
1081 agaactaaaa gtactagctc aaggagtggg tttgagatga tttgggatcc caatgggtgg
1141 acagagacag acaacagttt ctctgtgaaa caagatattg tagcaataac tgattggtca
1201 ggatatagcg gaagttttgt tcagcatcca gaattaacgg ggctggactg catgaggcct
1261 tgcttctggg ttgagctgat cagaggaaga cccaaggaga atacaatctg gaccagtggg
1321 agcagcattt ccttttgtgg agtaaatagc gacactgtgg gttggtcttg gccagacggt
1381 gctgagttgc cattcaccat tgacaagtag
```

FIGURE 6A

```
MNPNQKIITIGSICMAIGVISLVLQIGNIISIWVNHSIQTGSQN
HPETCNQSVITYENNTWVNQTYINISNTNLIAEQAVAPVTLAGNSSLCPISGWAIYSK
DNGIRIGSKGDVFVIREPFISCSHLECRAFFLTQGALLNDKHSNGTVKDRSPYRTLMS
CPVGEAPSPYNSRFESVAWSASACHDGISWLTIGISGPDNGAVAVLKYNGIITDTVKS
WRNNILRTQESECACINGSCFTIMTDGPSNGQASYKIFKIEKGKVVKSVELNAPNYHY
EECSCYPDASEVMCVCRDNWHGSNRPWVSFNQNLEYQIGYICSGVFGDNPRPNDGTGS
CGPVSSNGAYGVKGFSFKYGNGVWIGRTKSTSSRSGFEMIWDPNGWTETDNSFSVKQD
IVAITDWSGYSGSFVQHPELTGLDCMRPCFWVELIRGRPKENTIWTSGSSISFCGVNS
DTVGWSWPDGAELPFTIDK
```

FIGURE 6B

Influenza A virus (A/swine/Saskatchewan/18789/02(H1N1))
matrix protein 2 (M2) and matrix protein 1 (M1) genes GenBank: AY619959.1 (SEQ ID NOS:5, 6 and 7)

```
  1 atgagtcttc taaccgaggt cgaaacgtac gttctctcta tcgtcccgtc aggccccctc
 61 aaagccgaga tcgcgcagag acttgaagat gtctttgcag ggaagaacac cgatcttgag
121 gcactcatgg aatggctaaa gacaagacca atcctgtcac ctctgactaa ggggatttta
181 ggatttgtgt ttacactcac cgtgcccagt gagcgaggac tgcagcgtag acgctttgtc
241 caaaatgccc ttaatgggaa tggggatcca aacaacatgg acagagcagt caaactgtac
301 aggaaactaa aaagggaaat aacattccat ggggcaaaag aggtggcact cagttattcg
361 actggtgcac ttgccagttg catgggcctc atatacaaca gaatggggac tgtgaccact
421 gaagtggcat ttggcctagt ttgcgccaca tgtgagcaga ttgctgactc ccagcatcgg
481 tctcacagac agatggtaac aacaaccaac ccactgatca gacatgagaa cagaatggta
541 ctagccagta ccacggctaa ggccatggaa caaatggcag ggtcaagtga gcaggctgca
601 gaggctatgg aggttgctaa tcaagctaga caaatggtgc aggcaatgag gaccattggg
661 actcatccta gctccagtgc cggtctaaaa gatgatcttc ttgaaaattt gcaggcctac
721 cagaaacgga tgggagtgca aatgcagcga ttcaagtgat cctcttgtta ttgccgcaag
781 tatcattggg atcttgcact tgatattgtg gattcttgat cgtcttttct tcaaatgcat
841 ttatcgtcgc cttaaatacg gtttgaaaag agggccttct acggaaggag tgcctgagtc
901 tatgagggaa gaatatcggc aggaacagca gagtgctgtg gatgttgacg atggtcattt
961 tgtcaacata gagctggagt aa
```

FIGURE 7A

M2:
MSLLTEVETPTRNGWECKCSDSSDPLVIAASIIGILHLILWILD
RLFFKCIYRRLKYGLKRGPSTEGVPESMREEYRQEQQSAVDVDDGHFVNIELE

FIGURE 7B

M1:
MSLLTEVETYVLSIVPSGPLKAEIAQRLEDVFAGKNTDLEALME
WLKTRPILSPLTKGILGFVFTLTVPSERGLQRRRFVQNALNGNGDPNNMDRAVKLYRK
LKREITFHGAKEVALSYSTGALASCMGLIYNRMGTVTTEVAFGLVCATCEQIADSQHR
SHRQMVTTTNPLIRHENRMVLASTTAKAMEQMAGSSEQAAEAMEVANQARQMVQAMRT
IGTHPSSSAGLKDDLLENLQAYQKRMGVQMQRFK

FIGURE 7C

Influenza A virus (A/swine/Saskatchewan/18789/02(H1N1)) nucleoprotein (NP) gene

GenBank: AY619958.1 (SEQ ID NOS:8 and 9)

```
   1 atggcgtctc aaggcaccaa acgatcttat gagcagatgg aaactggtgg agaacgccag
  61 aatgccactg aaatcagagc atctgttggg agaatggttg gtggaatcgg aagattctac
 121 atacagatgt gcactgaact caaactcagt gactatgaag ggagactgat ccaaaacagc
 181 atcacaatag agagaatggt tctctcagca tttgatgaga ggagaaacaa atatctggaa
 241 gagcatccca gtgctgggaa agaccctaag aagactggag gtccaatcta caggaggaga
 301 gatgggaaat ggatgagaga attgatccta tatgacaaag aggagatcag aaggatttgg
 361 cgtcaagcga ataatggaga agacgcaact gccggtctca cccatttgat gatctggcac
 421 tccaatctga atgatgccac ctatcagagg acgagggcac ttgtgcgtac tggaatggat
 481 cccaggatgt gttctctgat gcaaggctcg actctcccga ggaggtctgg agctgctgga
 541 gcagctgtga aggagttgg aacaatggtg atggaattga tccgaatgat caagcgaggg
 601 atcaatgatc ggaatttctg gagaggcgaa aatgggcgga ggacaagaat tgcttatgaa
 661 agaatgtgca acatcctcaa agggaagttc caaacagcgg cacaacgagc aatgatggac
 721 caggtgaggg aaagccggaa tcctgggaat gctgaaattg aagatctcat ctttcttgca
 781 cggtctgctc tcattctgag gggatcagtg gctcataagt cttgcctgcc tgcttgtgtg
 841 tatggacttg ctgtggccag tggatacgac tttgaaaggg agggatactc cctagttgga
 901 attgatcctt tccgtctgct ccaaaacagt caagtcttca gtcttatcag accaaacgaa
 961 aatccagcac ataaaagcca gctggtatgg atggcatgcc actctgcagc ttttgaagat
1021 cttagagtgt caagcttcat tagaggaaca agagtagtcc caagaggaca actgtccacc
1081 agaggagttc agattgcttc aaatgagaac atggagacaa tggactccag tactcttgaa
1141 ctgaggagca gatactgggc tataaggacc agaagtgggg ggaacactaa ccagcagaga
1201 gcatccgcag ggcaaatcag cgtacagccc acattctctg tacagaggaa cctcccattc
1261 gagagagcaa ccattatggc ggcatttaca ggaaacactg aaggcagaac ttcagacatg
1321 agaacagaaa tcataaggat gatggaaaat gccagacctg aagatgtgtc tttccagggg
1381 cggggagtct tcgagctctc ggacgaaaag gcaacgaacc cgatcgtgcc ttcctttgac
1441 atgagcaacg aaggatctta tttcttcgga gacaatgcag aggaatatga caattaa
```

FIGURE 8A

```
MASQGTKRSYEQMETGGERQNATEIRASVGRMVGGIGRFYIQMC
TELKLSDYEGRLIQNSITIERMVLSAFDERRNKYLEEHPSAGKDPKKTGGPIYRRRDG
KWMRELILYDKEEIRRIWRQANNGEDATAGLTHLMIWHSNLNDATYQRTRALVRTGMD
PRMCSLMQGSTLPRRSGAAGAAVKGVGTMVMELIRMIKRGINDRNFWRGENGRRTRIA
YERMCNILKGKFQTAAQRAMMDQVRESRNPGNAEIEDLIFLARSALILRGSVAHKSCL
PACVYGLAVASGYDFEREGYSLVGIDPFRLLQNSQVFSLIRPNENPAHKSQLVWMACH
SAAFEDLRVSSFIRGTRVVPRGQLSTRGVQIASNENMETMDSSTLELRSRYWAIRTRS
GGNTNQQRASAGQISVQPTFSVQRNLPFERATIMAAFTGNTEGRTSDMRTEIIRMMEN
ARPEDVSFQGRGVFELSDEKATNPIVPSFDMSNEGSYFFGDNAEEYDN
```

FIGURE 8B

Influenza A virus (A/swine/Saskatchewan/18789/02(H1N1)) nonstructural protein 2 (NS2, also termed NEP) and nonstructural protein 1 (NS1) genes GenBank: AY619957.1 (SEQ ID NOS:10, 11 and 12)

```
  1 atggactcca acacgataac ctcgttccag gtagattgct atctatggca cataagaaag
 61 ctgctcagca tgagagacat gtgtgatgct ccctttgatg atagactcag aagagatcaa
121 aaggcattaa agggaagagg cagcacactt ggactcgacc tgcgagtggc cacaatggaa
181 ggcaaaaaga ttgttgaaga catcctaaag agtgaaatgg atgaaaatct caaaattgca
241 attgcatcca gccctgctcc tcggtacatt accgatatga gcatagagga aataagcagg
301 gaatggtaca tgctcatgcc aaggcagaaa ataactgggg gtctgatggt gaaaatggat
361 caggccatta tggacaagag gataatactc aaggcgaact tctctgtcct ttttgatcaa
421 ctggagacat tagtctcact gagggctttc acagacaatg gcgccattgt agctgaaata
481 tctcccattc cttccatgcc aggacattct acagaggatg tcaaaaatgc aattggaatc
541 ctcatcggcg gacttgaatg gaatgataac tcaattcgag cgtctgaaaa tatacagaga
601 ttcgcttggg gagtccgtga tgagaatggg ggacctccac tccctccaaa gcagaaacgc
661 tacatggcga gaagagttga gtcagaagtt tgaagaaatc agatggctaa ttgcagagtg
721 cagaaacata ttaaccaaaa ctgagaacag cttcgagcag ataacgttct tgcaagcatt
781 gcaactctta cttgaagtcg agagtgagat aaggacattt tcttttcagc ttatttag
```

FIGURE 9A

NS2:
MDSNTITSFQDILQRMSKMQLESSSADLNGMITQFERLKIYRDS
LGESVMRMGDLHSLQSRNATWREELSQKFEEIRWLIAECRNILTKTENSFEQITFLQA
LQLLLEVESEIRTFSFQLI

FIGURE 9B

NS1:
MDSNTITSFQVDCYLWHIRKLLSMRDMCDAPFDDRLRRDQKALK
GRGSTLGLDLRVATMEGKKIVEDILKSEMDENLKIAIASSPAPRYITDMSIEEISREW
YMLMPRQKITGGLMVKMDQAIMDKRIILKANFSVLFDQLETLVSLRAFTDNGAIVAEI
SPIPSMPGHSTEDVKNAIGILIGGLEWNDNSIRASENIQRFAWGVRDENGGPPLPPKQ
KRYMARRVESEV

FIGURE 9C

Influenza A virus (A/swine/Saskatchewan/18789/02(H1N1)) polymerase acidic protein 2 (PA) gene

GenBank: AY619956 (SEQ ID NOS:13 and 14)

```
   1 atggaagact ttgtgcgaca atgcttcaat ccaatgatcg tcgagcttgc ggaaaaggca
  61 atgaaggaat atggggaaga cccaaaaatc gagactaaca aattcgctgc aatatgcact
 121 cacttggaag tatgtttcat gtattcggat ttccacttca ttgatgaacg ggcgaatca
 181 ataattgtgg aatctggtga tccaaatgca ttactgaagc accgatttga aataattgaa
 241 ggaagggacc gaacaatggc ctggacagtg gtgaatagca tctgcaacac cacaggagtc
 301 gagaagccta aatttctccc ggatctgtat gattacaagg agaaccgatt cattgaaatt
 361 ggagtgacac ggagagaggt ccatatatac tacctagaga aagccaacaa gataaaatcc
 421 gagaagacac acattcacat cttttcattt actggagaag aaatggccac caaagcagac
 481 tacactcttg atgaagaaag cagggcaaga atcaaaacca ggctgttcac tataagacaa
 541 gaaatggcca gcaggggcct atgggattcc tttcgtcagt ccgaaagagg cgaagagaca
 601 actgaagaaa gatttgaaat cacaggaacc atgcgtaggc ttgccgacca aagtctccca
 661 ccgaacttct ccagccttga aaactttaga gcctatgtgg atggattcga accgaacggc
 721 tgcattgagg gcaagctttc tcaaatgtca aaagaagtga acgccaggat cgagccattc
 781 ctgaagacaa caccacgccc tctcaaatta cctgatgggc ccccttgctc ccagcggtcg
 841 aaattcttgc tgatggatgc cttgaaacta agcatcgaag atccaagtca cgagggagag
 901 gggataccac tatacgatgc aatcaaatgt atgaagacat tttcggctg gaaagagccc
 961 aatataatca aaccacatga gaaaggcata aatcccaatt accttctggc ttggaagcaa
1021 gtgctggcag aacttcagga ccttgaaaat gaagagaaaa tcccaaagac aaagaacatg
1081 aagaagacaa gccaattgaa gtgggcactt ggtgagaaca tggcaccaga gaaagtggac
1141 tttgaggatt gcaaggacat tggcgatctg aaacaatatg atagtgatga gccagagcct
1201 agatcgctag caagctggat ccagaacgaa ttcaataagg cgtgtgaatt gaccgactcg
1261 agctggatag aacttgatga aataggagaa gatgttgctc cgattgaaca cattgcaagt
1321 ataaggagga actattttac agcagaagtg tcccactgca gggccactga atacataatg
1381 aagggagtct acataaacac agctctgctc aatgcatctt gtgcagccat ggacgacttc
1441 cagctgattc caatgataag caaatgtaga acaaaggaag gaagacggaa aaccaacctg
1501 tatggattca tcataaaagg aagatcccat ttgaggaatg atactgatgt ggtaaacttt
1561 gtgagcatgg aattttctct cactgacccg aggctagaac cccacaaatg ggaaaagtac
1621 tgtgttcttg aaataggaga tatgctcctg aggactgcaa taggccaagt gtctaggccc
1681 atgttcctgt acgttagaac caatgggacc tctaagatca agatgaaatg ggtatggaa
1741 atgagacgct gcctccttca atctcttcaa cagattgaga gcatgattga ggccgagtct
1801 tctgtcaaag aaaaggacat gactaaggaa ttctttgaaa ataagccgga aaagtggcca
1861 attggagaat cccccagagg agtagaggaa ggctctatcg ggaaagtatg cagaacctta
1921 ctggcaaaat ctgtattcaa cagtctatat gcatctccac aacttgaggg attttcagct
1981 gaatcgagga aattgcttct cattgttcag gcacttaggg acaacctgga acctggaacc
2041 tttgatcttg gggggctata tgaagcaatt gaggagtgcc tgattaatga tccctgggtt
2101 ttgcttaatg catcttggtt caactccttc ctcacacatg cactgaaata g
```

FIGURE 10A

```
MEDFVRQCFNPMIVELAEKAMKEYGEDPKIETNKFAAICTHLEV
CFMYSDFHFIDERGESIIVESGDPNALLKHRFEIIEGRDRTMAWTVVNSICNTTGVEK
PKFLPDLYDYKENRFIEIGVTRREVHIYYLEKANKIKSEKTHIHIFSFTGEEMATKAD
YTLDEESRARIKTRLFTIRQEMASRGLWDSFRQSERGEETTEERFEITGTMRRLADQS
LPPNFSSLENFRAYVDGFEPNGCIEGKLSQMSKEVNARIEPFLKTTPRPLKLPDGPPC
SQRSKFLLMDALKLSIEDPSHEGEGIPLYDAIKCMKTFFGWKEPNIIKPHEKGINPNY
LLAWKQVLAELQDLENEEKIPKTKNMKKTSQLKWALGENMAPEKVDFEDCKDIGDLKQ
YDSDEPEPRSLASWIQNEFNKACELTDSSWIELDEIGEDVAPIEHIASIRRNYFTAEV
SHCRATEYIMKGVYINTALLNASCAAMDDFQLIPMISKCRTKEGRRKTNLYGFIIKGR
SHLRNDTDVVNFVSMEFSLTDPRLEPHKWEKYCVLEIGDMLLRTAIGQVSRPMFLYVR
TNGTSKIKMKWGMEMRRCLLQSLQQIESMIEAESSVKEKDMTKEFFENKPEKWPIGES
PRGVEEGSIGKVCRTLLAKSVFNSLYASPQLEGFSAESRKLLLIVQALRDNLEPGTFD
LGGLYEAIEECLINDPWVLLNASWFNSFLTHALK
```

FIGURE 10B

Influenza A virus (A/swine/Saskatchewan/18789/02(H1N1)) polymerase subunit PB1 (PB1) gene
GenBank: AY619955.1 (SEQ ID NOS:15 and 16)

```
   1 atggatgtca atccgacttt acttttcttg aaagttccag cgcaaaatgc cataagcacc
  61 acattcccat atactggaga tcctccctac agccatggaa cgggaacggg atacaccatg
 121 gacacagtca acaggacaca tcaatactca gaaaagggga aatggacaac aaacacagag
 181 actggagcac cccaacttaa cccgattgac ggaccattac ctgaggataa tgaaccaagt
 241 ggatatgcac aaacagactg cgtcctggaa gcaatggctt tccttgaaga atcccaccca
 301 ggaatctttg aaaactcgtg tcttgaaacg atggaagttg ttcaacaaac aagagtggac
 361 aagctgaccc aaggtcgcca gacctatgat tggacattaa acaggaatca gccagctgca
 421 actgcattag ccaatactat agaggtcttc agatcgaacg gtttaacagc taatgaatcg
 481 ggaaggctaa tcgatttcct caaggatgtg atggaatcaa tggataaaga ggaaatggaa
 541 ataacaacgc acttccaaag aaaaagaagg gtgagagaca acatgaccaa gaaaatggtc
 601 acacaaagaa caataggaaa gaagaagcag agattaaaca agagaagcta tctaataaga
 661 gcattgacat taaacacaat gacaaaagat gctgaaagag gcaaattaaa gagaagagca
 721 attgcaacac ccgggatgca aatcagagga tttgtgtatt ttgttgaaac actagcaagg
 781 agcatttgtg agaagctcga gcaatctgga cttccagttg gaggcaatga aaagaaggct
 841 aaactggcaa atgtcgtgag aaagatgatg actaattcac aagacacaga gctctctttc
 901 acaatcactg gagacaacac caaatggaat gaaaatcaaa accctcgaat gttcctggca
 961 atgataacat acataacaag aaatcaacct gaatggttta gaaatgtttt gagcattgca
1021 cctataatgt tctcgaataa aatggcaaga ctaggaaaag gatacatgtt cgaaagtaag
1081 agcatgaagc ttcgaacaca gataccggca gaaatgctag caagtattga tctgaaatat
1141 ttcaacgaat caacaagaaa gaaaatcgag aagataagac ctcttctaat agatggtaca
1201 gcctcattga gccctggaat gatgatgggc atgttcaaca tgctaagtac agttttggga
1261 gtctcaattc tgaatctagg gcaaaagaga tacaccaaaa caacatactg gtgggacgga
1321 ctccaatcct ctgatgactt tgctctcata gtgaatgctc cgaatcatga gggtatacaa
1381 gcaggagtag atagattcta tagaacctgc aagctggtcg gaatcaacat gagcaaaaag
1441 aagtcctaca taaacagaac agggacattt gaattcacaa gctttttcta tcgctatgga
1501 tttgtagcca actttagcat ggagctgccc agctttggag tgtctgggat caatgaatct
1561 gccgacatga gcattggagt aacagtgata aagaacaaca tgataaacaa tgatcttgga
1621 ccagcaacag ctcaaatggc tcttcagctg ttcatcaagg attacagata cacatatcgg
1681 tgtcacagag ggacacacaa aattcagaca aggaggtcat tcgagctgaa aaaactgtgg
1741 gaacaaaccc gctcaaaggc aggactgctg gtttcagatg gaggaccaaa cttatacaat
1801 atccggaatc tccacattcc ggaagtctgc ctgaaatggg agctaatgga tgaagactat
1861 cagggaaggc tttgtaatcc cctgaatcca tttgtcagcc acaaagagat agagtctgta
1921 aacaatgctg tggtgatgcc agctcatgga ccagccaaga gcatggaata tgatgctgtt
1981 gctactacac actcctggat tcctaagagg aaccgctcca ttctcaacac aagtcaaagg
2041 ggaatccttg aagatgaaca gatgtaccaa aagtgctgca atctattcga gaaattcttc
2101 cctagcagct catacaggag accagttggg atttccagca tggtggaggc catggtttct
2161 agggcccgaa ttgatgcgcg aattgacttc gaatctggac ggattaagaa ggaggaattt
2221 gctgagatca tgaagatctg ttccaccatt gaagagctca gacggcagaa atag
```

FIGURE 11A

```
MDVNPTLLFLKVPAQNAISTTFPYTGDPPYSHGTGTGYTMDTVN
RTHQYSEKGKWTTNTETGAPQLNPIDGPLPEDNEPSGYAQTDCVLEAMAFLEESHPGI
FENSCLETMEVVQQTRVDKLTQGRQTYDWTLNRNQPAATALANTIEVFRSNGLTANES
GRLIDFLKDVMESMDKEEMEITTHFQRKRRVRDNMTKKMVTQRTIGKKKQRLNKRSYL
IRALTLNTMTKDAERGKLKRRAIATPGMQIRGFVYFVETLARSICEKLEQSGLPVGGN
EKKAKLANVVRKMMTNSQDTELSFTITGDNTKWNENQNPRMFLAMITYITRNQPEWFR
NVLSIAPIMFSNKMARLGKGYMFESKSMKLRTQIPAEMLASIDLKYFNESTRKKIEKI
RPLLIDGTASLSPGMMMGMFNMLSTVLGVSILNLGQKRYTKTTYWWDGLQSSDDFALI
VNAPNHEGIQAGVDRFYRTCKLVGINMSKKKSYINRTGTFEFTSFFYRYGFVANFSME
LPSFGVSGINESADMSIGVTVIKNNMINNDLGPATAQMALQLFIKDYRYTYRCHRGDT
QIQTRRSFELKKLWEQTRSKAGLLVSDGGPNLYNIRNLHIPEVCLKWELMDEDYQGRL
CNPLNPFVSHKEIESVNNAVVMPAHGPAKSMEYDAVATTHSWIPKRNRSILNTSQRGI
LEDEQMYQKCCNLFEKFFPSSSYRRPVGISSMVEAMVSRARIDARIDFESGRIKKEEF
AEIMKICSTIEELRRQK
```

FIGURE 11B

Influenza A virus (A/swine/Saskatchewan/18789/02(H1N1)) polymerase subunit PB2 (PB2) gene GenBank: AY619954.1 (SEQ ID NOS:17 and 18)

```
   1 atggagagaa taaaagaact aagagatcta atgtcacagt ctcgcactcg cgagatactc
  61 accaaaacca ctgtggacca catggccata atcaaaaagt acacatcagg aaggcaagag
 121 aagaaccctg cactcaggat gaagtggatg atggcaatga aatatccaat tgcagcagac
 181 aagagaataa tggagatgat tcctgaaagg aatgaacagg gacaaaccct ttggagcaaa
 241 gcaaatgatg ccggctcaga ccgagtgatg gtatctcctc tggctgtgac atggtggaat
 301 aggaatggac caacaactag tacagttcat tatccaaagg tgtataagac ttatttcgaa
 361 aaagtcgaaa ggttgaaaca cgggaccttt ggccctgttc gcttcagaaa tcaagttaaa
 421 ataagacgga tggttgacat aaaccctggt cacgcaggcc tcagtgccaa agaggcacag
 481 gatgtaataa tggaagtcgt tttcccaaat gaagtgggag cgagaatact aacatcggag
 541 tcacaactga cgataccaaa agaaaagaag gaagaactcc aggactgcaa gattgcccct
 601 ttgatggttg catacatgct agaaagggaa ttggtccgta aaactaggtt cctcccagtg
 661 gctggtggaa caagcagtgt ctacattgag gtgctgcatt taactcaggg gacatgctgg
 721 gagcaaatgt acaccccagg aggggaagtg aggaatgatg atgttgacca aagcttgatt
 781 atcgctgcca ggaacatagt aagaagagca acagtatcag cagacccact agcatctcta
 841 ttggagatgt gtcacagcac acagattgga gggataagga tggtagacat tcttcggcaa
 901 aatccgacag aggaacaagc tgtggacata tgcaaggcag caatgggctt aaggattagc
 961 tcatctttca gctttggcgg attcactttc aaaagaacaa gcgggtcgtc agttaagaga
1021 gaagaagaaa tgcttacggg caaccttcaa acattgaaaa taagagtaca tgaggggtat
1081 gaagagttca caatggttgg gagaagagca acagccattc tcaggaaggc aaccagaaga
1141 ttgatccagc taatagtaag tgggagagac gagcagtcaa ttgctgaagc aataattgtg
1201 gccatggtat tctcacaaga ggattgcatg atcaaggcag tccgaggtga tttgaacttt
1261 gtcaatagag caaaccagcg gctaaaccca atgcatcaac tcttgagaca cttccaaaag
1321 gacgcaaaag tgcttctcca aaactgggga attgaaccca ttgacaatgt aatgggaatg
1381 atcgggatat tacccgacat gactccaagt actgagatgt cgctgagggg gataagagtc
1441 agtaagatgg gagtagatga atactccagc acagagagag tggtagtgag cattgaccga
1501 tttttaagag tccgggacca acgagggaat gtgctattgt cgcctgaaga agtcagcgag
1561 acacaaggaa cagagaagct gacaataact tattcgtcgt caatgatgtg ggagatcaat
1621 ggccctgaat cggttttggt caacacttat cagtggatca tcagaaattg ggaaactgtg
1681 aaaattcaat ggtcacaaga ccccacgatg ttatataaca agatggaatt cgagccattc
1741 cagtctctgg tccctaaagc agccagaggt cagtacagtg gattcgtgag gacacttttc
1801 caacagatgc gggatgtgct tggaactttc gacactgttc agataataaa acttctcccc
1861 tttgctgctg ctccaccaga acaaagtagg atgcaattct cctccttgac tgtgaatgtg
1921 aggggatcag gaatgagaat actagtaagg ggcaattctc cagtgttcaa ttacaataag
1981 gccactaaga ggcttacagt tctcggaaaa gatgcaggtg cattgatcga agatccagac
2041 gaaggcacag ctggagtaga gtctgctgtt ttgagaggat tcctcatctt gggcaaagaa
2101 gacaagagat atggcccagc attgagcatc aatgagctga gcaatcttgc aaaaggagag
2161 aaggctaatg tgctaattgg gcaaggagac gtggtgttgg taatgaaacg gaaacgggac
2221 tctagcatac ttactgacag tcagacagcg accaaaagaa ttcggatggc catcaattag
```

FIGURE 12A

```
MERIKELRDLMSQSRTREILTKTTVDHMAIIKKYTSGRQEKNPA
LRMKWMMAMKYPIAADKRIMEMIPERNEQGQTLWSKANDAGSDRVMVSPLAVTWWNRN
GPTTSTVHYPKVYKTYFEKVERLKHGTFGPVRFRNQVKIRRMVDINPGHAGLSAKEAQ
DVIMEVVFPNEVGARILTSESQLTIPKEKKEELQDCKIAPLMVAYMLERELVRKTRFL
PVAGGTSSVYIEVLHLTQGTCWEQMYTPGGEVRNDDVDQSLIIAARNIVRRATVSADP
LASLLEMCHSTQIGGIRMVDILRQNPTEEQAVDICKAAMGLRISSSFSFGGFTFKRTS
GSSVKREEEMLTGNLQTLKIRVHEGYEEFTMVGRRATAILRKATRRLIQLIVSGRDEQ
SIAEAIIVAMVFSQEDCMIKAVRGDLNFVNRANQRLNPMHQLLRHFQKDAKVLLQNWG
IEPIDNVMGMIGILPDMTPSTEMSLRGIRVSKMGVDEYSSTERVVVSIDRFLRVRDQR
GNVLLSPEEVSETQGTEKLTITYSSSMMWEINGPESVLVNTYQWIIRNWETVKIQWSQ
DPTMLYNKMEFEPFQSLVPKAARGQYSGFVRTLFQQMRDVLGTFDTVQIIKLLPFAAA
PPEQSRMQFSSLTVNVRGSGMRILVRGNSPVFNYNKATKRLTVLGKDAGALIEDPDEG
TAGVESAVLRGFLILGKEDKRYGPALSINELSNLAKGEKANVLIGQGDVVLVMKRKRD
SSILTDSQTATKRIRMAIN
```

FIGURE 12B

Influenza A virus (A/Swine/Texas/4199-2/98 (H3N2))
hemagglutinin gene (SEQ ID NOS:19 and 20)

```
   1 AGCAAAAGCA GGGGATAATT CTATTAACCA TGAAGACTAT CATTGCTTTG AGCTACATTT
  61 TATGTCTGGT TTTCGCTCAA AAACTTCCCG GAAATGACAA CAGCACAGCA ACGCTGTGCC
 121 TGGGACACCA TGCAGTGCCA AACGGAACCC TAGTGAAAAC AATCACGAAT GATCAAATTG
 181 AAGTGACTAA TGCTACTGAG CTGGTTCAGA GTTCCTCAAC AGGTAGAATA TGCGACAGTC
 241 CTCACCGAAT CCTTGATGGA AAAAACTGCA CATTGATAGA TGCTCTACTG GGAGACCCTC
 301 ATTGCGATGG CTTTCAAAAT AAGGAATGGG ACCTTTTTAT TGAACGCAGC AAAGCTTACA
 361 GCAACTGTTA CCCTTATGAT GTGCCGGATT ATTCCTCCCT TAGGTCACTA GTTGCCTCAT
 421 CAGGCACCCT GGAGTTTACC AATGAAGACT TCAATTGGAC TGGGGTCGCT CAGGATGGGG
 481 GAAGCTATTC TTGCAAAAGG GGATCTGTTA AAAGTTTCTT TAGTAGATTG AATTGGTTAC
 541 ACAAATTAGA ATACAAATAT CCAGCACTGA ACGTGACTAT GCCAAACAAT GACAAATTTG
 601 ACAAATTGTA CATTTGGGGG GTTCACCACC CGAGCACGGA CAGTGAACAA ACCAGCCTGT
 661 ATGTTCAAGC AATAGGGAGA GTCACAGTCT CTACCAAAAG TAGCCAACAA ACTGTAATCC
 721 CGAACATCGG GTCCAGACCC TGGGTGAGGG GCATCTCCAG TAGAATAAGC ATCTATTGGA
 781 CAATAGTAAA ACCGGGAGAC ATACTTTTGA TTAGCAGCAC AGGGAATCTA ATTGCTCCTC
 841 GGGGTTACTT CAAAATACGA AATGGGAAAA GCTCAATAAT GAGGTCAGAT GCACCCATTG
 901 ACAACTGCTA TTCTGAATGC ATCACTCCAA ATGGAAGCAT TCCCAATGAC AAACCTTTTC
 961 AAAATGTAAA TAGGATCACA TATGGGGCCT GTCCCAAATA TGTTAAGCAA AAAACTCTGA
1021 AATTGGCAAC AGGGATGCGG AATGTACCAG AGAAACAAAC TAGAGGCATA TTCGGCGCAA
1081 TCGCAGGTTT CATAGAAAAT GGTTGGGAGG GAATGGTAGA CGGTTGGTAC GGTTTCAGGC
1141 ATCAAAATTC TGAGGGCACA GGACAAGCAG CAGATCTTAA AAGCACCCAA GCAGCAATCG
1201 ATCAAGTCAA CGGGAAATTG AATAGGTTAA TCGAGAAAAC GAACGAGAAA TTCCATCAAA
1261 TCGAAAAAGA ATTTTCAGAA GTAGAAGGGA GAATTCAGGA CCTCGAGAAA TATGTTGAAG
1321 ACACTAAAAT AGATCTCTGG TCTTACAACG CGGAGCTCCT TGTTGCCCTG GAGAATCAAC
1381 ATACAATTGA TCTAACTGAC TCAGAAATGA ACAAACTGTT TGAAAAAACA AGGAAGCAAC
1441 TGAGGGAAAA TGCTGAGGAC ATGGGCAATG GTTGCTTCAA AATATACCAC AAATGTGACA
1501 ATGCCTGCAT AGGGTCAATC AGAAATGGAA CTTATGACCA TGATGTATAC AGAGACGAAG
1561 CATTAAACAA CCGGTTCCAG ATCAAAGGTG TTGAGCTGAA ATCAGGATAC AAAGATTGGA
1621 TCCTATGGAT TTCCTTTGCC ATATCATGCT TTTTGCTTTG TGTTGTTTTG CTGGGGTTCA
1681 TCATGTGGGC CTGCCAAAAA GGCAACATTA GGTGCAACAT TTGCATTTGA GTGCATTAAT
1741 TAAAAACACC CTTGTTTCTA CT
```

FIGURE 13A

```
MKTIIALSYILCLVFAQKLPGNDNSTATLCLGHHAVPNGTLVKTITNDQI
EVTNATELVQSSSTGRICDSPHRILDGKNCTLIDALLGDPHCDGFQNKEW
DLFIERSKAYSNCYPYDVPDYSSLRSLVASSGTLEFTNEDFNWTGVAQDG
GSYSCKRGSVKSFFSRLNWLHKLEYKYPALNVTMPNNDKFDKLYIWGVHH
PSTDSEQTSLYVQAIGRVTVSTKSSQQTVIPNIGSRPWVRGISSRISIYW
TIVKPGDILLISSTGNLIAPRGYFKIRNGKSSIMRSDAPIDNCYSECITP
NGSIPNDKPFQNVNRITYGACPKYVKQKTLKLATGMRNVPEKQTRGIFGA
IAGFIENGWEGMVDGWYGFRHQNSEGTGQAADLKSTQAAIDQVNGKLNRL
IEKTNEKFHQIEKEFSEVEGRIQDLEKYVEDTKIDLWSYNAELLVALENQ
HTIDLTDSEMNKLFEKTRKQLRENAEDMGNGCFKIYHKCDNACIGSIRNG
TYDHDVYRDEALNNRFQIKGVELKSGYKDWILWISFAISCFLLCVVLLGF
IMWACQKGNIRCNICI
```

FIGURE 13B

Unvaccinated and no viral challenged pig

MEM vaccinated and SIV/SK02 challenged pig

SIV-606 vaccinated and SIV/SK02 challenged pig

MEM vaccinated and SIV/Tx98 challenged pig

SIV-606 vaccinated and SIV/Tx98 challenged pig

SEQUENCE LISTING

```
<160> NUMBER OF SEQ ID NOS: 30

<210> SEQ ID NO 1
<211> LENGTH: 1701
<212> TYPE: DNA
<213> ORGANISM: Influenza A virus
<220> FEATURE:
<221> NAME/KEY: misc_feature
<222> LOCATION: (1)..(1701)
<223> OTHER INFORMATION: Figure 5A: Influenza A virus
      (A/swine/Saskatchewan/18789/02(H1N1)) hemagglutinin (HA) gene
      (GenBank: AY619961.1)

<400> SEQUENCE: 1
```

```
atggaagcaa aactgttcgt actattctgt acattcactg tactgaaagc tgacactatc     60
tgtgtgggct accatgcaaa caactctaca aacactgttg atacagtact ggaaaagaac    120
ataactgtga ctcactcagt gaatttgctc gaagacagcc ataatgggaa gctctgcagt    180
ctgaatggga tagctccttt acaattgggg aagtgtaatg tagcgggatg gctcctgggc    240
aacccagaat gtgaccttct actcactgca aactcatggt cctatataat agagacgtcc    300
aattcagaga acgggacatg ctatcctggt gagttcatag attatgagga attaagggag    360
caattgagtt cggtttcttc atttgaaaag tttgaaattt tccccaaggc aaactcatgg    420
ccaaaccatg agacaactaa aggtgttaca gctgcctgct cttactctgg ggccagcagt    480
ttttaccgaa atttgctgtg gataacaaag aagggaactt catatccaaa actcagcaag    540
tcatacacga acaataaagg gaaagaagtg cttgtgctct ggggagtgca ccatcctccg    600
accaccagtg atcaacagag tatataccag aacactgatg catacgtctc agttgggtca    660
tcaaagtaca accgaagatt cactccagag atagcagcta gacccaaagt tagaggacag    720
gcaggcagga tgaactatta ttggacacta ctagaccaag gagacaccat aacatttgag    780
gccactggga atctgatagc accatggtat gccttcgcac taaataaggg gtcagactca    840
gggattataa catcagatgc tccagttcac aattgcgaca caaggtgcca aacccctcac    900
ggggcgttga acagtagcct ccccttttcag aatgtgcatc ctatcaccat tggagaatgt    960
cccaaatatg tcaagagcac caagctaaga atggcaacag gactaagaaa tgtcccatcc   1020
attcaatcca gaggactgtt tggagcaatt gccggattca ttgagggagg atggacaggc   1080
atgatagatg ggtggtatgg gtaccaccac cagaatgagc aaggatcagg gtatgccgct   1140
gatcagaaaa gcacacagaa tgcaatcgac ggaataacta acaaggtgaa ttcggtaatt   1200
gagaaaatga acactcaatt cactgcagtg ggtaaggaat tcaacaatct agagaggaga   1260
attgaaaatc tgaataggaa agtcgatgat gggttcctgg atgtttggac atacaatgct   1320
gaactgctcg ttctactgga gaatgaaaga actctggact ttcatgattc caatgtgagg   1380
aatttgtatg aaaaggtcag atcacaactg aggaataacg ccaaagaact tggaaatggt   1440
tgctttgagt tctatcacaa gtgtgatgat gaatgcatgg aaagtgtgaa gaacggcaca   1500
tatgactatc ccaaatattc agaagagtct aaattgaatc gggaagaaat agacggagtg   1560
agactagaat cgatgggagt ttaccaaatt ttggcgatct attccacagt cgccagttct   1620
ctagtcttgt tagtctccct gggggcaatc agcttctgga tgtgttctaa tgggtcattg   1680
caatgcagaa tatgcattta g                                             1701
```

<210> SEQ ID NO 2
<211> LENGTH: 566
<212> TYPE: PRT
<213> ORGANISM: Influenza A virus
<220> FEATURE:
<221> NAME/KEY: misc_feature
<222> LOCATION: (1)..(566)
<223> OTHER INFORMATION: Figure 5B: Influenza A virus Influenza A virus (A/swine/Saskatchewan/18789/02(H1N1)) hemagglutinin (HA) gene (GenBank: AY619961.1)

<400> SEQUENCE: 2

```
Met Glu Ala Lys Leu Phe Val Leu Phe Cys Thr Phe Thr Val Leu Lys
1               5                   10                  15

Ala Asp Thr Ile Cys Val Gly Tyr His Ala Asn Asn Ser Thr Asn Thr
            20                  25                  30
```

-continued

```
Val Asp Thr Val Leu Glu Lys Asn Ile Thr Val Thr His Ser Val Asn
        35                  40                  45

Leu Leu Glu Asp Ser His Asn Gly Lys Leu Cys Ser Leu Asn Gly Ile
    50                  55                  60

Ala Pro Leu Gln Leu Gly Lys Cys Asn Val Ala Gly Trp Leu Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Glu Asn Gly Thr Cys Tyr Pro Gly Glu Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Ala Asn Ser Trp Pro Asn His Glu
    130                 135                 140

Thr Thr Lys Gly Val Thr Ala Ala Cys Ser Tyr Ser Gly Ala Ser Ser
145                 150                 155                 160

Phe Tyr Arg Asn Leu Leu Trp Ile Thr Lys Lys Gly Thr Ser Tyr Pro
                165                 170                 175

Lys Leu Ser Lys Ser Tyr Thr Asn Asn Lys Gly Lys Glu Val Leu Val
            180                 185                 190

Leu Trp Gly Val His His Pro Pro Thr Thr Ser Asp Gln Gln Ser Ile
        195                 200                 205

Tyr Gln Asn Thr Asp Ala Tyr Val Ser Val Gly Ser Ser Lys Tyr Asn
    210                 215                 220

Arg Arg Phe Thr Pro Glu Ile Ala Ala Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp Tyr Ala Phe
            260                 265                 270

Ala Leu Asn Lys Gly Ser Asp Ser Gly Ile Ile Thr Ser Asp Ala Pro
        275                 280                 285

Val His Asn Cys Asp Thr Arg Cys Gln Thr Pro His Gly Ala Leu Asn
    290                 295                 300

Ser Ser Leu Pro Phe Gln Asn Val His Pro Ile Thr Ile Gly Glu Cys
305                 310                 315                 320

Pro Lys Tyr Val Lys Ser Thr Lys Leu Arg Met Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Arg Lys Val Asp Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
```

450 455 460

Lys Val Arg Ser Gln Leu Arg Asn Asn Ala Lys Glu Leu Gly Asn Gly
465 470 475 480

Cys Phe Glu Phe Tyr His Lys Cys Asp Asp Glu Cys Met Glu Ser Val
485 490 495

Lys Asn Gly Thr Tyr Asp Tyr Pro Lys Tyr Ser Glu Glu Ser Lys Leu
500 505 510

Asn Arg Glu Glu Ile Asp Gly Val Arg Leu Glu Ser Met Gly Val Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 3
<211> LENGTH: 1410
<212> TYPE: DNA
<213> ORGANISM: Influenza A virus
<220> FEATURE:
<221> NAME/KEY: misc_feature
<222> LOCATION: (1)..(1410)
<223> OTHER INFORMATION: Figure 6A: Influenza A virus
(A/swine/Saskatchewan/18789/02(H1N1)) neuraminidase (NA) gene
(GenBank: AY619960.1)

<400> SEQUENCE: 3
atgaatccaa atcaaaagat aataactatt gggtcaatct gcatggcaat tggagtaata 60
agtctggtgt tacaaattgg aaatataatc tcaatatggg ttaaccattc aattcaaact 120
ggaagtcaga accaccccga aacatgcaat caaagtgtca ttacctacga aaacaatact 180
tgggtgaatc aaacatacat caacataagc aataccaatt taattgcaga acaagctgta 240
gctccagtaa cactagcagg caattcctct ctctgtccca tcagtgggtg ggctatatac 300
agcaaggata atggtataag gataggttcg aagggagatg tatttgtcat cagagagcct 360
tttatttcat gctctcactt ggagtgcagg gctttctttc taactcaagg ggccttgttg 420
aatgacaagc attccaacgg aaccgttaaa gacagaagcc cttatagaac cctaatgagc 480
tgtcctgttg gcgaagctcc ttctccatac aattcaaggt ttgagtctgt tgcttggtca 540
gcaagtgctt gtcatgatgg cattagttgg ttgacaattg gtatttccgg cccagacaat 600
ggggcggtgg ctgtattgaa atacaatggc ataataacag atactgttaa gagttggaga 660
aacaatatat tgagaacaca agagtctgaa tgtgcctgca ttaacggttc ctgctttacc 720
ataatgactg atgggccaag taatggccag gcctcataca agattttcaa gatagaaaag 780
gggaaggtag tcaaatcagt tgagttgaat gcccctaatt accactacga ggagtgctcc 840
tgttatcctg atgctagtga ggtaatgtgt gtatgcagag acaactggca tggttcaaac 900
cgaccatggg tgtccttcaa tcagaatcta gagtaccaaa taggatacat atgcagcgga 960
gtttttggag acaacccacg ccccaatgat ggaacaggca gttgtggtcc agtgtcttct 1020
aatggggcat atggagtaaa ggggttttca tttaaatacg gtaatggtgt ttggatagga 1080
agaactaaaa gtactagctc aaggagtggg tttgagatga tttgggatcc caatgggtgg 1140
acagagacag acaacagttt ctctgtgaaa caagatattg tagcaataac tgattggtca 1200
ggatatagcg gaagttttgt tcagcatcca gaattaacgg ggctggactg catgaggcct 1260

```
tgcttctggg ttgagctgat cagaggaaga cccaaggaga atacaatctg gaccagtggg   1320

agcagcattt ccttttgtgg agtaaatagc gacactgtgg gttggtcttg gccagacggt   1380

gctgagttgc cattcaccat tgacaagtag                                    1410


<210> SEQ ID NO 4
<211> LENGTH: 469
<212> TYPE: PRT
<213> ORGANISM: Influenza A virus
<220> FEATURE:
<221> NAME/KEY: misc_feature
<222> LOCATION: (1)..(469)
<223> OTHER INFORMATION: Figure 6B: Influenza A virus
      (A/swine/Saskatchewan/18789/02(H1N1)) neuraminidase (NA) gene
      (GenBank: AY619960.1)

<400> SEQUENCE: 4

Met Asn Pro Asn Gln Lys Ile Ile Thr Ile Gly Ser Ile Cys Met Ala
1               5                   10                  15

Ile Gly Val Ile Ser Leu Val Leu Gln Ile Gly Asn Ile Ile Ser Ile
            20                  25                  30

Trp Val Asn His Ser Ile Gln Thr Gly Ser Gln Asn His Pro Glu Thr
        35                  40                  45

Cys Asn Gln Ser Val Ile Thr Tyr Glu Asn Asn Thr Trp Val Asn Gln
    50                  55                  60

Thr Tyr Ile Asn Ile Ser Asn Thr Asn Leu Ile Ala Glu Gln Ala Val
65                  70                  75                  80

Ala Pro Val Thr Leu Ala Gly Asn Ser Ser Leu Cys Pro Ile Ser Gly
                85                  90                  95

Trp Ala Ile Tyr Ser Lys Asp Asn Gly Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Ala Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Val Gly Glu Ala Pro Ser Pro Tyr Asn Ser Arg Phe Glu Ser
                165                 170                 175

Val Ala Trp Ser Ala Ser Ala Cys His Asp Gly Ile Ser Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Val Lys Ser Trp Arg Asn Asn Ile Leu
    210                 215                 220

Arg Thr Gln Glu Ser Glu Cys Ala Cys Ile Asn Gly Ser Cys Phe Thr
225                 230                 235                 240

Ile Met Thr Asp Gly Pro Ser Asn Gly Gln Ala Ser Tyr Lys Ile Phe
                245                 250                 255

Lys Ile Glu Lys Gly Lys Val Val Lys Ser Val Glu Leu Asn Ala Pro
            260                 265                 270

Asn Tyr His Tyr Glu Glu Cys Ser Cys Tyr Pro Asp Ala Ser Glu Val
        275                 280                 285

Met Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320
```

```
Val Phe Gly Asp Asn Pro Arg Pro Asn Asp Gly Thr Gly Ser Cys Gly
                325                 330                 335

Pro Val Ser Ser Asn Gly Ala Tyr Gly Val Lys Gly Phe Ser Phe Lys
            340                 345                 350

Tyr Gly Asn Gly Val Trp Ile Gly Arg Thr Lys Ser Thr Ser Ser Arg
        355                 360                 365

Ser Gly Phe Glu Met Ile Trp Asp Pro Asn Gly Trp Thr Glu Thr Asp
    370                 375                 380

Asn Ser Phe Ser Val Lys Gln Asp Ile Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465
```

```
<210> SEQ ID NO 5
<211> LENGTH: 982
<212> TYPE: DNA
<213> ORGANISM: Influenza A virus
<220> FEATURE:
<221> NAME/KEY: misc_feature
<222> LOCATION: (1)..(982)
<223> OTHER INFORMATION: Figure 7A: Influenza A virus
      (A/swine/Saskatchewan/18789/02(H1N1)) (GenBank: AY619959.1)

<400> SEQUENCE: 5

atgagtcttc taaccgaggt cgaaacgtac gttctctcta tcgtcccgtc aggccccctc     60

aaagccgaga tcgcgcagag acttgaagat gtctttgcag ggaagaacac cgatcttgag    120

gcactcatgg aatggctaaa gacaagacca atcctgtcac ctctgactaa ggggatttta    180

ggatttgtgt ttacactcac cgtgcccagt gagcgaggac tgcagcgtag acgctttgtc    240

caaaatgccc ttaatgggaa tggggatcca aacaacatgg acagagcagt caaactgtac    300

aggaaactaa aaagggaaat aacattccat ggggcaaaag aggtggcact cagttattcg    360

actggtgcac ttgccagttg catgggcctc atatacaaca gaatggggac tgtgaccact    420

gaagtggcat ttggcctagt ttgcgccaca tgtgagcaga ttgctgactc ccagcatcgg    480

tctcacagac agatggtaac aacaaccaac ccactgatca gacatgagaa cagaatggta    540

ctagccagta ccacggctaa ggccatggaa caaatggcag ggtcaagtga gcaggctgca    600

gaggctatgg aggttgctaa tcaagctaga caaatggtgc aggcaatgag gaccattggg    660

actcatccta gctccagtgc cggtctaaaa gatgatcttc ttgaaaattt gcaggcctac    720

cagaaacgga tgggagtgca aatgcagcga ttcaagtgat cctcttgtta ttgccgcaag    780

tatcattggg atcttgcact tgatattgtg gattcttgat cgtcttttct tcaaatgcat    840

ttatcgtcgc cttaaatacg gtttgaaaag agggccttct acggaaggag tgcctgagtc    900

tatgagggaa gaatatcggc aggaacagca gagtgctgtg gatgttgacg atggtcattt    960

tgtcaacata gagctggagt aa                                              982
```

-continued

<210> SEQ ID NO 6
<211> LENGTH: 97
<212> TYPE: PRT
<213> ORGANISM: Influenza A virus
<220> FEATURE:
<221> NAME/KEY: misc_feature
<222> LOCATION: (1)..(97)
<223> OTHER INFORMATION: Figure 7B: Influenza A virus
(A/swine/Saskatchewan/18789/02(H1N1)) matrix protein 2 (M2) gene
(GenBank: AY619959.1)

<400> SEQUENCE: 6

Met Ser Leu Leu Thr Glu Val Glu Thr Pro Thr Arg Asn Gly Trp Glu
1               5                   10                  15

Cys Lys Cys Ser Asp Ser Ser Asp Pro Leu Val Ile Ala Ala Ser Ile
            20                  25                  30

Ile Gly Ile Leu His Leu Ile Leu Trp Ile Leu Asp Arg Leu Phe Phe
        35                  40                  45

Lys Cys Ile Tyr Arg Arg Leu Lys Tyr Gly Leu Lys Arg Gly Pro Ser
    50                  55                  60

Thr Glu Gly Val Pro Glu Ser Met Arg Glu Glu Tyr Arg Gln Glu Gln
65                  70                  75                  80

Gln Ser Ala Val Asp Val Asp Asp Gly His Phe Val Asn Ile Glu Leu
                85                  90                  95

Glu

<210> SEQ ID NO 7
<211> LENGTH: 252
<212> TYPE: PRT
<213> ORGANISM: Influenza A virus
<220> FEATURE:
<221> NAME/KEY: misc_feature
<222> LOCATION: (1)..(252)
<223> OTHER INFORMATION: Figure 7C: Influenza A virus
(A/swine/Saskatchewan/18789/02(H1N1)) matrix protein 1 (M1) gene
(GenBank: AY619959.1)

<400> SEQUENCE: 7

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

-continued

```
Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 8
<211> LENGTH: 1497
<212> TYPE: DNA
<213> ORGANISM: Influenza A virus
<220> FEATURE:
<221> NAME/KEY: misc_feature
<222> LOCATION: (1)..(1497)
<223> OTHER INFORMATION: Figure 8A: Influenza A virus
      (A/swine/Saskatchewan/18789/02(H1N1)) nucleoprotein (NP) gene
      (GenBank: AY619958.1)

<400> SEQUENCE: 8

atggcgtctc aaggcaccaa acgatcttat gagcagatgg aaactggtgg agaacgccag      60

aatgccactg aaatcagagc atctgttggg agaatggttg gtggaatcgg aagattctac     120

atacagatgt gcactgaact caaactcagt gactatgaag ggagactgat ccaaaacagc     180

atcacaatag agagaatggt tctctcagca tttgatgaga ggagaaacaa atatctggaa     240

gagcatccca gtgctgggaa agaccctaag aagactggag gtccaatcta caggaggaga     300

gatgggaaat ggatgagaga attgatccta tatgacaaag aggagatcag aaggatttgg     360

cgtcaagcga ataatggaga agacgcaact gccggtctca cccatttgat gatctggcac     420

tccaatctga atgatgccac ctatcagagg acgagggcac ttgtgcgtac tggaatggat     480

cccaggatgt gttctctgat gcaaggctcg actctcccga ggaggtctgg agctgctgga     540

gcagctgtga aaggagttgg aacaatggtg atggaattga tccgaatgat caagcgaggg     600

atcaatgatc ggaatttctg gagaggcgaa aatgggcgga ggacaagaat tgcttatgaa     660

agaatgtgca acatcctcaa agggaagttc caaacagcgg cacaacgagc aatgatggac     720

caggtgaggg aaagccggaa tcctgggaat gctgaaattg aagatctcat ctttcttgca     780

cggtctgctc tcattctgag gggatcagtg gctcataagt cttgcctgcc tgcttgtgtg     840

tatggacttg ctgtggccag tggatacgac tttgaaaggg agggatactc cctagttgga     900

attgatcctt tccgtctgct ccaaaacagt caagtcttca gtcttatcag accaaacgaa     960

aatccagcac ataaaagcca gctggtatgg atggcatgcc actctgcagc ttttgaagat    1020

cttagagtgt caagcttcat tagaggaaca agagtagtcc caagaggaca actgtccacc    1080

agaggagttc agattgcttc aaatgagaac atggagacaa tggactccag tactcttgaa    1140

ctgaggagca gatactgggc tataaggacc agaagtgggg ggaacactaa ccagcagaga    1200

gcatccgcag ggcaaatcag cgtacagccc acattctctg tacagaggaa cctcccattc    1260

gagagagcaa ccattatggc ggcatttaca ggaaacactg aaggcagaac ttcagacatg    1320

agaacagaaa tcataaggat gatggaaaat gccagacctg aagatgtgtc tttccagggg    1380

cggggagtct tcgagctctc ggacgaaaag gcaacgaacc cgatcgtgcc ttcctttgac    1440

atgagcaacg aaggatctta tttcttcgga gacaatgcag aggaatatga caattaa       1497
```

<210> SEQ ID NO 9
<211> LENGTH: 498
<212> TYPE: PRT
<213> ORGANISM: Influenza A virus
<220> FEATURE:
<221> NAME/KEY: misc_feature
<222> LOCATION: (1)..(498)
<223> OTHER INFORMATION: Figure 8B: Influenza A virus
(A/swine/Saskatchewan/18789/02(H1N1)) nucleoprotein (NP) gene
(GenBank: AY619958.1)

<400> SEQUENCE: 9

```
Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
```

```
        340                 345                 350

Val Pro Arg Gly Gln Leu Ser Thr Arg Gly Val Gln Ile Ala Ser Asn
    355                 360                 365

Glu Asn Met Glu Thr Met Asp Ser Ser Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 10
<211> LENGTH: 838
<212> TYPE: DNA
<213> ORGANISM: Influenza A virus
<220> FEATURE:
<221> NAME/KEY: misc_feature
<222> LOCATION: (1)..(838)
<223> OTHER INFORMATION: Figure 9A: Influenza A virus
      (A/swine/Saskatchewan/18789/02(H1N1)) (GenBank: AY619957.1)

<400> SEQUENCE: 10

atggactcca acacgataac ctcgttccag gtagattgct atctatggca cataagaaag      60

ctgctcagca tgagagacat gtgtgatgct ccctttgatg atagactcag aagagatcaa     120

aaggcattaa agggaagagg cagcacactt ggactcgacc tgcgagtggc cacaatggaa     180

ggcaaaaaga ttgttgaaga catcctaaag agtgaaatgg atgaaaatct caaaattgca     240

attgcatcca gccctgctcc tcggtacatt accgatatga gcatagagga aataagcagg     300

gaatggtaca tgctcatgcc aaggcagaaa ataactgggg gtctgatggt gaaaatggat     360

caggccatta tggacaagag gataatactc aaggcgaact tctctgtcct tttgatcaa      420

ctggagacat tagtctcact gagggctttc acagacaatg gcgccattgt agctgaaata     480

tctcccattc cttccatgcc aggacattct acagaggatg tcaaaaatgc aattggaatc     540

ctcatcggcg gacttgaatg gaatgataac tcaattcgag cgtctgaaaa tatacagaga     600

ttcgcttggg gagtccgtga tgagaatggg ggacctccac tccctccaaa gcagaaacgc     660

tacatggcga gaagagttga gtcagaagtt tgaagaaatc agatggctaa ttgcagagtg     720

cagaaacata ttaaccaaaa ctgagaacag cttcgagcag ataacgttct tgcaagcatt     780

gcaactctta cttgaagtcg agagtgagat aaggacattt tcttttcagc ttatttag       838


<210> SEQ ID NO 11
<211> LENGTH: 121
<212> TYPE: PRT
<213> ORGANISM: Influenza A virus
<220> FEATURE:
<221> NAME/KEY: misc_feature
```

<222> LOCATION: (1)..(121)
<223> OTHER INFORMATION: Figure 9B: Influenza A virus
(A/swine/Saskatchewan/18789/02(H1N1)) nonstructural protein 2
(NS2, also termed NEP) gene (GenBank: AY619957.1)

<400> SEQUENCE: 11

Met Asp Ser Asn Thr Ile Thr Ser Phe Gln Asp Ile Leu Gln Arg Met
1 5 10 15

Ser Lys Met Gln Leu Glu Ser Ser Ser Ala Asp Leu Asn Gly Met Ile
20 25 30

Thr Gln Phe Glu Arg Leu Lys Ile Tyr Arg Asp Ser Leu Gly Glu Ser
35 40 45

Val Met Arg Met Gly Asp Leu His Ser Leu Gln Ser Arg Asn Ala Thr
50 55 60

Trp Arg Glu Glu Leu Ser Gln Lys Phe Glu Glu Ile Arg Trp Leu Ile
65 70 75 80

Ala Glu Cys Arg Asn Ile Leu Thr Lys Thr Glu Asn Ser Phe Glu Gln
85 90 95

Ile Thr Phe Leu Gln Ala Leu Gln Leu Leu Leu Glu Val Glu Ser Glu
100 105 110

Ile Arg Thr Phe Ser Phe Gln Leu Ile
115 120

<210> SEQ ID NO 12
<211> LENGTH: 230
<212> TYPE: PRT
<213> ORGANISM: Influenza A virus
<220> FEATURE:
<221> NAME/KEY: misc_feature
<222> LOCATION: (1)..(230)
<223> OTHER INFORMATION: Figure 9C: Influenza A virus
(A/swine/Saskatchewan/18789/02(H1N1)) nonstructural protein 1
(NS1) gene (GenBank: AY619957.1)

<400> SEQUENCE: 12

Met Asp Ser Asn Thr Ile Thr Ser Phe Gln Val Asp Cys Tyr Leu Trp
1 5 10 15

His Ile Arg Lys Leu Leu Ser Met Arg Asp Met Cys Asp Ala Pro Phe
20 25 30

Asp Asp Arg Leu Arg Arg Asp Gln Lys Ala Leu Lys Gly Arg Gly Ser
35 40 45

Thr Leu Gly Leu Asp Leu Arg Val Ala Thr Met Glu Gly Lys Lys Ile
50 55 60

Val Glu Asp Ile Leu Lys Ser Glu Met Asp Glu Asn Leu Lys Ile Ala
65 70 75 80

Ile Ala Ser Ser Pro Ala Pro Arg Tyr Ile Thr Asp Met Ser Ile Glu
85 90 95

Glu Ile Ser Arg Glu Trp Tyr Met Leu Met Pro Arg Gln Lys Ile Thr
100 105 110

Gly Gly Leu Met Val Lys Met Asp Gln Ala Ile Met Asp Lys Arg Ile
115 120 125

Ile Leu Lys Ala Asn Phe Ser Val Leu Phe Asp Gln Leu Glu Thr Leu
130 135 140

Val Ser Leu Arg Ala Phe Thr Asp Asn Gly Ala Ile Val Ala Glu Ile
145 150 155 160

Ser Pro Ile Pro Ser Met Pro Gly His Ser Thr Glu Asp Val Lys Asn
165 170 175

Ala Ile Gly Ile Leu Ile Gly Gly Leu Glu Trp Asn Asp Asn Ser Ile

-continued

```
            180                 185                 190

Arg Ala Ser Glu Asn Ile Gln Arg Phe Ala Trp Gly Val Arg Asp Glu
        195                 200                 205

Asn Gly Gly Pro Pro Leu Pro Pro Lys Gln Lys Arg Tyr Met Ala Arg
    210                 215                 220

Arg Val Glu Ser Glu Val
225                 230


<210> SEQ ID NO 13
<211> LENGTH: 2151
<212> TYPE: DNA
<213> ORGANISM: Influenza A virus
<220> FEATURE:
<221> NAME/KEY: misc_feature
<222> LOCATION: (1)..(2151)
<223> OTHER INFORMATION: Figure 10A: Influenza A virus
      (A/swine/Saskatchewan/18789/02(H1N1))(GenBank: AY619956)

<400> SEQUENCE: 13

atggaagact ttgtgcgaca atgcttcaat ccaatgatcg tcgagcttgc ggaaaaggca     60

atgaaggaat atggggaaga cccaaaaatc gagactaaca aattcgctgc aatatgcact    120

cacttggaag tatgtttcat gtattcggat ttccacttca ttgatgaacg gggcgaatca    180

ataattgtgg aatctggtga tccaaatgca ttactgaagc accgatttga aataattgaa    240

ggaagggacc gaacaatggc ctggacagtg gtgaatagca tctgcaacac cacaggagtc    300

gagaagccta aatttctccc ggatctgtat gattacaagg agaaccgatt cattgaaatt    360

ggagtgacac ggagagaggt ccatatatac tacctagaga aagccaacaa gataaaatcc    420

gagaagacac acattcacat cttttcattt actggagaag aaatggccac caaagcagac    480

tacactcttg atgaagaaag cagggcaaga atcaaaacca ggctgttcac tataagacaa    540

gaaatggcca gcaggggcct atgggattcc tttcgtcagt ccgaaagagg cgaagagaca    600

actgaagaaa gatttgaaat cacaggaacc atgcgtaggc ttgccgacca aagtctccca    660

ccgaacttct ccagccttga aaactttaga gcctatgtgg atggattcga accgaacggc    720

tgcattgagg gcaagctttc tcaaatgtca aaagaagtga acgccaggat cgagccattc    780

ctgaagacaa caccacgccc tctcaaatta cctgatgggc ccccttgctc ccagcggtcg    840

aaattcttgc tgatggatgc cttgaaacta agcatcgaag atccaagtca cgagggagag    900

gggataccac tatacgatgc aatcaaatgt atgaagacat tttcggctgg gaaagagccc    960

aatataatca aaccacatga gaaaggcata aatcccaatt accttctggc ttggaagcaa   1020

gtgctggcag aacttcagga ccttgaaaat gaagagaaaa tcccaaagac aaagaacatg   1080

aagaagacaa gccaattgaa gtgggcactt ggtgagaaca tggcaccaga gaaagtggac   1140

tttgaggatt gcaaggacat tggcgatctg aaacaatatg atagtgatga gccagagcct   1200

agatcgctag caagctggat ccagaacgaa ttcaataagg cgtgtgaatt gaccgactcg   1260

agctggatag aacttgatga aataggagaa gatgttgctc cgattgaaca cattgcaagt   1320

ataaggagga actattttac agcagaagtg tcccactgca gggccactga atacataatg   1380

aagggagtct acataaacac agctctgctc aatgcatctt gtgcagccat ggacgacttc   1440

cagctgattc caatgataag caaatgtaga acaaaggaag gaagacggaa aaccaacctg   1500

tatggattca tcataaaagg aagatcccat ttgaggaatg atactgatgt ggtaaacttt   1560

gtgagcatgg aattttctct cactgacccg aggctagaac cccacaaatg ggaaaagtac   1620

tgtgttcttg aaataggaga tatgctcctg aggactgcaa taggccaagt gtctaggccc   1680
```

-continued

```
atgttcctgt acgttagaac caatgggacc tctaagatca agatgaaatg gggtatggaa   1740

atgagacgct gcctccttca atctcttcaa cagattgaga gcatgattga ggccgagtct   1800

tctgtcaaag aaaaggacat gactaaggaa ttctttgaaa ataagccgga aaagtggcca   1860

attggagaat cccccagagg agtagaggaa ggctctatcg ggaaagtatg cagaacctta   1920

ctggcaaaat ctgtattcaa cagtctatat gcatctccac aacttgaggg attttcagct   1980

gaatcgagga aattgcttct cattgttcag gcacttaggg acaacctgga acctggaacc   2040

tttgatcttg gggggctata tgaagcaatt gaggagtgcc tgattaatga tccctgggtt   2100

ttgcttaatg catcttggtt caactccttc ctcacacatg cactgaaata g            2151
```

```
<210> SEQ ID NO 14
<211> LENGTH: 716
<212> TYPE: PRT
<213> ORGANISM: Influenza A virus
<220> FEATURE:
<221> NAME/KEY: misc_feature
<222> LOCATION: (1)..(716)
<223> OTHER INFORMATION: Figure 10B: Influenza A virus
      (A/swine/Saskatchewan/18789/02(H1N1)) polymerase acidic protein 2
      (PA) gene (GenBank: AY619956)

<400> SEQUENCE: 14

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Thr Glu Glu Arg Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255
```

-continued

```
Ile Glu Pro Phe Leu Lys Thr Thr Pro Arg Pro Leu Lys Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Ile Lys Pro His Glu Lys Gly Ile Asn Pro Asn Tyr Leu Leu
                325                 330                 335

Ala Trp Lys Gln Val Leu Ala Glu Leu Gln Asp Leu Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Gly Asp Leu Lys Gln Tyr Asp Ser Asp Glu Pro Glu Pro
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Ile Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Pro Glu Lys Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
```

```
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 15
<211> LENGTH: 2274
<212> TYPE: DNA
<213> ORGANISM: Influenza A virus
<220> FEATURE:
<221> NAME/KEY: misc_feature
<222> LOCATION: (1)..(2274)
<223> OTHER INFORMATION: Figure 11A: Influenza A virus
      (A/swine/Saskatchewan/18789/02(H1N1)) polymerase subunit PB1
      (PB1) gene (GenBank: AY619955.1)

<400> SEQUENCE: 15

atggatgtca atccgacttt acttttcttg aaagttccag cgcaaaatgc cataagcacc     60

acattcccat atactggaga tcctccctac agccatggaa cgggaacggg atacaccatg    120

gacacagtca acaggacaca tcaatactca gaaaagggga aatggacaac aaacacagag    180

actggagcac cccaacttaa cccgattgac ggaccattac ctgaggataa tgaaccaagt    240

ggatatgcac aaacagactg cgtcctggaa gcaatggctt tccttgaaga atcccaccca    300

ggaatctttg aaaactcgtg tcttgaaacg atggaagttg ttcaacaaac aagagtggac    360

aagctgaccc aaggtcgcca gacctatgat tggacattaa acaggaatca gccagctgca    420

actgcattag ccaatactat agaggtcttc agatcgaacg gtttaacagc taatgaatcg    480

ggaaggctaa tcgatttcct caaggatgtg atggaatcaa tggataaaga ggaaatggaa    540

ataacaacgc acttccaaag aaaaagaagg gtgagagaca acatgaccaa gaaaatggtc    600

acacaaagaa caataggaaa gaagaagcag agattaaaca agagaagcta tctaataaga    660

gcattgacat taaacacaat gacaaaagat gctgaaagag gcaaattaaa gagaagagca    720

attgcaacac ccgggatgca aatcagagga tttgtgtatt ttgttgaaac actagcaagg    780

agcatttgtg agaagctcga gcaatctgga cttccagttg gaggcaatga aaagaaggct    840

aaactggcaa atgtcgtgag aaagatgatg actaattcac aagacacaga gctctctttc    900

acaatcactg gagacaacac caaatggaat gaaaatcaaa accctcgaat gttcctggca    960

atgataacat acataacaag aaatcaacct gaatggttta gaaatgtttt gagcattgca   1020

cctataatgt tctcgaataa aatggcaaga ctaggaaaag gatacatgtt cgaaagtaag   1080

agcatgaagc ttcgaacaca gataccggca gaaatgctag caagtattga tctgaaatat   1140

ttcaacgaat caacaagaaa gaaaatcgag aagataagac ctcttctaat agatggtaca   1200

gcctcattga gccctggaat gatgatgggc atgttcaaca tgctaagtac agttttggga   1260

gtctcaattc tgaatctagg gcaaaagaga tacaccaaaa caacatactg gtgggacgga   1320

ctccaatcct ctgatgactt tgctctcata gtgaatgctc cgaatcatga gggtatacaa   1380

gcaggagtag atagattcta tagaacctgc aagctggtcg gaatcaacat gagcaaaaag   1440

aagtcctaca taaacagaac agggacattt gaattcacaa gctttttcta tcgctatgga   1500

tttgtagcca actttagcat ggagctgccc agctttggag tgtctgggat caatgaatct   1560

gccgacatga gcattggagt aacagtgata aagaacaaca tgataaacaa tgatcttgga   1620

ccagcaacag ctcaaatggc tcttcagctg ttcatcaagg attacagata cacatatcgg   1680

tgtcacagag ggacacacaa aattcagaca aggaggtcat tcgagctgaa aaaactgtgg   1740
```

-continued

```
gaacaaaccc gctcaaaggc aggactgctg gtttcagatg gaggaccaaa cttatacaat   1800

atccggaatc tccacattcc ggaagtctgc ctgaaatggg agctaatgga tgaagactat   1860

cagggaaggc tttgtaatcc cctgaatcca tttgtcagcc acaaagagat agagtctgta   1920

aacaatgctg tggtgatgcc agctcatgga ccagccaaga gcatggaata tgatgctgtt   1980

gctactacac actcctggat tcctaagagg aaccgctcca ttctcaacac aagtcaaagg   2040

ggaatccttg aagatgaaca gatgtaccaa aagtgctgca atctattcga gaaattcttc   2100

cctagcagct catacaggag accagttggg atttccagca tggtggaggc catggtttct   2160

agggcccgaa ttgatgcgcg aattgacttc gaatctggac ggattaagaa ggaggaattt   2220

gctgagatca tgaagatctg ttccaccatt gaagagctca gacggcagaa atag         2274
```

```
<210> SEQ ID NO 16
<211> LENGTH: 757
<212> TYPE: PRT
<213> ORGANISM: Influenza A virus
<220> FEATURE:
<221> NAME/KEY: misc_feature
<222> LOCATION: (1)..(757)
<223> OTHER INFORMATION: Figure 11B: Influenza A virus
      (A/swine/Saskatchewan/18789/02(H1N1)) polymerase subunit PB1
      (PB1) gene (GenBank: AY619955.1)

<400> SEQUENCE: 16

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
```

-continued

```
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670
```

Ser Ile Leu Asn Thr Ser Gln Arg Gly Ile Leu Glu Asp Glu Gln Met
675 680 685

Tyr Gln Lys Cys Cys Asn Leu Phe Glu Lys Phe Phe Pro Ser Ser Ser
690 695 700

Tyr Arg Arg Pro Val Gly Ile Ser Ser Met Val Glu Ala Met Val Ser
705 710 715 720

Arg Ala Arg Ile Asp Ala Arg Ile Asp Phe Glu Ser Gly Arg Ile Lys
725 730 735

Lys Glu Glu Phe Ala Glu Ile Met Lys Ile Cys Ser Thr Ile Glu Glu
740 745 750

Leu Arg Arg Gln Lys
755

<210> SEQ ID NO 17
<211> LENGTH: 2280
<212> TYPE: DNA
<213> ORGANISM: Influenza A virus
<220> FEATURE:
<221> NAME/KEY: misc_feature
<222> LOCATION: (1)..(2280)
<223> OTHER INFORMATION: Figure 12A: Influenza A virus (A/swine/Saskatchewan/18789/02(H1N1)) polymerase subunit PB2 (PB2) gene (GenBank: AY619954.1)

<400> SEQUENCE: 17
atggagagaa taaaagaact aagagatcta atgtcacagt ctcgcactcg cgagatactc 60
accaaaacca ctgtggacca catggccata atcaaaaagt acacatcagg aaggcaagag 120
aagaaccctg cactcaggat gaagtggatg atggcaatga aatatccaat tgcagcagac 180
aagagaataa tggagatgat tcctgaaagg aatgaacagg gacaaaccct ttggagcaaa 240
gcaaatgatg ccggctcaga ccgagtgatg gtatctcctc tggctgtgac atggtggaat 300
aggaatggac caacaactag tacagttcat tatccaaagg tgtataagac ttatttcgaa 360
aaagtcgaaa ggttgaaaca cgggaccttt ggccctgttc gcttcagaaa tcaagttaaa 420
ataagacgga tggttgacat aaaccctggt cacgcaggcc tcagtgccaa agaggcacag 480
gatgtaataa tggaagtcgt tttcccaaat gaagtgggag cgagaatact aacatcggag 540
tcacaactga cgataccaaa agaaaagaag gaagaactcc aggactgcaa gattgcccct 600
ttgatggttg catacatgct agaaagggaa ttggtccgta aaactaggtt cctcccagtg 660
gctggtggaa caagcagtgt ctacattgag gtgctgcatt taactcaggg gacatgctgg 720
gagcaaatgt acaccccagg aggggaagtg aggaatgatg atgttgacca aagcttgatt 780
atcgctgcca ggaacatagt aagaagagca acagtatcag cagacccact agcatctcta 840
ttggagatgt gtcacagcac acagattgga gggataagga tggtagacat tcttcggcaa 900
aatccgacag aggaacaagc tgtggacata tgcaaggcag caatgggctt aaggattagc 960
tcatctttca gctttggcgg attcactttc aaaagaacaa gcgggtcgtc agttaagaga 1020
gaagaagaaa tgcttacggg caaccttcaa acattgaaaa taagagtaca tgaggggtat 1080
gaagagttca caatggttgg gagaagagca acagccattc tcaggaaggc aaccagaaga 1140
ttgatccagc taatagtaag tgggagagac gagcagtcaa ttgctgaagc aataattgtg 1200
gccatggtat tctcacaaga ggattgcatg atcaaggcag tccgaggtga tttgaacttt 1260
gtcaatagag caaaccagcg gctaaaccca atgcatcaac tcttgagaca cttccaaaag 1320
gacgcaaaag tgcttctcca aaactgggga attgaaccca ttgacaatgt aatgggaatg 1380

-continued

```
atcgggatat tacccgacat gactccaagt actgagatgt cgctgagggg gataagagtc   1440

agtaagatgg gagtagatga atactccagc acagagagag tggtagtgag cattgaccga   1500

tttttaagag tccgggacca acgagggaat gtgctattgt cgcctgaaga agtcagcgag   1560

acacaaggaa cagagaagct gacaataact tattcgtcgt caatgatgtg ggagatcaat   1620

ggccctgaat cggttttggt caacacttat cagtggatca tcagaaattg ggaaactgtg   1680

aaaattcaat ggtcacaaga ccccacgatg ttatataaca agatggaatt cgagccattc   1740

cagtctctgg tccctaaagc agccagaggt cagtacagtg gattcgtgag gacacttttc   1800

caacagatgc gggatgtgct tggaactttc gacactgttc agataataaa acttctcccc   1860

tttgctgctg ctccaccaga acaaagtagg atgcaattct cctccttgac tgtgaatgtg   1920

aggggatcag gaatgagaat actagtaagg ggcaattctc cagtgttcaa ttacaataag   1980

gccactaaga ggcttacagt tctcggaaaa gatgcaggtg cattgatcga agatccagac   2040

gaaggcacag ctggagtaga gtctgctgtt ttgagaggat tcctcatctt gggcaaagaa   2100

gacaagagat atggcccagc attgagcatc aatgagctga gcaatcttgc aaaaggagag   2160

aaggctaatg tgctaattgg gcaaggagac gtggtgttgg taatgaaacg gaaacgggac   2220

tctagcatac ttactgacag tcagacagcg accaaaagaa ttcggatggc catcaattag   2280
```

```
<210> SEQ ID NO 18
<211> LENGTH: 759
<212> TYPE: PRT
<213> ORGANISM: Influenza A virus
<220> FEATURE:
<221> NAME/KEY: misc_feature
<222> LOCATION: (1)..(759)
<223> OTHER INFORMATION: Figure 12B: Influenza A virus
      (A/swine/Saskatchewan/18789/02(H1N1)) polymerase subunit PB2
      (PB2) gene (GenBank: AY619954.1)

<400> SEQUENCE: 18

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Ala Ala Asp Lys Arg Ile Met
    50                  55                  60

Glu Met Ile Pro Glu Arg Asn Glu Gln Gly Gln Thr Leu Trp Ser Lys
65                  70                  75                  80

Ala Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Val Glu Arg Leu Lys His Gly
        115                 120                 125

Thr Phe Gly Pro Val Arg Phe Arg Asn Gln Val Lys Ile Arg Arg Met
    130                 135                 140

Val Asp Ile Asn Pro Gly His Ala Gly Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Pro Lys Glu Lys Lys Glu Glu
            180                 185                 190
```

```
Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Leu Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Ala Arg Gly Gln Tyr
            580                 585                 590

Ser Gly Phe Val Arg Thr Leu Phe Gln Gln Met Arg Asp Val Leu Gly
        595                 600                 605
```

Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Ile Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 19
<211> LENGTH: 1762
<212> TYPE: DNA
<213> ORGANISM: Influenza A virus
<220> FEATURE:
<221> NAME/KEY: misc_feature
<222> LOCATION: (1)..(1762)
<223> OTHER INFORMATION: Figure 13A: Influenza A virus (A/Swine/Texas/
      4199-2/98 (H3N2)) hemagglutinin gene

<400> SEQUENCE: 19
agcaaaagca ggggataatt ctattaacca tgaagactat cattgctttg agctacattt 60
tatgtctggt tttcgctcaa aaacttcccg gaaatgacaa cagcacagca acgctgtgcc 120
tgggacacca tgcagtgcca aacggaaccc tagtgaaaac aatcacgaat gatcaaattg 180
aagtgactaa tgctactgag ctggttcaga gttcctcaac aggtagaata tgcgacagtc 240
ctcaccgaat ccttgatgga aaaaactgca cattgataga tgctctactg ggagaccctc 300
attgcgatgg ctttcaaaat aaggaatggg accttttat tgaacgcagc aaagcttaca 360
gcaactgtta cccttatgat gtgccggatt attcctccct taggtcacta gttgcctcat 420
caggcaccct ggagtttacc aatgaagact tcaattggac tggggtcgct caggatgggg 480
gaagctattc ttgcaaaagg ggatctgtta aaagtttctt tagtagattg aattggttac 540
acaaattaga atacaaatat ccagcactga acgtgactat gccaaacaat gacaaatttg 600
acaaattgta catttggggg gttcaccacc cgagcacgga cagtgaacaa accagcctgt 660
atgttcaagc aatagggaga gtcacagtct ctaccaaaag tagccaacaa actgtaatcc 720
cgaacatcgg gtccagaccc tgggtgaggg gcatctccag tagaataagc atctattgga 780
caatagtaaa accgggagac atacttttga ttagcagcac agggaatcta attgctcctc 840
ggggttactt caaaatacga aatgggaaaa gctcaataat gaggtcagat gcacccattg 900
acaactgcta ttctgaatgc atcactccaa atggaagcat tcccaatgac aaaccttttc 960
aaaatgtaaa taggatcaca tatggggcct gtcccaaata tgttaagcaa aaaactctga 1020
aattggcaac agggatgcgg aatgtaccag agaaacaaac tagaggcata ttcggcgcaa 1080

-continued tcgcaggttt catagaaaat ggttgggagg gaatggtaga cggttggtac ggtttcaggc 1140
atcaaaattc tgagggcaca ggacaagcag cagatcttaa aagcacccaa gcagcaatcg 1200
atcaagtcaa cgggaaattg aataggttaa tcgagaaaac gaacgagaaa ttccatcaaa 1260
tcgaaaaaga attttcagaa gtagaaggga gaattcagga cctcgagaaa tatgttgaag 1320
acactaaaat agatctctgg tcttacaacg cggagctcct tgttgccctg gagaatcaac 1380
atacaattga tctaactgac tcagaaatga acaaactgtt tgaaaaaaca aggaagcaac 1440
tgagggaaaa tgctgaggac atgggcaatg gttgcttcaa aatataccac aaatgtgaca 1500
atgcctgcat agggtcaatc agaaatggaa cttatgacca tgatgtatac agagacgaag 1560
cattaaacaa ccggttccag atcaaaggtg ttgagctgaa atcaggatac aaagattgga 1620
tcctatggat ttcctttgcc atatcatgct tttgctttg tgttgttttg ctggggttca 1680
tcatgtgggc ctgccaaaaa ggcaacatta ggtgcaacat ttgcatttga gtgcattaat 1740
taaaaacacc cttgtttcta ct 1762

<210> SEQ ID NO 20
<211> LENGTH: 566
<212> TYPE: PRT
<213> ORGANISM: Influenza A virus
<220> FEATURE:
<221> NAME/KEY: misc_feature
<222> LOCATION: (1)..(566)
<223> OTHER INFORMATION: Figure 13B: Influenza A virus (A/Swine/Texas/
4199-2/98 (H3N2)) hemagglutinin gene

<400> SEQUENCE: 20

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Leu Val Lys Thr Ile Thr Asn Asp
35 40 45

Gln Ile Glu Val Thr Asn Ala Thr Glu Leu Val Gln Ser Ser Ser Thr
50 55 60

Gly Arg Ile Cys Asp Ser Pro His Arg Ile Leu Asp Gly Lys Asn Cys
65 70 75 80

Thr Leu Ile Asp Ala Leu Leu Gly Asp Pro His Cys Asp Gly Phe Gln
85 90 95

Asn Lys Glu Trp Asp Leu Phe Ile Glu Arg Ser Lys Ala Tyr Ser Asn
100 105 110

Cys Tyr Pro Tyr Asp Val Pro Asp Tyr Ser Ser Leu Arg Ser Leu Val
115 120 125

Ala Ser Ser Gly Thr Leu Glu Phe Thr Asn Glu Asp Phe Asn Trp Thr
130 135 140

Gly Val Ala Gln Asp Gly Gly Ser Tyr Ser Cys Lys Arg Gly Ser Val
145 150 155 160

Lys Ser Phe Phe Ser Arg Leu Asn Trp Leu His Lys Leu Glu Tyr Lys
165 170 175

Tyr Pro Ala Leu Asn Val Thr Met Pro Asn Asn Asp Lys Phe Asp Lys
180 185 190

Leu Tyr Ile Trp Gly Val His His Pro Ser Thr Asp Ser Glu Gln Thr
195 200 205

Ser Leu Tyr Val Gln Ala Ile Gly Arg Val Thr Val Ser Thr Lys Ser
210 215 220

-continued

```
Ser Gln Gln Thr Val Ile Pro Asn Ile Gly Ser Arg Pro Trp Val Arg
225                 230                 235                 240

Gly Ile Ser Ser Arg Ile Ser Ile Tyr Trp Thr Ile Val Lys Pro Gly
                245                 250                 255

Asp Ile Leu Leu Ile Ser Ser Thr Gly Asn Leu Ile Ala Pro Arg Gly
            260                 265                 270

Tyr Phe Lys Ile Arg Asn Gly Lys Ser Ser Ile Met Arg Ser Asp Ala
        275                 280                 285

Pro Ile Asp Asn Cys Tyr Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Lys Tyr Val Lys Gln Lys Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Val Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
taatacgact cactataggg 20

<210> SEQ ID NO 22
<211> LENGTH: 43
<212> TYPE: DNA
<213> ORGANISM: Artificial Sequence
<220> FEATURE:
<223> OTHER INFORMATION: Synthetic primer

<400> SEQUENCE: 22
gtcatttccg ggaagttttt gcacccaagt attgttttcg tag 43

<210> SEQ ID NO 23
<211> LENGTH: 43
<212> TYPE: DNA
<213> ORGANISM: Artificial Sequence
<220> FEATURE:
<223> OTHER INFORMATION: Synthetic primer

<400> SEQUENCE: 23
gctgaaatca ggatacaaag attgaggcct tgcttctggg ttg 43

<210> SEQ ID NO 24
<211> LENGTH: 18
<212> TYPE: DNA
<213> ORGANISM: Artificial Sequence
<220> FEATURE:
<223> OTHER INFORMATION: Synthetic primer

<400> SEQUENCE: 24
acaggtgtcc gtgtcgcg 18

<210> SEQ ID NO 25
<211> LENGTH: 43
<212> TYPE: DNA
<213> ORGANISM: Artificial Sequence
<220> FEATURE:
<223> OTHER INFORMATION: Synthetic primer

<400> SEQUENCE: 25
ctacgaaaac aatacttggg tgcaaaaact tcccggaaat gac 43

<210> SEQ ID NO 26
<211> LENGTH: 43
<212> TYPE: DNA
<213> ORGANISM: Artificial Sequence
<220> FEATURE:
<223> OTHER INFORMATION: Synthetic primer

<400> SEQUENCE: 26
caacccagaa gcaaggcctc aatctttgta tcctgatttc agc 43

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tggccaaacc atgagacaac 20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer -continued

```
<400> SEQUENCE: 28

ggcgttattc ctcagttgtg                                              20


<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29

cgcaatcgca ggtttcatag                                              20


<210> SEQ ID NO 30
<211> LENGTH: 43
<212> TYPE: DNA
<213> ORGANISM: Artificial Sequence
<220> FEATURE:
<223> OTHER INFORMATION: Synthetic primer

<400> SEQUENCE: 30

caacccagaa gcaaggcctc aatctttgta tcctgatttc agc                    43
```

RECOMBINANT SWINE INFLUENZA VIRUS AND USES THEREOF

CROSS-REFERENCE TO RELATED APPLICATION

This application is a continuation of U.S. patent application Ser. No. 13/559,940, filed Jul. 27, 2012, from which application priority is claimed pursuant to 35 U.S.C. § 120, and claims the benefit under 35 U.S.C. § 119(e)(1) to U.S. Provisional Application No. 61/514,156, filed Aug. 2, 2011, which applications are incorporated herein by reference in their entireties.

TECHNICAL FIELD

The present invention pertains generally to influenza virus and immunogenic compositions and methods for treating and preventing influenza infection. In particular, the invention relates to recombinant, chimeric swine influenza viruses expressing more than one hemagglutinin (HA) subtype.

BACKGROUND

Swine influenza (SI) is an acute respiratory disease of swine caused by type A and type C influenza viruses. Influenza A viruses are segmented negative-strand RNA viruses and can be isolated from a number of other animal host species, including birds, humans, horses, whales, and mink. Although whole influenza viruses rarely cross the species barrier, gene segments can cross this barrier through the process of genetic reassortment, or genetic shift. Pigs support the replication of both human and avian influenza A viruses and have been postulated to play an important role in interspecies transmission by acting as a "mixing vessel" for reassortment between viruses specific to different host species (Scholtissek, *Eur. J. Epidemiol.* (1994) 10:455-458). This may lead to the generation of influenza viruses capable of crossing the species barrier to humans.

Influenza virions include an internal ribonucleoprotein core (a helical nucleocapsid) containing the single-stranded RNA genome, and an outer lipoprotein envelope lined inside by a matrix protein (M1). The genome of influenza A virus consists of eight segmented negative sense single-stranded RNA molecules. Each segment possesses segment-specific RNA packaging signals which are composed of both the noncoding regions and short coding regions at both 5' and 3' ends. The eight segmented RNAs encode 11 viral proteins, including RNA-dependent RNA polymerase proteins (PB2, PB1 and PA) and nucleoprotein (NP) which form the nucleocapsid; the matrix membrane proteins (M1, M2); hemagglutinin (HA) and neuraminidase (NA), both surface glycoproteins which project from the lipid-containing envelope; the nonstructural protein (NS1), nuclear export protein (NEP, also termed NS2), the proapoptotic factor PB1-F2. HA is critical for virus binding and entry to the cells, and is the major neutralizing antibody target, whereas NA plays a role in progeny virus release and is essential for virus propagation. Transcription and replication of the genome take place in the nucleus and assembly occurs via budding on the plasma membrane. The viruses can reassort genes during mixed infections.

Multiple swine influenza virus (SIV) subtypes continue to circulate in swine populations despite available vaccines. Currently, H1N1, H3N2, and H1N2 are the dominant subtypes that cause disease in the North American swine population. SIVs of the subtype H3N2 were generated by reassortment between human, avian and classical swine viruses, are undergoing rapid evolution and in general cause more severe disease than classical H1N1 SIV. Current SIV vaccines do not provide cross-protection against multiple antigenic SIV variants.

Thus, there remains a need for the development of effective strategies for the treatment and prevention of swine influenza infection.

SUMMARY OF THE INVENTION

The present invention relates to recombinant, chimeric influenza viruses that possess HAs from two or more subtypes of SIVs and methods of producing and using the same. In preferred embodiments, all or a portion of the NA segment is absent from the recombinant virus such that virus propagation is hindered. Because NA is essential for virus propagation, the function of NA can be provided in culture by growing the virus in the presence of sialidase. The recombinant virus that expresses more than one HA type can be used in immunogenic compositions to stimulate an immune response against influenza virus, and for treating and preventing influenza virus infection. Because HAs from different subtypes of SIVs are present, compositions including the chimeric influenza viruses can be used to provide broad coverage against a number of influenza strains.

In particular, the inventors herein have found that a chimeric virus including both H1 and H3, and retaining NA 3' and 5' viral RNA-specific packaging signals but lacking the remainder of the NA segment, grows efficiently in culture and is attenuated in pigs as no sialidase is present in swine. The NA packaging signals are largely retained for efficient packaging. Such chimeric constructs can be used as effective and safe live, attenuated vaccines.

Accordingly, in one embodiment, the invention is directed to a recombinant, chimeric porcine influenza virus comprising more than one hemagglutinin (HA) segment (segment 4) from more than one influenza subtype. In particular, the virus comprises segments 1-5, 7 and 8 from a first influenza subtype and a second segment 4 from a second influenza subtype. Further, all or a portion of the neuraminidase (NA) segment (segment 6) of the first influenza subtype is missing to render an attenuated virus.

In certain embodiments, the second segment 4 comprises NA packaging sequences from said first influenza subtype located 3' and optionally 5' to said second segment 4. In additional embodiments, the NA packaging sequences comprise 3' NA packaging sequences from the 3' NA UTR and the 3' NA coding sequence and, optionally 5' NA packaging sequences from the 5' NA UTR and the 5' NA coding sequence.

In further embodiments, the influenza virus described above is from an influenza A virus. In certain embodiments, the influenza virus comprises an HA segment from an H1N1 subtype and an HA segment from an H3N2 subtype. In certain embodiments, the first influenza subtype is H1N1, such as A/swine/Saskatchewan/18789/02. In other embodiments, the second influenza subtype is H3N2, such as A/Swine/Texas/4199-2/98.

In yet additional embodiments, the invention is directed to an attenuated, recombinant, porcine influenza virus comprising segments 1-5, 7 and 8 from an H1N1 influenza subtype, and segment 4 from an H3N2 influenza subtype. Further, all or a portion of segment 6 from the H1N1 influenza subtype is missing and the H3N2 segment 4 is flanked by NA packaging sequences from the H1N1 subtype. The packaging sequences comprise 3' NA packaging sequences from the 3' NA UTR and the 3' NA coding sequence and 5' NA packaging sequences from the 5' NA UTR and the 5' NA coding sequence. In certain embodiments, the H1N1 subtype is A/swine/Saskatchewan/18789/02 and the H3N2 subtype is A/Swine/Texas/4199-2/98.

In further embodiments, the invention is directed to a composition comprising any one of the recombinant viruses described above, and a pharmaceutically acceptable excipient. In certain embodiments, the composition further comprises an adjuvant. In yet additional embodiments, the invention is directed to a method of eliciting an immunological response in a vertebrate subject, comprising administering the composition to the subject. In other embodiments, the invention is directed to a method of treating or preventing an influenza infection in a vertebrate subject, comprising administering to the subject a therapeutically effective amount of the composition. In other embodiments, the invention is directed to a method of vaccinating a subject against an influenza virus, comprising administering an effective amount of the composition to the subject. In certain embodiments, the subject is a porcine subject.

In additional embodiments, the invention is directed to a recombinant construct comprising: (a) a porcine influenza H3N2 subtype HA segment; and (b) porcine influenza H1N1 subtype NA packaging sequences located 3' and optionally 5' to said H3N2 HA segment. In certain embodiments, the H3N2 HA segment is flanked by H1N1 NA packaging sequences that comprise 3' NA packaging sequences from the 3' NA UTR and the 3' NA coding sequence and 5' NA packaging sequences from the 5' NA UTR and the 5' NA coding sequence. In additional embodiments the H1N1 subtype is A/swine/Saskatchewan/18789/02 and the H3N2 subtype is A/Swine/Texas/4199-2/98.

In further embodiments, the invention is directed to a method of producing a recombinant, chimeric influenza virus, comprising transfecting a host cell with (a) individual plasmids comprising segments 1-5, 7 and 8 from an H1N1 influenza subtype; and (b) a recombinant construct described above, and culturing the host cell under conditions that result in the production of the recombinant, chimeric influenza virus.

In other embodiments, the invention is directed to a cell transformed with (a) individual plasmids comprising segments 1-5, 7 and 8 from an H1N1 influenza subtype; and (b) a recombinant construct as described above.

In further embodiments, the invention is directed to a method of producing a composition comprising combining any of the recombinant, chimeric porcine influenza viruses described above with a pharmaceutically acceptable excipient.

In other embodiments, the invention is directed to a method of producing an influenza vaccine comprising: (a) propagating any one of the recombinant, chimeric porcine influenza viruses described above; (b) purifying the virus; and (c) combining the purified virus with a pharmaceutically acceptable excipient.

In yet additional embodiments, the invention is directed to a kit comprising one or more containers of any one of the recombinant viruses described above, or the compositions described above.

These and other embodiments of the subject invention will readily occur to those of skill in the art in view of the disclosure herein.

BRIEF DESCRIPTION OF THE FIGURES

FIG. 1A depicts the 8 segments of a wild-type Influenza A H1N1 SIV virus, A/swine/Saskatchewan/18789/02 (termed "SK02" herein) and the 8 segments of the recombinant, chimeric attenuated virus produced as described in the examples (termed "SIV-606" herein). FIG. 1B is a schematic representation of the segment termed "H3-HA" in FIG. 1A. The HA segment depicted in FIG. 1B was derived from an H3N2 Influenza A virus, A/Swine/Texas/4199-2/98 (termed "Tx98" herein) and included the 3' and 5' NA packaging signals from SK02.

FIGS. 5A and 5B (SEQ ID NOS:1 and 2) show the nucleotide sequence and amino acid sequence, respectively, of HA from SIV SK02 (GenBank: AY619961.1).

FIGS. 6A and 6B (SEQ ID NOS:3 and 4) show the nucleotide sequence and amino acid sequence, respectively, of NA from SIV SK02 (GenBank: AY619960.1).

FIGS. 7A-7C (SEQ ID NOS:5, 6 and 7) show the matrix nucleotide sequence (FIG. 7A) and the amino acid sequences of M2 (FIG. 7B) and M1 (FIG. 7C) from SIV SK02 (GenBank: AY619959.1).

FIGS. 8A and 8B (SEQ ID NOS:8 and 9) show the nucleotide sequence and amino acid sequence, respectively, of NP from SIV SK02 (GenBank: AY619958.1).

FIGS. 9A-9C (SEQ ID NOS:10, 11 and 12) show the nonstructural protein nucleotide sequence (FIG. 9A) and the amino acid sequences of NEP (FIG. 9B) and NS1 (FIG. 9C) from SIV SK02 (GenBank: AY619957.1).

FIGS. 10A and 10B (SEQ ID NOS:13 and 14) show the nucleotide sequence and amino acid sequence, respectively, of PA from SIV SK02 (GenBank: AY619956).

FIGS. 11A and 11B (SEQ ID NOS:15 and 16) show the nucleotide sequence and amino acid sequence, respectively, of PB1 from SIV SK02 (GenBank: AY619955.1).

FIGS. 12A and 12B (SEQ ID NOS:17 and 18) show the nucleotide sequence and amino acid sequence, respectively, of PB2 from SIV SK02 (GenBank: AY619954.1).

FIGS. 13A and 13B (SEQ ID NOS:19 and 20) show the nucleotide sequence and amino acid sequence, respectively, of HA from SIV Tx98.

DETAILED DESCRIPTION OF THE INVENTION

Figure 1:
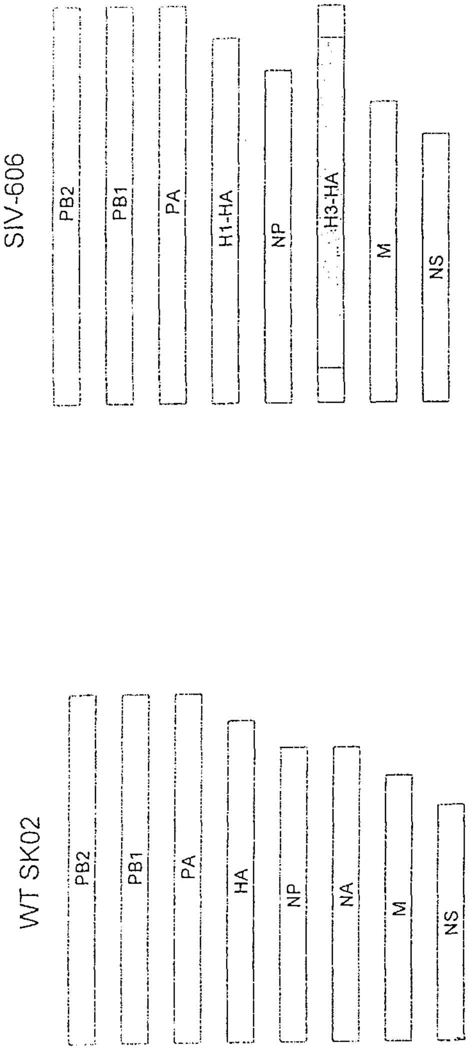
FIGS. 1A and 1B depict various influenza segments for use in the present invention.
Figure 1:
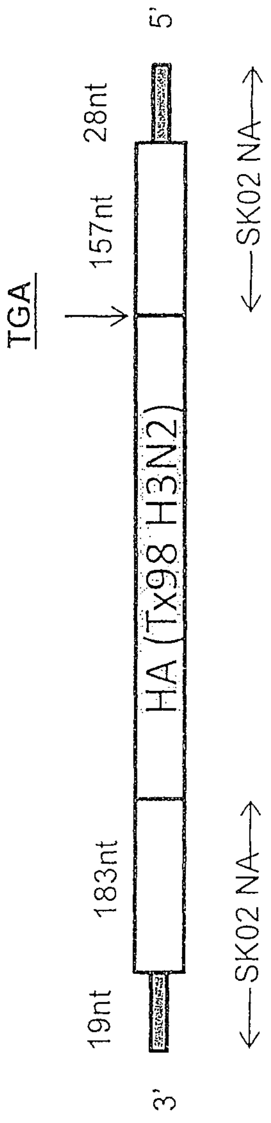

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology*, Current Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company); A. L. Lehninger, *Biochemistry* (Worth Publishers, Inc., current edition); Sambrook, et al., *Molecular Cloning: A Laboratory Manual* (current edition); *Methods In Enzymology* (S. Colowick and N. Kaplan eds., Academic Press, Inc.).

All publications, patents and patent applications cited herein, whether supra or infra, are hereby incorporated by reference in their entireties.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an influenza A virus" includes a mixture of two or more such viruses, and the like.

As used herein, the term "influenza virus" refers to members of the orthomyxoviridae family of enveloped viruses with a segmented antisense RNA genome (Knipe and Howley (eds.) Fields Virology, 4th edition, Lippincott Williams and Wilkins, Philadelphia, Pa., 2001). The term influenza virus may include any strain of influenza virus, such as influenza A, B, or C, which is capable of causing disease in an animal or human subject. In particular, the term encompasses any subtype of influenza A virus selected from H1-H15 and N1-N9, such as but not limited to H1N1, H1N2, H3N2, H3N1, H9N2 and H5N1, or any combination of H's and N's. A large number of influenza isolates have been partially or completely sequenced. See, e.g., the Influenza Sequence Database (ISD) (website at flu.lanl.gov; described by Macken et al., "The value of a database in surveillance and vaccine selection." in *Options for the Control of Influenza IV*. A. D. M. E. Osterhaus, N. Cox & A. W. Hampson (Eds.) Amsterdam: Elsevier Science, 2001, 103-106) and the GenBank database, particularly the Influenza Virus Resource (website at ncbi.nlm.nih.gov/genomes/FLU/FLU.html). The ISD and GenBank databases contain complete sequences for influenza A, B and C genome segments.

The term "derived from" is used herein to identify the original source of a molecule but is not meant to limit the method by which the molecule is made which can be, for example, by chemical synthesis or recombinant means.

An influenza virus molecule is a molecule derived from an influenza virus, including, without limitation, polypeptide, protein, polynucleotide, oligonucleotide, and nucleic acid molecules, as defined herein, from any of the various isolates of influenza subtypes A, B, or C. The molecule need not be physically derived from the particular isolate in question, but may be synthetically or recombinantly produced.

Nucleic acid and polypeptide sequences for a number of influenza virus isolates are known. Representative influenza sequences are presented in FIGS. 5-13 herein. Additional representative sequences, including additional sequences for the 8 influenza segments, including those segments coding for hemagglutinin (HA), neuraminidase (NA), polymerase acidic protein (PA), polymerase basic proteins 1 and 2 (PB1 and PB2), matrix membrane proteins 1 and 2 (M1 and M2), nucleoprotein (NP), and nonstructural proteins 1 and 2 (NS1 and NEP, also termed NS2) from influenza isolates found in various species are listed in the National Center for Biotechnology Information (NCBI) database and the Influenza Research Database found at fludb.org. See also Ferguson et al. (2003) *Nature* 422: 428-433; Lin et al. (2000) *Proc. Natl. Acad. Sci. U.S.A.* 97, 9654-9658; Nguyen et al. (2005) *J Virol.* 79:4201-4212; Ha et al. (2002) *EMBO J.* 21:865-875; and Chan et al. (2004) *J. Microbiol. Immunol. Infect.* 37:135-144; for sequence comparisons and a discussion of genetic diversity and phylogenetic analysis of influenza virus.

As used herein, the term "swine influenza virus" refers to a type A or type C influenza virus from the family orthomyxovirus that causes swine influenza. While orthomyxovirus has three groups: type A, type B and type C, only type A and type C influenza viruses infect pigs. Subtypes of swine influenza virus include H1N1, H1N2, H3N2, H3N1, H9N2 and H5N1. In certain embodiments, a swine influenza virus is an influenza virus that has been isolated from swine. For purposes of the present invention, a swine influenza virus is either a wild-type swine influenza virus or a recombinant, chimeric influenza virus derived from a wild-type swine influenza virus.

As used herein, the phrase "wild-type swine influenza virus" refers to the types of a swine virus that are prevalent, circulating naturally and producing typical outbreaks of disease. Examples of wild-type swine influenza viruses include, but are not limited to, A/swine/Saskatchewan/18789/02, A/Swine/Colorado/1/77, A/Swine/Colorado/23619/99, A/Swine/Cote d'Armor/3633/84, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P 12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/

17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/98, A/Swine/Wisconsin/458/98, A/Swine/Wisconsin/464/98 and A/Swine/Wisconsin/14094/99.

The term "HA gene" refers to the gene which encodes the hemagglutinin (HA) surface glycoprotein which projects from the lipid-containing envelope in influenza. HA is one of the molecules encoded by the segmented genome of influenza A and other viruses. A "swine influenza virus HA gene" is an HA gene isolated from a swine influenza virus, such as from any of the strains described above. The polynucleotide and amino acid sequences of representative swine HA genes can be found in public sequence databases such as GenBank. For example, HA genes from H1N1 and include, but are not limited to, GenBank Accession Nos. AY619961.1 (see FIGS. 5A and 5B); GQ457549.1; GQ457548.1; GQ457547.1; CY091769.1; CY091745.1; CY091737.1; CY091729.1; GU721143.3; JF820285.1; JF820277.1; JF707784.1; CY087136.1; CY087104.1; CY087096.1; CY087080.1; CY087072.1; CY087064.1; CY087056.1; CY087048.1; CY086863.1; CY086839.1; CY086353.1; CY086006.1; CY085990.1; CY085982.1; CY085974.1; CY085966.1; CY085958.1; CY085950.1; CY085942.1; CY085934.1; CY085926.1; CY085918.1; CY085910.1; CY085902.1; CY085894.1; CY085886.1; CY085878.1; CY085870.1; CY085854.1; CY085846.1; CY085838.1; CY085830.1; CY085822.1; CY085814.1; CY085806.1; CY085798.1; CY085790.1; CY085782.1; CY085774.1; CY085766.1; CY085758.1; CY085742.1; CY085726.1; CY085718.1; CY085710.1; CY085702.1; CY085694.1; CY085686.1; CY085670.1; JF833344.1; JF833343.1; JF833341.1; JF833339.1; JF833338.1; JF833337.1; JF833335.1; JF916682.1; JF812292.1; JF812291.1; JF812290.1; JF812287.1; JF812284.1; JF812281.1; JF812280.1; JF812279.1; JF812278.1; JF812273.1; JF812272.1; JF812271.1; AF091317.1; AF091315.1; AF091314.1.

HA genes from H3N2 and include, but are not limited to, the sequence shown in FIGS. 13A and 13B; as well as GenBank Accession Nos. AY377927.2; CY092324.1; AF153233.1; JN105973.1; HQ315643.1; FJ519977.1; FJ519976.1; FJ519975.1; FJ519974.1; FJ519973.1; FJ519972.1; FJ519971.1; GU937743.1; JF833345.1; JF833340.1; JF833336.1; JF833334.1; JF812293.1; JF812289.1; JF812277.1; JF812276.1; JF812275.1; JF812274.1; CY045575.1; CY045567.1; CY045559.1; CY045551.1; HQ825243.1; HQ825235.1; HQ825229.1; HQ825226.1; HQ825223.1; HQ825218.1; HQ825210.1; HQ825210.1; HQ825198.1; HQ825190.1; HQ825182.1; HQ825174.1; HQ825166.1; JF312065.1; JF312064.1; CY086920.1; JF312073.1; JF312072.1; JF312071.1; JF316643.1; JF263536.1; JF263535.1; HQ734204.1; HQ734201.1; HQ734198.1; HQ734195.1; HQ734192.1; HQ734189.1; HQ734186.1; CY077942.1; CY077934.1.

The term "NA gene" refers to the gene which encodes the neuraminidase (NA) surface glycoprotein which projects from the lipid-containing envelope in influenza. NA is one of the molecules encoded by the segmented genome of influenza A and other viruses. A "swine influenza virus NA gene" is an NA gene isolated from a swine influenza virus, such as from any of the strains described above. The polynucleotide and amino acid sequences of representative swine NA genes can be found in public sequence databases such as GenBank. For example, NA genes from H1N1 and include, but are not limited to, AY619960.1 (see FIGS. 6A and 6B); JF833356.1; JF833355.1; JF833353.1; JF833351.1; JF833350.1; JF833349.1; JF833355.1; JF833347.1; JF812315.1; JF812314.1; JF812313.1; JF812310.1; JF812307.1; JF812304.1; JF812303.1; JF812302.1; JF812301.1; JF812294.1; FJ791299.1; FJ791298.1; FJ791297.1; FJ791296.1; FJ791295.1; FJ791294.1; FJ791293.1; FJ791292.1; FJ791291.1; FJ791290.1; FJ791289.1; FJ791288.1; FJ791287.1.

The term "NA packaging signal" refers to the 3' and 5' viral RNA-specific packaging signals for NA that provide for efficient incorporation of viral RNA into viral particles. The packaging signals are present in the 5' and 3' untranslated regions (UTRs) and extend into the coding region of the NA segment. Preferably, the NA packaging signals used in the production of the recombinant, chimeric viruses will include only so much of the NA region sufficient for packaging and will not include the entire NA coding sequence. NA packaging signals are discussed in greater detail below.

As used herein, the phrase "multiplicity of infection" or "MOI" is the average number of virus per infected cell. The MOI is determined by dividing the number of virus added (ml added×PFU) by the number of cells added (ml added×cells/ml).

As used herein, the term "attenuated" means that an influenza virus variant, such as a recombinant, chimeric virus described herein, exhibits a measurable reduction in replication efficiency relative to wild-type influenza virus. The replication efficiency of an influenza virus may be determined, for example, by measuring plaque size in MDCK cells, by measuring virus titers over multiple growth cycles, or by isolating virus from infected lung tissue and measuring titers.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (recombinant virus, compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying molecules of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkyiphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region (s) from which the polynucleotide is derived. As such, it may represent either a sense or an antisense orientation of the original polynucleotide.

"Recombinant" as used herein to describe a nucleic acid molecule means a polynucleotide of genomic, RNA, cDNA, viral, semisynthetic, or synthetic origin which, by virtue of its origin or manipulation is not associated with all or a portion of the polynucleotide with which it is associated in nature. The term "recombinant" as used with respect to a virus, means a virus produced by manipulation of the viral genome.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant viruses and vectors or other transferred nucleic acid, and include the original progeny of the original cell which has been transfected.

A "coding sequence" or a sequence which "encodes" a selected polypeptide, is a nucleic acid molecule which is transcribed and translated into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, RNA or cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements" include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences. "Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. An expression cassette may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

The term "transfection" is used to refer to the uptake of foreign nucleic acid by a cell. A cell has been "transfected" when exogenous nucleic acid has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked nucleic acids.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., 1 Exp. Med. (1998) 187:1367-1371; Mcheyzer-Williams, M. G., et al, *Immunol. Rev.* (1996) 150:5-21; Lalvani, A., et al, *J. Exp. Med.* (1997) 186:859-865).

Thus, an immunological response as used herein may be one that stimulates the production of antibodies (e.g., neutralizing antibodies that block pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. *J. Clin Microbiol.* (1988) 26:231-235; Dreyer et al., *AIDS Res Hum Retroviruses* (1999) 15:1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells. are activated to, e.g., produce various cytokines, lymphokines and chemokines. Cells activated by an innate immune response include immature and mature Dendritic cells of the monocyte and plamsacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an antigenic molecule where administration of the composition to a subject results in the development in the subject of an immunological response as defined above.

An "antigen" refers to a molecule, such as a protein, polypeptide, or fragment thereof, or an attenuated virus, containing one or more epitopes (either linear, conformational or both) that will stimulate a host's immune-system to make an immunological response, as defined above. The term is used interchangeably with the term "immunogen." The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Similarly, an oligonucleotide or polynucleotide which expresses an antigen or antigenic determinant in vivo, such as in gene therapy and nucleic acid immunization applications, is also included in the definition of antigen herein.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

By "therapeutically effective amount" in the context of the immunogenic compositions is meant an amount of an immunogen, e.g., a recombinant, chimeric influenza virus, which will induce an immunological response, either for antibody production or for treatment or prevention of influenza virus infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

"Parenteral administration" refers to introduction into the body outside the digestive tract, such as by subcutaneous, intramuscular, intradermal or intravenous administration. This is to be contrasted with delivery to a mucosal surface, such as oral, nasal, vaginal or rectal. "Mucosal administration" refers to introduction into the body via any mucosal surface, such as intragastrically, pulmonarily, transdermally, intestinally, ocularly, intranasally, orally, vaginally, rectally, intratracheally or the like.

As used herein, "treatment" refers to any of (i) the prevention of infection or reinfection, as in a traditional vaccine, (ii) the reduction or elimination of symptoms, and (iii) the substantial or complete elimination of influenza virus from an infected individual. Treatment may be effected prophylactically (prior to infection) or therapeutically (following infection).

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention provides recombinant, chimeric swine influenza viruses which are attenuated with an impaired ability to replicate in vivo, methods for producing such attenuated swine influenza viruses, and the use of such viruses in vaccine and pharmaceutical formulations. Such viruses are capable of generating an immune response and creating immunity but either do not cause illness or cause fewer and/or less severe symptoms, i.e., the viruses have decreased virulence. Therefore, they are ideal candidates for live virus vaccines. Moreover, because HAs from different subtypes of SIVs are present, compositions including the chimeric influenza viruses can be used to provide broad coverage against a number of influenza strains.

In particular, the invention pertains to recombinant, chimera influenza viruses that include HA segments from more than one influenza subtype and include a deletion of all or part of the NA segment, immunogenic compositions comprising the viruses, as well as methods of stimulating an immune response against influenza virus, and methods of interfering with influenza virus replication.

In order to further an understanding of the invention, a more detailed discussion is provided below regarding the production of recombinant, chimeric influenza viruses and methods of using the same in compositions in the treatment and/or prevention of influenza virus infection.

A. Recombinant, Chimeric Influenza Viruses

Wild-type swine influenza viruses typically include an 8 segmented genome with the segments designated as follows:

| SEGMENT | GENE PRODUCT NAME |
|---|---|
| 1 | PB2 (Polymerase (basic) protein 2) |
| 2 | PB1 (Polymerase (basic) protein 1) |
| 3 | PA (Polymerase (acidic) protein) |
| 4 | HA (Hemagglutinin) |
| 5 | NP (Nucleoprotein) |
| 6 | NA (Neuraminidase) |
| 7 | M1 (Matrix protein 1); M2 (Matrix protein 2) |
| 8 | NS1 (Non-structural protein 1); NEP, also termed NS2 (Non-structural protein 2) |

The recombinant, chimeric influenza viruses described herein include two or more HA segments (segment 4) from two or more subtypes of influenza viruses. The recombinant influenza viruses can include HAs from any subtype of influenza virus and preferably from influenza A virus, selected from H1-H15 and N1-N9, such as but not limited to H1N2, H1N1, H3N2, H3N1, H9N2 and H5N1 or any combination of H's and N's. Particularly preferred are HA segments from viruses that infect pigs. The polynucleotide and amino acid sequences of representative swine HA genes can be found in public sequence databases such as GenBank. For example, HA genes from H1N1 and include, but are not limited to, GenBank Accession Nos. AY619961.1 (see FIGS. 5A and 5B); GQ457549.1; GQ457548.1; GQ457547.1; CY091769.1; CY091745.1; CY091737.1; CY091729.1; GU721143.3; JF820285.1; JF820277.1; JF707784.1; CY087136.1; CY087104.1; CY087096.1; CY087080.1; CY087072.1; CY087064.1; CY087056.1; CY087048.1; CY086863.1; CY086839.1; CY086353.1; CY086006.1; CY085990.1; CY085982.1; CY085974.1; CY085966.1; CY085958.1; CY085950.1; CY085942.1; CY085934.1; CY085926.1; CY085918.1; CY085910.1; CY085902.1; CY085894.1; CY085886.1; CY085878.1; CY085870.1; CY085854.1; CY085846.1; CY085838.1; CY085830.1; CY085822.1; CY085814.1; CY085806.1; CY085798.1; CY085790.1; CY085782.1; CY085774.1; CY085766.1; CY085758.1; CY085742.1; CY085726.1; CY085718.1; CY085710.1; CY085702.1; CY085694.1; CY085686.1; CY085670.1; JF833344.1; JF833343.1; JF833341.1; JF833339.1; JF833338.1; JF833337.1; JF833335.1; JF916682.1; JF812292.1; JF812291.1; JF812290.1; JF812287.1; JF812284.1; JF812281.1; JF812280.1; JF812279.1; JF812278.1; JF812273.1; JF812272.1; JF812271.1; AF091317.1; AF091315.1; AF091314.1.

HA genes from H3N2 and include, but are not limited to, GenBank Accession Nos. AF153233.1 (see FIGS. 13A and 13B); AY377927.2; CY092324.1; JN105973.1; HQ315643.1; FJ519977.1; FJ519976.1; FJ519975.1; FJ519974.1; FJ519973.1; FJ519972.1; FJ519971.1; GU937743.1; JF833345.1; JF833340.1; JF833336.1; JF833334.1; JF812293.1; JF812289.1; JF812277.1; JF812276.1; JF812275.1; JF812274.1; CY045575.1; CY045567.1; CY045559.1; CY045551.1; HQ825243.1; HQ825235.1; HQ825229.1; HQ825226.1; HQ825223.1; HQ825218.1; HQ825210.1; HQ825210.1; HQ825198.1; HQ825190.1; HQ825182.1; HQ825174.1; HQ825166.1; JF312065.1; JF312064.1; CY086920.1; JF312073.1; JF312072.1; JF312071.1; JF316643.1; JF263536.1; JF263535.1; HQ734204.1; HQ734201.1; HQ734198.1; HQ734195.1; HQ734192.1; HQ734189.1; HQ734186.1; CY077942.1; CY077934.1.

Any of the above HAs or other readily available HA sequences can be used with the subject invention.

Additionally, the recombinant, chimeric influenza viruses typically include a mutation in the NA genomic segment (segment 6) coding for neuraminidase such that replication of the virus is impaired. Mutations can include deletions, inversions, insertions or substitutions that impair replication of the virus. In certain embodiments, the virus variant comprises a deletion of all or part of the NA segment such that virus propagation is hindered. Because NA is essential for virus propagation, the function of NA can be provided in culture by growing the virus in the presence of sialidase. Preferably, NA packaging sequences at the 3' and optionally the 5' untranslated regions (UTRs) flanking the NA sequence and extending into the coding sequence are retained in the recombinant viruses.

In particular, specific cis-acting packaging signals exist in 3' and 5' (UTRs) that extend into the coding regions of most if not all segments, including the NA segment, which is responsible for viral release from infected cells by removing sialic acids from cellular glycoconjugates and viral glycoproteins. Each viral RNA consists predominantly of coding sequences (in antisense orientation), flanked at both ends by UTRs that range from 19 to 58 bases long. Within these UTRs, the distal 12 and 13 noncoding bases that form the extreme 3' and 5' termini, respectively, of every segment are highly conserved among viral strains and among the eight segments themselves. These distal conserved sequences are partially complementary to each other and can anneal to form a bulged duplex structure that is essential for transcription and replication of the segment. The UTRs harbor cis-acting signals that contribute to RNA packaging, since the attachment of authentic UTRs onto a heterologous RNA can enable it to be packaged into, and transduced by, influenza virus particles. Optimal packaging of at least some segments, such as NA, HA and NS requires not only both UTRs but also short portions of the coding region.

Deletion analysis of reporter constructs indicates that the minimal sequences needed for efficient packaging extend beyond each UTR to include 9 to 80 bases of adjacent coding sequence at either end of the segment (Fujii et al., *J. Virol.* (2005) 79:3766-3774; Fujii et al., *Proc. Natl. Acad. Sci. USA* (2003) 100:2002-2007; Watanabe et al., *J. Virol.* (2003) 77:10575-10583). Sequences at the 3' end of the coding region appear to exert a greater quantitative effect than those at the 5' end. These regions are therefore useful for packaging and maintaining wild-type NA RNA as well as mutant NA RNAs, e.g., RNAs with internal deletions and/or insertions. Accordingly, the recombinant, chimeric viruses of the invention will include at least packaging signals from the 3' UTR and a portion of the 3' NA coding region, and preferably will include packaging signals from both the 3' and 5' UTRs and 3' and 5' portions of the NA sequence.

Methods for locating packaging signals are known. In particular, Gog et al., *Nucl. Acids Res.* (2007) 35:1897-1907 found highly statistically significant clusters of codons with lower than expected synonymous variation within the influenza virus genome, located at the terminal regions of segments, where the presence of specific packaging signals are known. Synonymous mutational analysis of these regions confirmed the ability of their method to identify functionally significant cis-acting elements (i.e., packaging signals) in the virus genome at the single nucleotide level. Using these methods, then, packaging signals for the NA segment of various virus strains and subtypes can be readily identified. Determination of packaging efficiency of recombinant viral RNA segments can be carried out using techniques known in the art. See, e.g., Dos et al., *Virology* (2005) 341:34-46.

Generally, NA packaging sequences for use in the present invention will include at least 19 nucleotides from the 3' UTR adjacent to the NA coding sequence, preferably 19-30 nucleotides, such as 19, 20 . . . 25 . . . 30 . . . 35 nucleotides and at least 28 nucleotides from the 5' UTR adjacent to the NA coding sequence, preferably 28-50 nucleotides, such as 28, 29, 30 . . . 35 . . . 40 . . . 45 . . . 50 nucleotides. The NA packaging sequences also will include about 145 to 250, preferably 150-200 nucleotides from at least the 3' end of the coding sequence and optionally from each end of the coding region for the NA segment. Thus, for example, influenza virus packaging sequences can comprise sequences corresponding to the 3' end of NA viral RNA including sequences corresponding to the N-terminus of the NA coding region, e.g., at least 150 nucleotides of the 3' end of a type A NA viral RNA such as 150, 151, 152, 153, 154, 155 . . . 160 . . . 165 . . . 170 . . . 175 . . . 180 . . . 185 . . . 190, and so on, and, optionally, packaging sequences corresponding to the 5' end of NA viral RNA including sequences corresponding to the C-terminus of the NA coding region, e.g., 150, 151, 152, 153, 154, 155 . . . 160 . . . 165 . . . 170 . . . 175 . . . 180 . . . 185 . . . 190, and so on.

In one particular embodiment, a construct can be provided that includes an HA segment from one porcine influenza subtype and NA packaging sequences from another porcine influenza subtype located 3' and optionally 5' to the HA segment. As described in the examples, a construct was prepared that included an H3N2 HA flanked by H1N1 packaging sequences. This particular construct comprises an H3N2 HA sequence, flanked by 19 nucleotides from the 3' UTR adjacent to an H1N1 NA sequence and 183 nucleotides from the 3' NA coding region and 28 nucleotides from the 5' UTR adjacent to the NA sequence and 157 nucleotides from the 5' NA coding region. However, the remainder of the NA coding region is absent. Typically, the packaging sequences used are homologous to the backbone virus. Thus, if an H1N1 subtype is used as the backbone (i.e., all H1N1 segments are present in the recombinant virus except for all or a portion of the NA segment), NA packaging sequences from H1N1 will be retained and the remainder of the H1N1 NA sequence conveniently replaced with an HA sequence from a different subtype, such as an H3N2 HA sequence.

If desired, rather than a deletion, the NA coding region can be mutated such that virus propagation is hindered. The NA region can be mutagenized in vitro by the replacement of the appropriate nucleotides to result in the desired amino acid changes. Such a change can include as little as one nucleotide, effecting a change in a single amino acid, or can encompass several nucleotide changes. Mutants can be produced by standard methods of site-directed mutagenesis. The mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468; Wu (Ed.), Meth. In Enzymol. Vol. 217, San Diego: Academic Press (1993); Kunkel (1985) Proc. Natl. Acad. Sci. USA, 82:488-492; all of which are incorporated herein by reference.

The NA mutation (e.g., deletion of all or a portion of the NA coding sequence except the sequences harboring packaging signals) is preferably one that hinders virus propagation. The replication efficiency of an attenuated influenza virus may be determined, for example, by measuring plaque size in Madin-Darby canine kidney (MDCK) cells, by measuring virus titers over multiple growth cycles, or by isolating virus from infected lung tissue and measuring titers. For example, an attenuated swine influenza virus of the invention permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 2 to approximately 90 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type swine influenza virus in cell culture, e.g. MDCK cells; cells of a human (e.g., PerC6, a producer cell line derived from human embryonic retinoblasts transformed with the E1 region of Adenovirus 5); mouse; chicken (e.g., chicken embryo fibroblasts); rat, birds; or pig (e.g., PK(D1) cells, PK(15) cells, PK13 cells, NSK cells, LLC-PK1 cells, LLC-PK1A cells, ESK-4 cells, ST cells, PT-K75 cells, PK-2a/CL 13 or SJPL cells). Replication efficiency can be determined by a hemagglutination assay of BALF from pigs or supernatants of pig cells approximately 2 to 10 days, 3 to 7 days, 3 to 5 days, or 2, 3, 5, 6, 7, 8, 9, 10 days post-infection or when the viruses are plagued on MDCK cells. In one embodiment, the growth of an attenuated swine influenza virus of the invention is compared to a particular standard or reference, e.g., wild-type swine influenza virus A/Swine/Texas/4199-2/98. Another measure of attenuation is to grow the virus in the absence of sialidase and measure titers as compared to a reference wild-type strain as above.

In addition to the HA sequences, and the packaging sequences described above, the recombinant, chimeric influenza virus will also include the remaining viral segments, segments 1-3, 5, 7 and 8, that is, segments encoding PB2 (segment 1), PB1 (segment 2), PA (segment 3), NP (segment 5), M1 and M2 (segment 7), NS1 and NEP (segment 8). Nucleic acid and polypeptide sequences for these segments, as well as segments 4 (encoding HA) and 6 (encoding NA) from a number of influenza virus isolates are known. Representative influenza sequences are presented in FIGS. 5-13 herein. Additional representative sequences for the 8 influenza segments from influenza isolates found in various species are listed in the National Center for Biotechnology Information (NCBI) database and the Influenza Research Database found at fludb.org. See also Ferguson et al. (2003) *Nature* 422: 428-433; Lin et al. (2000) *Proc. Natl. Acad. Sci. U.S.A.* 97, 9654-9658; Nguyen et al. (2005) *J. Virol.* 79:4201-4212; Ha et al. (2002) *EMBO J.* 21:865-875; and Chan et al. (2004) *J. Microbiol. Immunol. Infect.* 37:135-144; for sequence comparisons and a discussion of genetic diversity and phylogenetic analysis of influenza virus.

Any of these sequences, as well as variants thereof can be used to produce the recombinant, chimeric influenza viruses. Thus, the invention includes variants of the above sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

The above-described segments can be derived from any of various swine influenza viruses, including, without limitation, A/swine/Saskatchewan/18789/02, A/Swine/Colorado/1/77, A/Swine/Colorado/23619/99, A/Swine/Cote d'Armor/3633/84, A/Swine/Cote d'Armor/3633/84, A/Swine/England/195852/92, A/Swine/Finistere/2899/82, A/Swine/Hong Kong/10/98, A/Swine/Hong Kong/9/98, A/Swine/Hong Kong/81/78, A/Swine/Illinois/100084/01, A/Swine/Illinois/100085A/01, A/Swine/Illinois/21587/99, A/Swine/Indiana/1726/88, A/Swine/Indiana/9K035/99, A/Swine/Indiana/P 12439/00, A/Swine/Iowa/30, A/Swine/Iowa/15/30, A/Swine/Iowa/533/99, A/Swine/Iowa/569/99, A/Swine/Iowa/3421/90, A/Swine/Iowa/8548-1/98, A/Swine/Iowa/930/01, A/Swine/Iowa/17672/88, A/Swine/Italy/1513-1/98, A/Swine/Italy/1523/98, A/Swine/Korea/CY02/02, A/Swine/Minnesota/55551/00, A/Swine/Minnesota/593/99, A/Swine/Minnesota/9088-2/98, A/Swine/Nebraska/1/92, A/Swine/Nebraska/209/98, A/Swine/Netherlands/12/85, A/Swine/North Carolina/16497/99, A/Swine/North Carolina/35922/98, A/Swine/North Carolina/93523/01, A/Swine/North Carolina/98225/01, A/Swine/Oedenrode/7C/96, A/Swine/Ohio/891/01, A/Swine/Oklahoma/18717/99, A/Swine/Oklahoma/18089/99, A/Swine/Ontario/01911-1/99, A/Swine/Ontario/01911-2/99, A/Swine/Ontario/41848/97, A/Swine/Ontario/97, A/Swine/Quebec/192/81, A/Swine/Quebec/192/91, A/Swine/Quebec/5393/91, A/Swine/Taiwan/7310/70, A/Swine/Tennessee/24/77, A/Swine/Texas/4199-2/98, A/Swine/Wisconsin/125/97, A/Swine/Wisconsin/136/97, A/Swine/Wisconsin/163/97, A/Swine/Wisconsin/164/97, A/Swine/Wisconsin/166/97, A/Swine/Wisconsin/168/97, A/Swine/Wisconsin/235/97, A/Swine/Wisconsin/238/97, A/Swine/Wisconsin/457/98, A/Swine/Wisconsin/458/98, A/Swine/Wisconsin/464/98 and A/Swine/Wisconsin/14094/99.

In one particular embodiment, an H3N2 HA is used in place of all or part of an H1N1 NA sequence in an H1N1 backbone. Thus, the resulting recombinant virus includes two, HAs and the remainder of the viral segments. See, FIG. 1.

Each of the above described segments can be isolated from viral RNA using known methods. For example, nucleic acids can be obtained by screening cDNA and/or genomic libraries from cells infected with virus, or by deriving the gene from a vector known to include the same. For example, polynucleotides of interest can be isolated from a genomic library derived from viral RNA from an infected subject. Alternatively, influenza virus can be isolated from infected mammals or from biological samples (e.g., nasal, nasopharyngeal, throat, or conjunctival secretions, blood, or anal swabs) collected from infected subjects. Once obtained, the virus can be propagated using known techniques, such as described in Mochalova et al., *Virology* (2003) 313:473-480; Lin et al., *Virology* (1997) 233:402-410; Hardy et al., *Virology* (1995) 211:302-306; Hinshaw et al., *J. Gen. Virol.* (1978) 41:115-127. Nucleic acid can also be obtained directly from the influenza virus in question.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) Proc. Natl. Acad. Sci. USA 88:4084-4088. Additionally, oligonucleotide directed synthesis (Jones et al. (1986) Nature 54:75-82), oligonucleotide directed mutagenesis of pre-existing nucleotide regions (Riechmann et al. (1988) Nature 332:323-327 and Verhoeyen et al. (1988) Science 239:1534-1536), and enzymatic filling-in of gapped oligonucleotides using $T_4$ DNA polymerase (Queen et al. (1989) Proc. Natl. Acad. Sci. USA 86:10029-10033) can be used to produce modified molecules.

An amplification method such as PCR can be used to amplify polynucleotides including the various segments. In one embodiment, these segments are reverse-transcribed into cDNA and amplified using RT-PCR. See, e.g., Hoffmann et al., *Proc. Natl. Acad. Sci. USA* (2000) 97:6108-6113. The cDNA from each segment is cloned to provide separate plasmids for use in preparing the recombinant, chimeric influenza virus. In some embodiments, cloning vector pHW2000 (Hoffmann et al., *Proc. Natl. Acad. Sci. USA* (2000) 97:6108-6113) can be used. However, the segments can be cloned into any suitable vector. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

The recombinant, chimeric, attenuated influenza virus comprising more than one HA sequence from more than one influenza subtype can then be produced by any method well know in the art. Preferably reverse genetics is used to produce the recombinant viruses. Reverse genetics uses RNA polymerase complexes isolated from influenza virus-infected cells to transcribe artificial influenza virus genome segments containing the mutation(s). The synthesized RNA segment(s) are incorporated into virus particles using a helper virus, and viruses containing the desired changes are then selected. Reverse genetics methods for influenza viruses are described, for example, in Enami et al., *Proc. Natl. Acad. Sci.* (1990) 87:3802 3805; Enami and Palese, *J. Virol.* (1991) 65:2711-13; Luytjes, *Cell* (1989) 59:1107-13; Fodor et al., *J. Virol.* (1999) 73:9679-9682; Gao et al., *J. Virol.* (2008) 82:6419-6426; Quinlivan et al., *J. Virol.* (2005) 79:8431-8439; and U.S. Pat. Nos. 5,578,473, 6,974,686 and 7,037,707, all of which are incorporated herein by reference in their entireties.

Recently developed reverse-genetics systems, based entirely on cDNA, have allowed the manipulation of the influenza viral genome. See, e.g, Palese et., *Proc. Natl. Acad. Sci. USA* (1996) 93:11354; Neumann and Kawaoka, *Adv. Virus Res.* (1999) 53:265; Neumann et al., *Proc. Natl. Acad. Sci. USA* (1999) 96:9345; Fodor et al., *J. Virol.* (1999) 73:9679, incorporated by reference in their entireties. In one technique, modified viral RNA transcripts are transcribed in vitro from cDNA constructs in the presence of purified NP, PB1, PB2, and PA proteins. The resulting synthetic RNP is then transfected into cells previously infected with an influenza helper virus. This helper virus usually has a conditional growth defect, such as host range restriction or temperature sensitivity, which allows the subsequent selection of transfectant viruses. For example, host-range helper viruses have been successfully used to rescue synthetic NA and PB2 genes. See Enami, supra, and Subbarao, *J Virol* (1993) 67:7223-28.

In preferred embodiments, an eight plasmid system is used to generate attenuated influenza viruses. See, e.g., Hoffmann et al., *Vaccine* (2002) 20:3165-3170; Hoffmann et al., *Proc. Natl. Acad. Sci. USA* (2000) 97:6108-6113; and U.S. Patent Publication No. 20040029251, incorporated herein by reference in their entireties. In this embodiment, the plasmids harboring the eight segments of the desired influenza virus, such as the two HA segments, as well as segments encoding polymerase acidic protein (PA), polymerase basic proteins 1 and 2 (PB1 and PB2), the matrix (M) segment encoding matrix proteins 1 and 2 (M1 and M2), the nucleoprotein (NP), and the nonstructural (NS) segment encoding nonstructural proteins 1 and 2 (NS1 and NEP), are cotransfected into an appropriate cell resulting in the recombinant, chimeric virus described herein. See also, U.S. Pat. No. 6,951,754 that describes eight plasmid dual promoter reverse genetic systems for the production of attenuated influenza viruses using a pol I-pol II system, incorporated herein by reference in its entirety.

Production of live attenuated virus vaccine formulations is accomplished using conventional methods involving propagation of the recombinant, chimeric virus in any substrate that allows the virus to grow to titers sufficient for further use. Typically, the viruses are propagated in cells, embryonated eggs, and/or animals followed by purification. Generally, influenza viruses are grown in embryonated chicken eggs or mammalian cells, such as Madin-Darby canine kidney (MDCK) cells, Madin Darby bovine kidney (MDBK) cells, pig cells, or African green monkey kidney (Vero) cells, using known techniques. See, e.g., Mochalova et al., *Virology* (2003) 313:473-480; Lin et al., *Virology* (1997) 233:402-410; Hardy et al., *Virology* (1995) 211:302-306; Hinshaw et al., *J Gen. Virol.* (1978) 41:115-127. Representative pig cells include porcine kidney cell lines, porcine testis cell lines and porcine lung cell lines, such as but not limited to, PK(D1) cells, PK(15) cells, PK13 cells, SJPL cells, NSK cells, LLC-PK1 cells, LLC-PK1A cells, ESK-4 cells, ST cells, PT-K75 cells, and PK-2a/CL 13 cells.

In another embodiment, the recombinant, chimeric swine influenza viruses are propagated in chicken cells, e.g., chicken embryo fibroblasts derived from, e.g., 6-14 day-old embryonated eggs. In other embodiments, young or immature embryonated eggs can be used to propagate the viruses of the invention. Immature embryonated eggs encompass eggs which are less than ten-day-old eggs. Immature embryonated eggs may also be eggs which artificially mimic immature eggs as a result of alterations to the growth conditions, e.g., changes in incubation temperatures; treating with drugs; or any other alteration which results in an egg with a retarded development. The swine influenza viruses can be propagated in different locations of the embryonated egg, e.g., the allantoic cavity.

In a specific embodiment, the attenuated swine influenza viruses of the present invention are propagated in any substrate that allows the virus to grow to titers comparable to those determined for wild type swine influenza virus strains. Preferably, the virions are cultured in the presence of sialidase since the NA segment in the recombinant, chimeric virus is deficient.

It is preferred that the virus is highly purified prior to vaccine formulation. Generally, the purification procedures will result in the extensive removal of cellular DNA, other cellular components, and adventitious agents. Procedures that extensively degrade or denature DNA can also be used. See, e.g., Mizrahi, ed., Viral Vaccines, Wiley-Liss, New York (1990). Methods of purification are known in the art and may include one or more of, for instance, gradient centrifugation, ultracentrifugation, zonal ultracentrifugation, continuous-flow ultracentrifugation and chromatography, such as ion exchange chromatography, size exclusion chromatography, and liquid affinity chromatography, polyethylene glycol or ammonium sulfate precipitation.

B. Anti-Viral Compositions

The recombinant, chimeric influenza viruses, as well as recombinant, chimeric influenza viruses that have been subsequently inactivated, can be formulated into compositions for delivery to subjects for either inhibiting infection, or for enhancing an immune response to influenza virus. Thus, either a live recombinant swine influenza virus vaccine or immunogenic formulation or an inactivated recombinant swine influenza virus vaccine or immunogenic formulation can be formulated. A live vaccine or immunogenic formulation may be preferred because multiplication in the host leads to a prolonged stimulus of similar kind and magnitude to that occurring in natural infections, and therefore, confers substantial, long-lasting immunity. Production of such live recombinant swine influenza virus vaccine formulations and immunogenic formulations may be accomplished using conventional methods involving propagation as described above. When formulated as a live virus vaccine, a range of about $10^2$ to $10^8$ can be used, preferably from about $10^3$ to $10^7$, more preferably $10^4$ pfu to about $5\times10^6$, and most preferably from $10^4$ to $10^7$ pfu per dose should be used.

Inactivated vaccine formulations may be prepared using conventional techniques to "kill" the attenuated viruses. Inactivated vaccines are "dead" in the sense that their infectivity has been destroyed. Ideally, the infectivity of the virus is destroyed without affecting its immunogenicity. In order to prepare inactivated vaccines, the attenuated virus is grown and purified as described above. The purified virus is then inactivated using one of several methods known in the art. Such methods include both chemical or physical means. Chemical means for inactivating an influenza virus include treatment of the virus with an effective amount of one or more of the following agents: detergents, formaldehyde, formalin, β-propiolactone, or UV light. Other methods of viral inactivation are known in the art, such as for example binary ethylamine, acetyl ethyleneimine, or gamma irradiation. See, e.g., U.S. Pat. Nos. 6,635,246; 5,891,705; 5,106,619; and 4,693,981, incorporated herein by reference in their entireties.

Compositions of the invention may comprise or be coadministered with a non-influenza antigen or combination of antigens, such as with a combination influenza vaccine. Methods of preparing such formulations are described in, e.g., *Remington's Pharmaceutical Sciences*, Mack Publishing Company, Easton, Pa., 18 Edition, 1990. The compositions of the present invention can be prepared for mucosal delivery, parenteral delivery, e.g., as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

If used to modulate an immune response, additional adjuvants which enhance the effectiveness of the composition may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

Carriers may also be used in order to increase the immunogenicity of the vaccine. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

Furthermore, influenza molecules may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Formulations will contain a "therapeutically effective amount" of the active ingredient, that is, an amount capable of achieving the desired response in a subject to which the composition is administered. In the treatment and prevention of influenza infection, for example, a "therapeutically effective amount" would preferably be an amount which prevents, reduces or ameliorates the symptoms of flu. The exact amount necessary will vary depending on the subject being treated; the age and general condition of the subject to be treated; the capacity of the subject's immune system to synthesize antibodies; the degree of protection desired; the severity of the condition being treated; the particular virus preparation selected and its mode of administration, among other factors. An appropriate effective amount can be readily determined by one of skill in the art. Thus, a "therapeutically effective amount" will fall in a relatively broad range that can be determined through routine trials. The recombinant, chimeric influenza virus will typically range from about 1% to about 95% (w/w) of the composition, or even higher or lower if appropriate.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and HYTREL copolymers, swellable polymers such as hydrogels, resorbable polymers such as collagen and certain polyacids or polyesters such as those used to make resorbable sutures, polyphosphazenes, alginate, microparticles, gelatin nanospheres, chitosan nanoparticles, and the like. The influenza virus can also be delivered using implanted mini-pumps, well known in the art.

C. Administration

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by intratracheal, rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration. Immunogenic compositions can also be administered topically by direct transfer to the surface of the skin. Topical administration can be accomplished without utilizing any devices, or by contacting naked skin with the immunogenic composition utilizing a bandage or a bandage-like device (see, e.g., U.S. Pat. No. 6,348,450).

Preferably the mode of administration is parenteral, mucosal or a combination of mucosal and parenteral immunizations. Even more preferably, the mode of administration is parenteral, mucosal or a combination of mucosal and parenteral immunizations in a total of 1-2 vaccinations 1-3 weeks apart. Preferably the route of administration includes but is not limited to oral delivery, intramuscular delivery and a combination of oral and intramuscular delivery.

In one embodiment, the method for treating an infection by an influenza virus, comprises mucosally administering to a subject in need thereof a first immunogenic composition comprising the influenza viruses of the invention followed by parenterally administering a therapeutically effective amount of a second immunogenic composition comprising the influenza viruses of the invention.

The immunogenic composition may be used to elicit systemic and/or mucosal immunity, preferably to elicit an enhanced systemic and/or mucosal immunity. Preferably the immune response is characterized by the induction of a serum IgG and/or an IgA immune response.

In any method involving coadministration, the various compositions can be delivered in any order. Thus, in embodiments including delivery of multiple different compositions or molecules, the influenza virus need not be delivered prior to other immunogenic substances. For example, the priming step may include delivery of one or more polypeptides and the boosting may comprise delivery of one or more attenutated influenza viruses. Multiple administrations of influenza virus can be followed by multiple administrations of other substances. Administrations can be performed in any order. Therefore, any combination of influenza virus and other immunogenic substances can be used to elicit an immune reaction.

D. Dosage Regime

Dosage treatment can be according to a single dose schedule or a multiple dose schedule. Multiple doses may be used in a primary immunization schedule and/or in a booster immunization schedule. In a multiple dose schedule, the various doses may be given by the same or different routes, e.g. a parenteral prime and mucosal boost, a mucosal prime and parenteral boost, etc.

Preferably the dosage regime enhances the avidity of the antibody response leading to antibodies with a neutralizing characteristic. An in vitro neutralization assay may be used to test for neutralizing antibodies (see for example Asanaka et al., *J. of Virol.* (2005) 102:10327; Wobus et al., *PLOS Biology* (2004) 2; e432; and Dubekti et al., *J. Med. Virol.* (2002) 66:400).

E. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the antigens in the compositions of the invention after administration of the composition.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum specific antibody responses are determined post-immunization but pre-challenge whereas mucosal specific antibody body responses are determined post-immunization and post-challenge.

The immunogenic compositions of the present invention can be evaluated in in vitro and in vivo animal models prior to host administration. The efficacy of immunogenic compositions of the invention can be determined in vivo by challenging animal models of infection, e.g., guinea pigs or mice or pigs, with the immunogenic compositions. The immunogenic compositions may or may not be derived from the same strains as the challenge strains. Preferably the immunogenic compositions are derivable from the same strains as the challenge strains. Particularly useful mouse models include those in which intraperitoneal immunization is followed by either intraperitoneal challenge or intranasal challenge. In vivo efficacy mouse models include but are not limited to a murine infection model using swine strains and a murine disease model which is a murine model using a mouse-adapted strain, such as strains which are particularly virulent in mice.

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens. By way of example, evidence of neutralizing antibodies in patient blood samples is considered as a surrogate parameter for protection since their formation is of decisive importance for virus elimination in TBE infections (see Kaiser and Holzmann, Infection 28; 78-84).

F. Kits

The invention also provides kits comprising one or more containers of compositions of the invention. Compositions can be in solid form, liquid form or can be lyophilized. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

For mucosal routes, the composition may be packaged for intranasal administration, such as by nasal spray, nasal drops, gel or powder. See, e.g., Almeida & Alpar, *J. Drug Targeting* (1996) 3:455-467; Agarwal & Mishra, *Indian J. Exp. Biol.* (1999) 37:6-16 or in inhalation devices well known in the art.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Generation of a Recombinant Virus Including Both H1 and H3 HAs

A recombinant, chimeric influenza A virus possessing, an eight segmented genome, was produced as detailed below. The virus included seven segments of a swine H1N1 virus with the majority of the NA segment replaced by an H3 HA coding region sequence flanked by NA packaging sequences. The virus thus included HAs from two different types of swine influenza, H1 HA and H3 HA. Because NA is essential for virus propagation, the function of NA was provided by growing the virus in the presence of sialidase (neuraminidase).

In particular, in order to generate a recombinant swine influenza virus carrying two different HA molecules, the NA segment in an H1N1 swine influenza virus, A/swine/Saskatchewan/18789/02, termed "SIV SK02" herein (obtained from the Prairie Diagnostic Services, Western College of Veterinary Medicine, University of Saskatchewan, Canada) was replaced with an H3 HA segment from the H3N2 Influenza A virus, A/Swine/Texas/4199-2/98 (termed "SIV Tx98" herein) (FIG. 1A). The H3 HA open reading frame (ORF) derived from SIV-Tx98 was flanked by NA packaging signals that included 202nt at the 3' end (19nt from the 3' UTR and 183nt from the 3' NA coding region) and 185nt at the 5' end (28nt from the 5' UTR and 157nt from the 5' NA coding region) from SIV-SK02 (H1N1) strain (FIG. 1B). Plasmid pHW-SIV-NA-H3HA encoding H3 HA flanked by NA packaging signals was constructed by modifying an original plasmid pHW-SIV/SK-NA. Briefly, the NA segment-specific packaging signals at 3' and 5' ends (202nt and 185nt respectively), were amplified by polymerase chain reaction (PCR) using pHW-SIV/SK-NA as template and the following sets of primers: for amplifying 3' NA packaging signal, 5'-TAATACGACTCACTATAGGG-3' (SEQ ID NO:21) and 5'-GTCATTTCCGGGAAGTTTTTGCACCCAAGTATTGTTTTCGTAG-3' (SEQ ID NO:22) were used; for amplifying 5' NA packaging signal, 5'-GCTGAAATCAGGATACAAAGATTGAGGCCTTGCTTCTGGGTTG-3' (SEQ ID NO:23) and 5'-ACAGGTGTCCGTGTCGCG-3' (SEQ ID NO:24) were used. H3 HA ectodomain (excluding signal peptide sequence) from SIV/Tx98 was amplified by PCR using pHW-Tx98 HA as a template and 5'-CTACGAAAACAATACTTGGGTGCAAAAACTTCCCGGAAATGAC-3' (SEQ ID NO:25) and 5'-CAACCCAGAAGCAAGGCCTCAATCTTTGTATCCTGATTTCAGC-3' (SEQ ID NO:26) as primers. The three pieces of PCR products were joined together by overlapping PCR. Finally, this PCR product was digested by NaeI/NheI and replaced the corresponding segment in pHW-SIV/SK-NA. The constructed plasmid was DNA-sequenced to ensure that additional mutations were not introduced during the overlapping PCRs.

This construct was inserted into cloning vector pHW2000 (Hoffmann et al., *Proc. Natl. Acad. Sci. USA* (2000) 97:6108-6113) to render plasmid-606. Cloning vector pHW2000 contains 225 bp of the human pol I promoter and 33 bp of the murine terminator sequence separated by two BsmB1 sites. The pol I promoter and terminator elements are flanked by a truncated immediate-early promoter of human cytomegalovirus and by the gene encoding bovine growth hormone.

The pHW2000 vector was cotransfected with plasmid-606 and seven plasmids which included the PB2, PB1, PA, HA, NP, M and NS segments from SIV-SK02 strain as described in Masic et al., *J. Gen. Virol.* (2009) 90:375-385, in the presence of 10 mU/ml of *vibrio cholera* sialidase which resulted in successful rescuing of a recombinant, chimeric virus termed "SIV/SK-606 or SIV-606" This SIV/H1H3 SIV mutant virus was rescued using an 8-plasmid reverse genetics system described by Hoffmann et al., *Proc. Natl. Acad. Sci. USA* (2000) 97:6108-6113. Briefly, 293T and MDCK cells were co-cultured at the same density ($2.5\times10^5$ cells/well) in a 6-well plate and maintained in DMEM containing 10% FBS at 37° C., 5% $CO_2$ for 24 hrs. One hour prior to transfection, medium containing FBS was replaced with fresh Opti-MEM (Invitrogen). To rescue SIV/SK-606, cells were transfected with eight plasmid constructs (pHW-SIV/SK-PB2, pHW-SIV/SK-PB1, pHW-SIV/SK-PA, pHW-SIV/SK-HA, pHW-SIV/SK-NP, pHW-SIV-NA-H3HA, pHW-SIV/SK-M and pHW-SIV/SK-NS) by Transit-LT1 transfection reagent (Minis, Madison, Wis.). Six hours later, the transfection mixture was replaced with 1 ml of fresh Opti-MEM. Twenty four hours post-transfection, one ml of Opti-MEM containing 0.4% BSA, 2 μg/ml of TPCK-treated trypsin and 10 mU/ml *Vibrio cholerae* neuraminidase (Sigma, N6514) was added to transfected cells. Supernatant was collected at 96 hours post transfection. Cytopathogenic effect (CPE) was observed after the third consecutive passage on MDCK cells and virus presence was confirmed by a hemagglutination test.

Example 2

Characterization of SIV/SK-606

To confirm that recombinant virus SIV/SK-606 possessed both H1 and H3 HA segments in its genome, viral RNA was isolated from purified virons. Briefly, tissue culture grown viruses were collected by ultracentrifugation and subjected to a sucrose gradient centrifugation (Masic et al., *J. Gen. Virol.* (2009) 90:375-385). For RNA purification, purified virions were processed following manufacturer's instruction of Trizol (Invitrogen). Reverse transcription was performed using the Uni12 primer (Hoffman et al., *Arch. Virol.* (2001) 146:2275-2289) which specifically amplifies viral RNAs. PCR was carried out by using primers specific for H1 (Fw 5' TGGCCAAACCATGAGACAAC 3' (SEQ ID NO:27) and Bw 5' GGCGTTATTCCTCAGTTGTG 3' (SEQ ID NO:28)) and H3 HAs (Fw 5' CGCAATCGCAGGTTTCATAG 3' (SEQ ID NO:29) and Bw 5' CAACCCAGAAGCAAGGCCTCAATCTTTGTATCCTGATTTCAGC 3' (SEQ ID NO:30)).

While PCR products representing the H1 HA segment were detected only in the SK02 and the SIV-606 genomes, PCR bands representing the H3 HA segment were observed in Tx98 and SIV-606 viral RNA extraction. These data demonstrated that the genome of SIV-606 included both H1 and H3 HA segments.

To examine whether both HAs were expressed, viral infected cell lysates were subjected to Western blotting analysis using antibodies specific for H1HA, H3HA and M1. Briefly, MDCK cells were infected with wild-type SIV/SK02, wild-type SIV/Tx98, or SIV-606 at an MOI of 0.01. At 48 hours post-infection, cell lysates were prepared and were subjected to Western blotting analysis using antibodies specific for H1 HA (Anti-HA (A/California/06/2009 ((H1N1) monoclonal antibody, eEnzyme (Maryland, USA), H3 HA (Anti-multi-Hemagglutinins (H3N2) Antibody, rabbit IgG, eEnzyme (Maryland, USA) and M1 (Shin et al., *J Gen Virol* (2007) 88:942-950).

M1 protein was detected in all virus infected cells, however, H1 HA was seen only in SK02 and SIV-606 infected cells and H3 HA was seen in Tx98 and SIV-606 samples. Together, these data demonstrate that the H3 segment was incorporated into the genome of SIV-606 and both HAs were expressed.

To observe the morphology of the recombinant virus, negative staining transmission electron microscopy was performed. The majority of virions exhibited spherical enveloped particles of approximately 100 nm in diameter, which resembled the morphology of the wild type virus.

Figure 2:
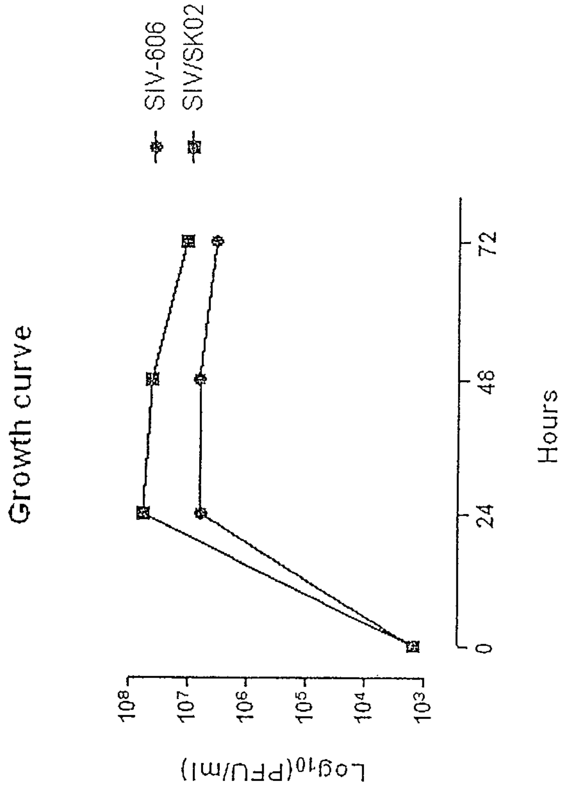
FIG. 2 shows the growth curves of SIV-606 and SIV/SK02.

The replication potential of the SIV-606 was investigated in MDCK cells. In the presence of sialidase, SIV-606 formed plaques similar in size as wild-type virus. In contrast, SIV-606 did not grow in the absence of sialidase, indicating that replication of the recombinant virus was dependent on sialidase. The growth potential and kinetics of SIV-606 were also determined. As shown in FIG. 2, SIV-606 reached a plateau at 24 h.p.i. as did the wild-type virus. SIV-606 grew to a titer of $7\times10^6$ PFU/ml, which was approximately 1 log lower than wild-type virus. These results indicated that although SIV-606 had a slightly lower titer, it grew to relatively high titer in cell culture, which enables propagation of the virus.

Example 3

Pathogenicity of SIV-606 in Pigs

Figure 3:
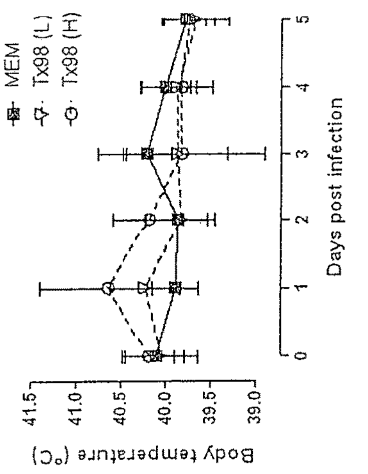
FIGS. 3A-3C show the body temperature of pigs infected with high and low doses of SK02 (FIG. 3A), Tx98 (FIG. 3B) and SIV-606 (FIG. 3C).
Figure 3:
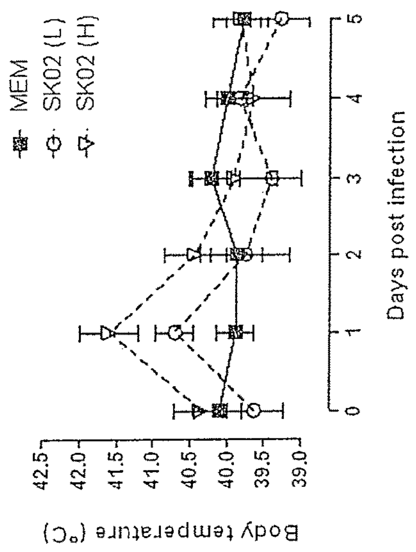
Figure 3:
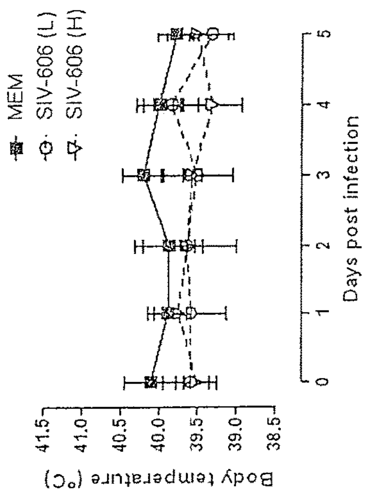
Figure 4:
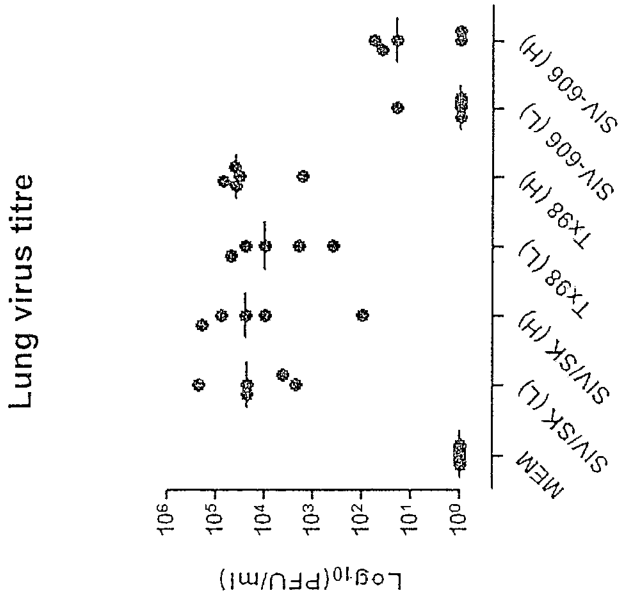
FIG. 4 shows the lung virus titers of pigs infected with high and low doses of SIV/SK02, SIV Tx98 and SIV-606.

The pathogenicity of SIV-606 was evaluated in pigs. Thirty-five 4-week old SIV-negative pigs were split randomly into seven groups of five pigs. These were infected intratracheally with 4 ml MEM containing $1\times10^5$ or $1\times10^6$ PFU/ml SK02 WT, SIV-606 or Tx98. The animals in the control group were mock infected with medium only (Table 1). Rectal temperature was monitored daily. On day 5 post infection pigs were euthanized and necropsies were performed. As shown in FIGS. 3A-3C, pigs infected with wild-type viruses had an increased temperature on day 1 post infection, and the temperature decreased gradually on the following days. However, pigs infected by SIV-606 did not show elevated temperatures compared to the control group. At necropsy, the macroscopic lung lesions were documented. The mock, SIV-606 high dose- and low dose-infected pigs did not show any typical macroscopic lung lesions. In contrast, gross lesions characterized as purple- to plum-colored consolidated areas were observed in cardiac lobes of pigs infected by SK02 and Tx98 with high and low doses. In agreement with these results, SK02 wild type virus could be recovered from lung tissue of all animals infected with low and high doses of SK02 with median titers of $2.4\times10^4$ PFU/ml and $2.6\times10^4$ PFU/ml respectively. Similarly, wild type virus could be isolated from lung tissue of all pigs infected with Tx98 virus with median titers of $1\times10^4$ PFU/ml and $3.4\times10^4$ PFU/ml in low and high dose groups. However, SIV-606 virus was only detected from one pig in the low dose group and 3 pigs from the high dose group with a very low titer (median titers were 0 and 20 PFU/ml respectively). These results demonstrated that the SIV-606 virus is highly attenuated in pigs and thus can be used as a live, attenuated vaccine for swine influenza.

TABLE 1

Assignment of pigs, dose and route of virus infection

| Group N = 5 | Inoculum | Concentration | Dose Volume | Route |
|---|---|---|---|---|
| 1 | MEM | | 4 ml | Intratracheal |
| 2 | SK02-WT | $10^5$ PFU/ml | 4 ml | Intratracheal |
| 3 | SK02-WT | $10^6$ PFU/ml | 4 ml | Intratracheal |
| 4 | SIV-606 | $10^5$ PFU/ml | 4 ml | Intratracheal |
| 5 | SIV-606 | $10^6$ PFU/ml | 4 ml | Intratracheal |
| 6 | Tx98 | $10^5$ PFU/ml | 4 ml | Intratracheal |
| 7 | Tx98 | $10^6$ PFU/ml | 4 ml | Intratracheal |

Example 4

Protective Effect of SIV-606 in Pigs

To determine whether SIV-606 was immunogenic and could provide protection from SIV infection, the following vaccination and viral challenge studies were performed in pigs. Twenty three H1N1 and H3N2 sero-negative pigs were randomly divided into five groups (n=5, except n=3 in group 5) (Table 2). Two groups of pigs were given MEM and two groups of pigs were vaccinated with $4\times10^6$ PFU of SIV-606 virus intratracheally. Pigs received a second vaccination on day 21. Ten days after the second vaccination (on day 31), pigs were challenged intratracheally with either SIV/SK02 or SIV/Tx98 and were euthanized on day 5 post infection. Sera were collected prior to the first vaccination, 21 days after the first vaccination and 10 days after the second vaccination (before viral challenge). Antigen specific serum IgG and nasal IgA were measured on day 0, 21 and 31.

Figure 14:
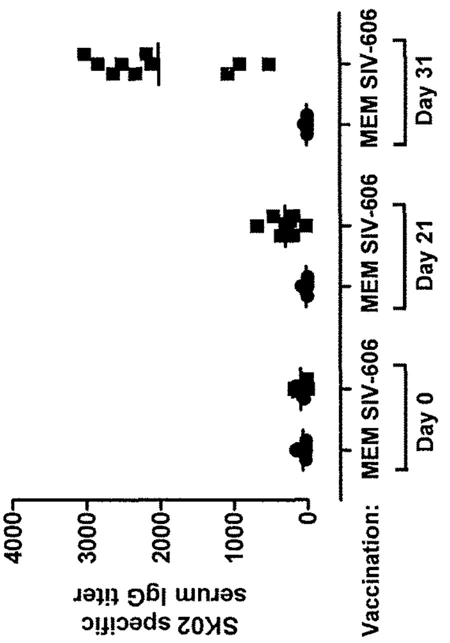
FIGS. 14A-14C show SIV/SK02-specific serum IgG titers (FIG. 14A); SIV/Tx98-specific serum IgG titers (FIG. 14B); and H1N1 Halifax-specific serum IgG titers (FIG. 14C) in pigs vaccinated with SIV-606.
Figure 14:
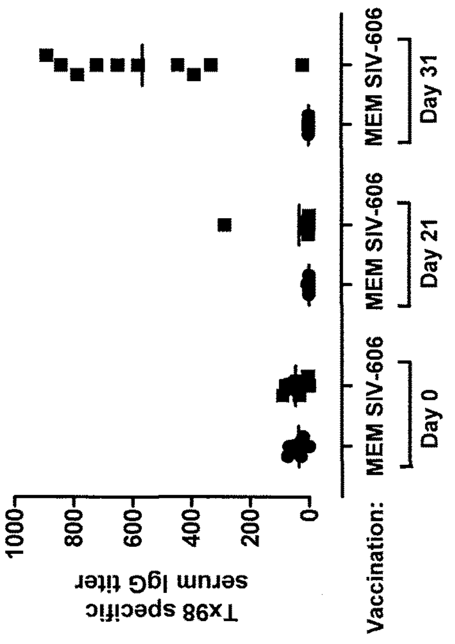
Figure 14:
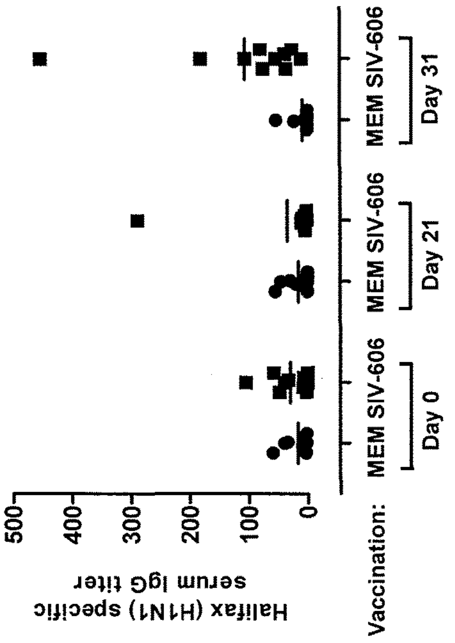

After the first vaccination, SIV/SK02 specific IgG in serum increased significantly and the second dose of SIV-606 boosted IgG response measured on day 31 (FIG. 14A). Serum IgG against SIV/Tx98 or a heterologous H1N1 Halifax210 strain, which was isolated during a 2009 pandemic, increased slightly after one vaccination and increased significantly after the second vaccination (FIGS. 14B and 14C).

Figure 15:
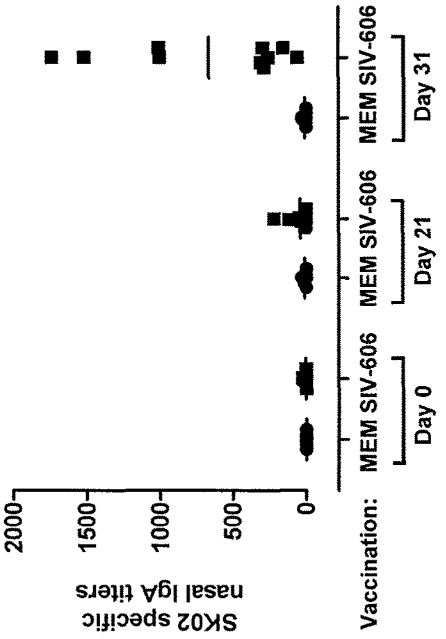
FIGS. 15A-15C show SIV/SK02-specific nasal IgA titers (FIG. 15A); SIV/Tx98-specific nasal IgA titers (FIG. 15B); and H1N1 Halifax-specific nasal IgA titers (FIG. 15C) in pigs vaccinated with SIV-606.
Figure 15:
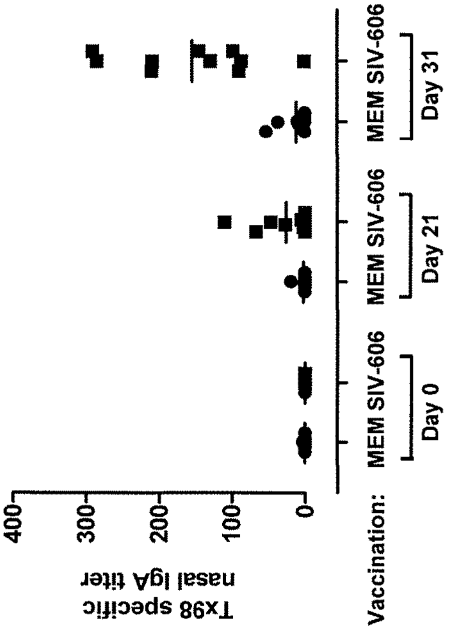
Figure 15:
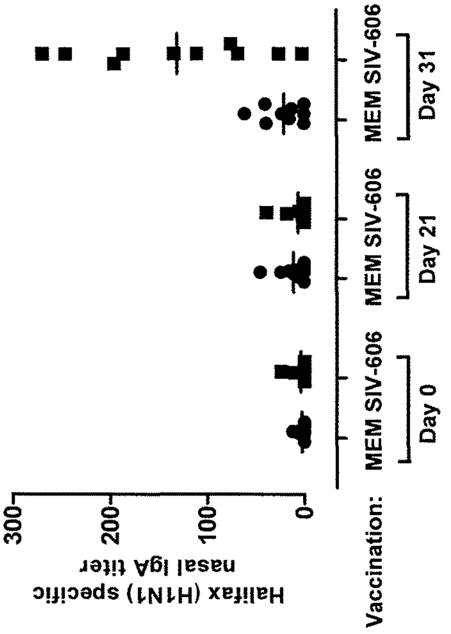
Figure 16:
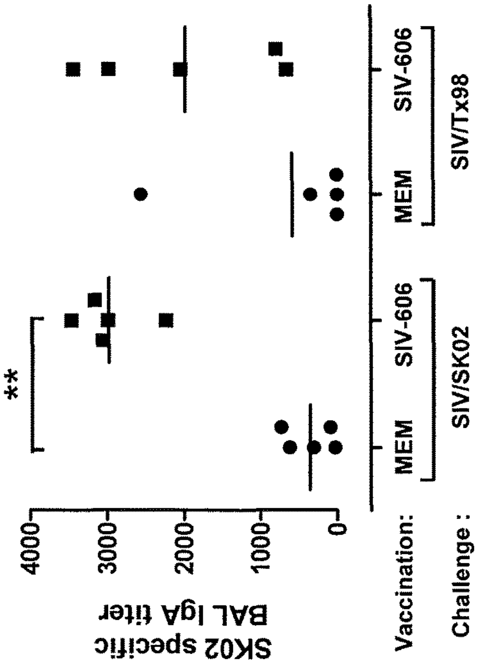
FIGS. 16A-16C show SIV/SK02-specific BALF IgA titers (FIG. 16A); SIV/Tx98-specific BALF IgA titers (FIG. 16B); and H1N1 Halifax-specific BALF IgA titers (FIG. 16C) in pigs vaccinated with SIV-606.
Figure 16:
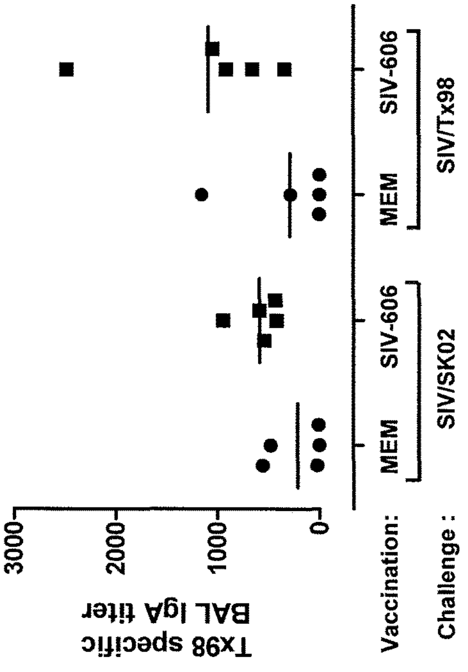
Figure 16:
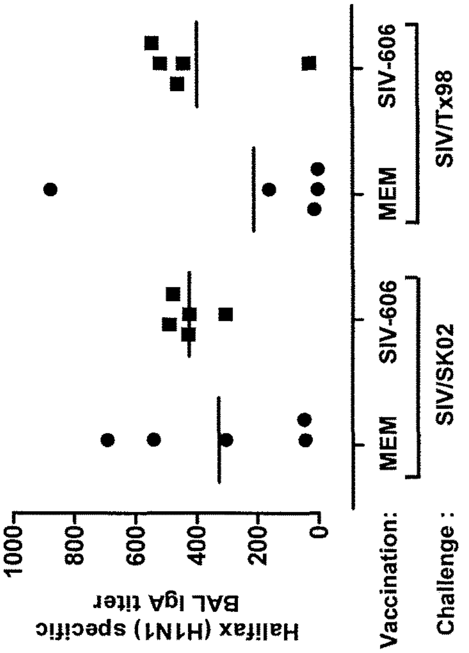

To assess the presence of IgA antibodies specific for H1N1 and H3N2 influenza viruses at mucosal surfaces in the upper and lower respiratory tract, nasal swabs and bronchoalveolar lavage fluid (BALF) samples from pigs in all groups were collected and tested by ELISA. The first vaccination of SIV-606 induced moderate IgA levels in nasal secretion and the second vaccination boosted IgA induction specific to SIV/SK02, SIV/Tx98 and Halifax210 (FIGS. 15A, 15B and 15C). Similarly, IgA titers remained low in BALF after the first vaccination and were significantly higher after the second vaccination (FIGS. 16A, 16B and 16C).

Figure 17:
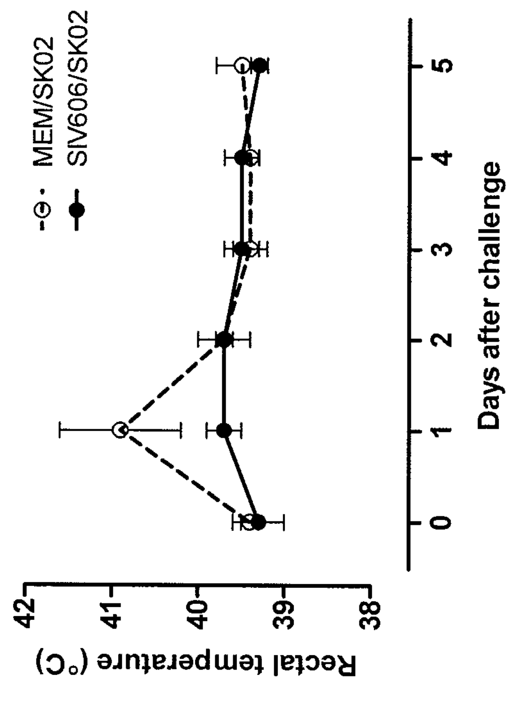
FIGS. 17A and 17B show rectal temperature in unvaccinated control pigs and SIV-606 vaccinated pigs challenged with SIV/SK02 (FIG. 17A) and challenged with SIV/Tx98 (FIG. 17B).
Figure 17:
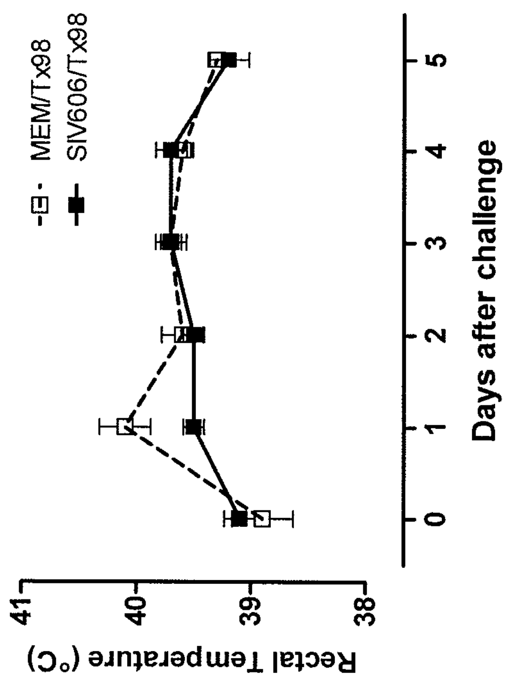

After the viral challenge on day 31, rectal temperature was measured daily for 5 days until necropsy. On day 1 post infection, the pigs vaccinated with MEM and challenged with SIV/SK02 had an onset of fever with a mean rectal temperature of 40.9° C. In contrast, pigs vaccinated with SIV-606 and challenged with SIV/SK02 had a normal temperature ranging between 39.1° C. to 39.6° C. during these five days (FIG. 17A). Similarly, the temperature of pigs vaccinated with MEM and challenged with Tx98 rose to 40.1° C. on day 1 post infection then decreased to 39.6° C. the following day and went back to 39.3° C. on day 5 post infection. Fever was not seen in pigs vaccinated with SIV-606 and challenged with Tx98 (FIG. 17B). The temperature in this group fluctuated between 39.2° C. and 39.7° C. during the 5 days post infection.

Figure 18:
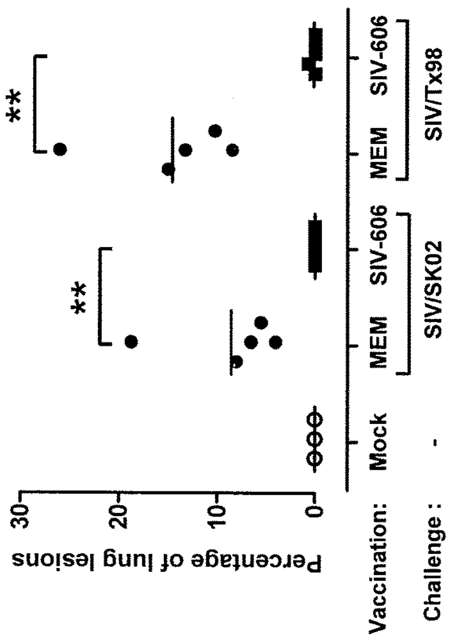
FIGS. 18A and 18B show the percentage of lung lesions (FIG. 18A) and lung viral load (FIG. 18B) in unvaccinated SIV/SK02 and SIV/Tx98 pigs, as well as in pigs vaccinated with SIV-606.
Figure 18:
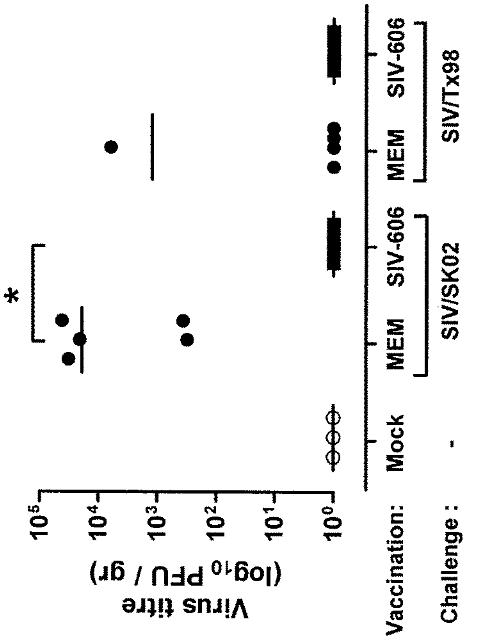

At necropsy, SIV-induced gross lung lesions were examined and scored by the percentage of surface that lesions took up compared to the total lung area (FIG. 18A). All pigs in the unvaccinated groups and challenged with SIV/SK02 or SIV/Tx98 manifested SIV typical gross lesions seen as clear demarcation of dark purple, consolidated areas mostly found in the apical and cardiac lobes. The mean score for these two groups were 8.6 and 14.6, respectively. In contrast, the lungs of pigs vaccinated with SIV-606 and challenged with either SIV/SK02 or SIV/Tx98 had no gross lung lesions.

To measure the viral load in the lungs (FIG. 18B), tissues from the right apical, cardiac and diaphragmatic lobes were collected at necropsy. Virus was detected in the lung tissues from all pigs in the unvaccinated and SIV/SK02 challenged group (mean viral titer was $1.90\times10^4$ PFU per gram). In the unvaccinated and SIV/Tx98 challenged group, virus was only isolated from one pig. No virus was detected in the lung tissues of pigs vaccinated with SIV-606 and challenged with SIV.

Figure 19:
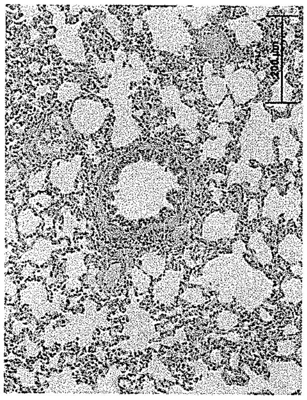
FIGS. 19A-19E show histopathological lesions in unvaccinated, unchallenged pigs (FIG. 19A); MEM vaccinated and challenged pigs (FIG. 19B); SIV-606 vaccinated and SIV/SK02 challenged pigs (FIG. 19C); MEM vaccinated and SIV/Tx98 challenged pigs (FIG. 19D); and SIV-606 vaccinated and SIV/Tx98 challenged pigs (FIG. 19E).
Figure 19:
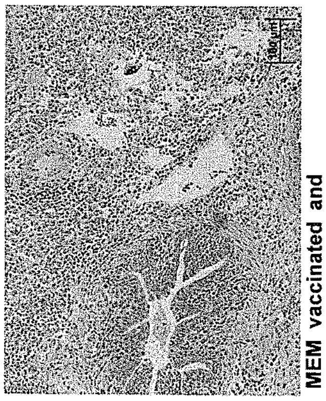
Figure 19:
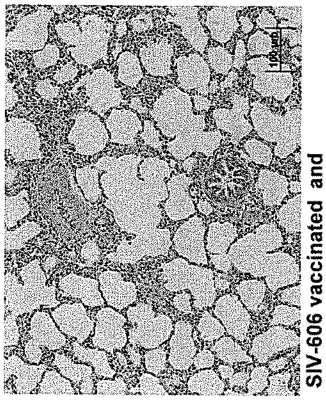
Figure 19:
Figure 19:
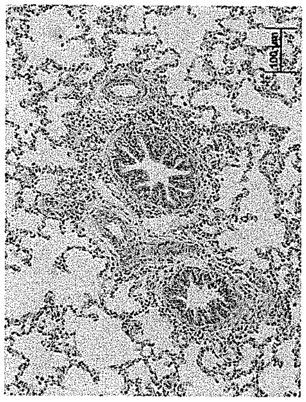

Histophathological lesions were examined using lung tissue samples taken from the right apical, cardiac, and diaphragmatic lobes at necropsy. As shown in FIGS. 19B and 19D, pathological lesions were observed in the lung tissues of unvaccinated and virus challenged groups. The histophathological lesions included the loss of bronchial epithelium due to the necrosis of bronchiolar epithelium, hypertrophy and hyperplasia of bronchiolar epithelium to compensate for the necrosis of bronchiolar epithelium, neutrophil infiltration through the mucosa and into the lumen of bronchioles, peribronchiolar and perivascular lymphocyte infiltration, interstitial thickening, and proliferation of the bronchiolar associated lymphoid tissues. In contrast, no histopathological changes were observed in the lung tissues of SIV-606 vaccinated and challenged groups (FIGS. 19C and 19E). Both SIV-606 vaccinated groups maintained healthy bronchiolar epithelium and alveolar structures with mild interstitial thickening, similar to the tissue shown in the unvaccinated and unchallenged group (FIG. 19A).

TABLE 2

Assignment of pigs for virus challenge

| Group | Vaccination 1 (day 0) | Vaccination 2 (day 21) | Challenge (day 31) |
|---|---|---|---|
| 1 (n = 5) | MEM | MEM | SIV/SK02 |
| 2 (n = 5) | MEM | MEM | SIV/Tx98 |
| 3 (n = 5) | SIV-606 | SIV-606 | SIV/SK02 |
| 4 (n = 5) | SIV-606 | SIV-606 | SIV/Tx98 |
| 5 (n = 3) | — | — | — |

Thus, recombinant, chimeric influenza viruses are disclosed, as well as compositions and methods for treating and preventing influenza. Although preferred embodiments of the subject invention have been described in some detail, it is understood that obvious variations can be made without departing from the spirit and the scope of the invention as defined by the appended claims.

The invention claimed is:

1. A recombinant, chimeric porcine influenza virus, wherein the viral genome consists of eight segments, the virus comprising more than one hemagglutinin (HA) segment from more than one influenza subtype, wherein said virus comprises segments 1-5, 7 and 8 from a first influenza subtype and a second segment 4 from a second influenza subtype, wherein all or a portion of the neuraminidase (NA) segment 6 of the first influenza subtype is missing to render an attenuated virus.

2. The recombinant, chimeric porcine influenza virus of claim 1, wherein said second segment 4 comprises NA packaging sequences from said first influenza subtype located 3' and optionally 5' to said second segment 4.

3. The recombinant, chimeric porcine influenza virus of claim 2, wherein the NA packaging sequences comprise 3' NA packaging sequences from the 3' NA UTR and the 3' NA coding sequence and, optionally 5' NA packaging sequences from the 5' NA UTR and the 5' NA coding sequence.

4. The recombinant, chimeric porcine influenza virus of claim 1, wherein the influenza virus is derived from an influenza A virus.

5. The recombinant, chimeric porcine influenza virus of claim 4, wherein the influenza virus comprises an HA segment from an H1N1 subtype and an HA segment from an H3N2 subtype.

6. The recombinant, chimeric porcine influenza virus of claim 1, wherein the first influenza subtype is H1N1.

7. The recombinant, chimeric porcine influenza virus of claim 6, wherein the H1N1 subtype is A/swine/Saskatchewan/18789/02.

8. The recombinant, chimeric porcine influenza virus of claim 1, wherein the second influenza subtype is H3N2.

9. The recombinant, chimeric porcine influenza virus of claim 8, wherein the H3N2 subtype is A/Swine/Texas/4199-2/98.

10. An attenuated, recombinant, porcine influenza virus, wherein the virus genome consists of a eight segments, the genome comprising segments 1-5, 7 and 8 from an H1N1 influenza subtype, and segment 4 from an H3N2 influenza subtype, wherein all or a portion of segment 6 from the H1N1 influenza subtype is missing, wherein the H3N2 segment 4 is flanked by NA packaging sequences from said H1N1 subtype, wherein the packaging sequences comprise 3' NA packaging sequences from the 3' NA UTR and the 3' NA coding sequence and 5' NA packaging sequences from the 5' NA UTR and the 5' NA coding sequence.

11. The attenuated, recombinant porcine influenza virus of claim 10, wherein the H1N1 subtype is A/swine/Saskatchewan/18789/02 and the H3N2 subtype is A/Swine/Texas/4199-2/98.

12. A composition comprising the recombinant virus of claim 1 and a pharmaceutically acceptable excipient.

13. The composition of claim 12, further comprising an adjuvant.

14. A composition comprising the recombinant virus of claim 10 and a pharmaceutically acceptable excipient.

15. The composition of claim 14, further comprising an adjuvant.

16. A recombinant, chimeric influenza A virus consisting of eight segments, wherein said virus comprises more than one hemagglutinin (HA) segment 4 from more than one influenza subtype, wherein said virus consists of segments 1-5, 7 and 8 from porcine H1N1 subtype A/swine/Saskatchewan/18789/02 and a second segment 4 from porcine H3N2 subtype A/Swine/Texas/4199-2/98, wherein the H3N2 segment 4 comprises neuraminidase (NA) packaging sequences from said H1N1 influenza subtype located 3' and optionally 5' to said second segment 4, such that the virus lacks the remainder of the NA segment 6 of the H1N1 subtype to render an attenuated virus.

17. The recombinant, chimeric influenza virus of claim 16, wherein the NA packaging sequences comprise 3' NA packaging sequences from the 3' NA UTR and the 3' NA coding sequence and, optionally 5' NA packaging sequences from the 5' NA UTR and the 5' NA coding sequence.

18. A composition comprising the recombinant virus of claim 16 and a pharmaceutically acceptable excipient.

19. The composition of claim 18, further comprising an adjuvant.

20. A kit comprising one or more containers of the recombinant virus of claim 16.

* * * * *